US011510921B2

(12) United States Patent
Cincotta

(10) Patent No.: US 11,510,921 B2
(45) Date of Patent: *Nov. 29, 2022

(54) BROMOCRIPTINE FORMULATIONS

(71) Applicant: VEROSCIENCE LLC, Tiverton, RI (US)

(72) Inventor: Anthony H. Cincotta, Tiverton, RI (US)

(73) Assignee: VeroScience LLC, Tiverton, RI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/623,183

(22) PCT Filed: Oct. 18, 2018

(86) PCT No.: PCT/US2018/056554
§ 371 (c)(1),
(2) Date: Dec. 16, 2019

(87) PCT Pub. No.: WO2019/079623
PCT Pub. Date: Apr. 25, 2019

(65) Prior Publication Data
US 2021/0177839 A1    Jun. 17, 2021

Related U.S. Application Data

(60) Provisional application No. 62/573,839, filed on Oct. 18, 2017.

(51) Int. Cl.
*A61K 31/4985* (2006.01)
*A61K 9/00* (2006.01)
*A61K 9/20* (2006.01)
*A61K 47/12* (2006.01)
*A61K 47/14* (2017.01)
*A61K 47/44* (2017.01)

(52) U.S. Cl.
CPC ........ *A61K 31/4985* (2013.01); *A61K 9/0053* (2013.01); *A61K 9/2018* (2013.01); *A61K 47/12* (2013.01); *A61K 47/14* (2013.01); *A61K 47/44* (2013.01)

(58) Field of Classification Search
CPC .................................................. A61K 31/4985
USPC ........................................................ 514/250
See application file for complete search history.

(56) References Cited

U.S. PATENT DOCUMENTS

| | | |
|---|---|---|
| 941,005 A | 11/1909 | Brandt |
| 3,752,814 A | 8/1973 | Fluckiger |
| 4,654,345 A | 3/1987 | Cavanak |
| 4,659,715 A | 4/1987 | Meier et al. |
| 4,749,709 A | 6/1988 | Meier et al. |
| 4,783,469 A | 11/1988 | Meier et al. |
| 5,006,526 A | 4/1991 | Meier et al. |
| 5,066,495 A | 11/1991 | Moro et al. |
| 5,186,420 A | 2/1993 | Beauchamp et al. |
| 5,344,832 A | 9/1994 | Cincotta et al. |
| 5,468,755 A | 11/1995 | Cincotta et al. |
| 5,496,803 A | 3/1996 | Meier et al. |
| 5,523,082 A | 6/1996 | Corbiere |
| 5,554,623 A | 9/1996 | Cincotta et al. |
| 5,565,454 A | 10/1996 | Cincotta |
| 5,585,347 A | 12/1996 | Meier et al. |
| 5,626,860 A | 5/1997 | Cincotta et al. |
| 5,635,512 A | 6/1997 | Cincotta et al. |
| 5,654,313 A | 8/1997 | Cincotta et al. |
| 5,668,155 A | 9/1997 | Cincotta et al. |
| 5,679,685 A | 10/1997 | Cincotta et al. |
| 5,688,794 A | 11/1997 | Meier et al. |
| 5,696,128 A | 12/1997 | Meier et al. |
| 5,700,795 A | 12/1997 | Meier et al. |
| 5,700,800 A | 12/1997 | Cincotta et al. |
| 5,712,265 A | 1/1998 | Meier et al. |
| 5,714,519 A | 2/1998 | Cincotta et al. |
| 5,716,932 A | 2/1998 | Meier et al. |
| 5,716,933 A | 2/1998 | Meier et al. |
| 5,716,957 A | 2/1998 | Cincotta et al. |
| 5,716,962 A | 2/1998 | Cincotta et al. |
| 5,719,160 A | 2/1998 | Cincotta et al. |
| 5,731,287 A | 3/1998 | Meier et al. |
| 5,731,312 A | 3/1998 | Cincotta et al. |
| 5,741,503 A | 4/1998 | Cincotta et al. |
| 5,744,477 A | 4/1998 | Meier et al. |
| 5,750,519 A | 5/1998 | Cincotta et al. |
| 5,756,513 A | 5/1998 | Meier et al. |

(Continued)

FOREIGN PATENT DOCUMENTS

| | | | | |
|---|---|---|---|---|
| CA | 2166204 | * | 4/2009 | ......... A61K 31/4985 |
| CN | 102283844 | | 6/2014 | |

(Continued)

OTHER PUBLICATIONS

[No. Author Listed], "Dissolution," General Chapter 711, U.S. Pharmacopoeia (USP), 34th ed., Dec. 1, 2011, 8 pages.
EP Extended European Search Report in European Appln No. 18868516.8, dated Jun. 29, 2021, 8 pages.
PCT International Preliminary Report on Patentability in International Appln PCT/US2018/056554, dated Apr. 21, 2020, 15 pages.
PCT International Search Report and Written Opinion in International Appl. PCT/US2018/056554, dated, Jan. 3, 2019, 17 pages.
Rathbone et al., academia.edu [Online], "Modified-Release Drug Delivery Technology," Marcel Dekker, Inc., 2003, [Retrieved on Nov. 23, 2018], retrieved from: URL<https:www.academia.edu/28583222/Modified-Release Drug Delivery Technology?auto=downloade>, 90 pages.

(Continued)

*Primary Examiner* — Nizal S Chandrakumar
(74) *Attorney, Agent, or Firm* — Fish & Richardson P.C.

(57) ABSTRACT

The present disclosure describes pharmaceutical formulations of bromocriptine and methods of manufacturing and using such formulations. The formulations are useful for treating physiological disorders including improving glycemic control in the treatment of type 2 diabetes. Also disclosed is synthesis of bromocriptine citrate, and compositions and dosage forms containing bromocriptine citrate.

12 Claims, 10 Drawing Sheets

(56) References Cited

U.S. PATENT DOCUMENTS

| | | |
|---|---|---|
| 5,760,047 A | 6/1998 | Meier et al. |
| 5,792,748 A | 8/1998 | Meier et al. |
| 5,814,638 A | 9/1998 | Lee et al. |
| 5,830,895 A | 11/1998 | Cincotta et al. |
| 5,854,255 A | 12/1998 | Cincotta et al. |
| 5,866,584 A | 2/1999 | Cincotta et al. |
| 5,872,127 A | 2/1999 | Meier et al. |
| 5,872,133 A | 2/1999 | Meier et al. |
| 5,877,183 A | 3/1999 | Cincotta |
| 5,902,811 A | 5/1999 | Cincotta |
| 5,905,083 A | 5/1999 | Meier et al. |
| 5,952,329 A | 9/1999 | Cincotta et al. |
| 6,004,972 A | 12/1999 | Meier et al. |
| 6,071,914 A | 6/2000 | Meier et al. |
| 6,075,020 A | 6/2000 | Meier et al. |
| 6,855,707 B2 | 2/2005 | Cincotta |
| 7,888,310 B2 | 2/2011 | Cincotta |
| 8,021,681 B2 | 9/2011 | Cincotta |
| 8,137,992 B2 | 3/2012 | Cincotta |
| 8,137,993 B2 | 3/2012 | Cincotta |
| 8,137,994 B2 | 3/2012 | Cincotta |
| 8,431,155 B1 | 4/2013 | Cincotta et al. |
| 8,613,947 B2 | 12/2013 | Cincota et al. |
| 8,741,918 B2 | 6/2014 | Cincotta |
| 8,821,915 B2 | 9/2014 | Cincotta |
| 8,877,708 B2 | 11/2014 | Cincotta |
| 9,192,576 B2 | 11/2015 | Cincotta et al. |
| 9,205,084 B2 | 12/2015 | Cincotta |
| 9,352,025 B2 | 5/2016 | Cincotta |
| 9,364,515 B2 | 6/2016 | Cincotta |
| 9,415,005 B2 | 8/2016 | Cincotta |
| 9,522,117 B2 | 12/2016 | Cincotta et al. |
| 9,655,865 B2 | 5/2017 | Cincotta |
| 9,700,555 B2 | 7/2017 | Cincotta et al. |
| 9,895,422 B2 | 2/2018 | Cincotta |
| 9,925,186 B2 | 3/2018 | Cincotta |
| 9,993,474 B2 | 6/2018 | Cincotta et al. |
| 9,999,653 B2 | 6/2018 | Cincotta |
| 10,137,132 B2 | 11/2018 | Cincotta |
| 10,238,653 B2 | 3/2019 | Cincotta |
| 10,307,421 B2 | 6/2019 | Cincotta et al. |
| 10,675,282 B2 | 6/2020 | Cincotta |
| 10,688,094 B2 | 6/2020 | Cincotta et al. |
| 10,688,155 B2 | 6/2020 | Cincotta |
| 10,894,791 B2 | 1/2021 | Cincotta |
| 11,000,522 B2 | 5/2021 | Cincotta et al. |
| 11,045,464 B2 | 6/2021 | Cincotta |
| 11,241,429 B2 | 2/2022 | Cincotta |
| 2001/0016582 A1 | 8/2001 | Cincotta |
| 2002/0146400 A1 | 10/2002 | Cincotta |
| 2002/0187985 A1 | 12/2002 | Cincotta |
| 2004/0028613 A1 | 2/2004 | Quay |
| 2004/0077679 A1 | 4/2004 | Cincotta |
| 2004/0081678 A1 | 4/2004 | Cincotta |
| 2004/0102383 A1 | 5/2004 | Cincotta et al. |
| 2004/0220190 A1 | 11/2004 | Cincotta |
| 2005/0054652 A1 | 3/2005 | Cincotta |
| 2005/0054734 A1 | 3/2005 | Cincotta |
| 2005/0079203 A1 | 4/2005 | Cincotta |
| 2005/0215558 A1 | 9/2005 | Cincotta |
| 2007/0004617 A1 | 1/2007 | Tsai |
| 2008/0200453 A1 | 8/2008 | Cincotta |
| 2008/0293735 A1 | 11/2008 | Cincotta |
| 2009/0137598 A1 | 5/2009 | Cincotta |
| 2009/0137599 A1 | 5/2009 | Cincotta |
| 2009/0143390 A1* | 6/2009 | Cincotta .............. A61K 31/485 514/250 |
| 2010/0035886 A1 | 2/2010 | Nivorozhkin et al. |
| 2011/0136817 A1 | 6/2011 | Cincotta |
| 2011/0195970 A1 | 8/2011 | Cincotta |
| 2011/0195971 A1 | 8/2011 | Cincotta |
| 2012/0129783 A1 | 5/2012 | Cincotta |
| 2012/0142582 A1 | 6/2012 | Cincotta |
| 2013/0197005 A1 | 8/2013 | Cincotta |
| 2013/0274246 A1 | 10/2013 | Cincotta |
| 2013/0287848 A1* | 10/2013 | Cincotta .............. A61K 9/2059 424/468 |
| 2014/0031359 A1 | 1/2014 | Cincotta |
| 2014/0051685 A1 | 2/2014 | Cincotta |
| 2014/0187560 A1 | 7/2014 | Cincotta et al. |
| 2014/0249136 A1 | 9/2014 | Cincotta |
| 2014/0342975 A1 | 11/2014 | Cincotta |
| 2015/0011554 A1 | 1/2015 | Cincotta et al. |
| 2015/0024995 A1 | 1/2015 | Cincotta |
| 2015/0335641 A1 | 11/2015 | Cincotta |
| 2016/0032488 A1 | 2/2016 | Takahashi et al. |
| 2016/0038424 A1 | 2/2016 | Cincotta et al. |
| 2016/0263181 A1 | 9/2016 | Cincotta |
| 2016/0271222 A1 | 9/2016 | Cincotta |
| 2016/0324848 A1 | 11/2016 | Cincotta |
| 2017/0020871 A1 | 1/2017 | Cincotta et al. |
| 2017/0209539 A1 | 7/2017 | Cincotta |
| 2017/0305898 A1 | 10/2017 | Cincotta |
| 2017/0340271 A1 | 11/2017 | Cincotta |
| 2017/0340632 A1 | 11/2017 | Cincotta et al. |
| 2018/0051019 A1 | 2/2018 | Cincotta |
| 2018/0125843 A1 | 5/2018 | Cincotta |
| 2018/0140675 A1 | 5/2018 | Cincotta |
| 2018/0177874 A1 | 6/2018 | Cincotta |
| 2018/0263978 A1 | 9/2018 | Cincotta et al. |
| 2019/0160059 A1 | 5/2019 | Cincotta et al. |
| 2019/0167677 A1 | 6/2019 | Cincotta |
| 2019/0343833 A1 | 11/2019 | Cincotta et al. |
| 2020/0253970 A1 | 8/2020 | Cincotta |
| 2020/0276193 A1 | 9/2020 | Cincotta et al. |
| 2021/0085787 A1 | 3/2021 | Cincotta |
| 2021/0094946 A1 | 4/2021 | Cincotta |
| 2021/0130344 A1 | 5/2021 | Cincotta |
| 2021/0228576 A1 | 7/2021 | Cincotta et al. |
| 2021/0401824 A1 | 12/2021 | Cincotta |
| 2022/0288209 A1 | 9/2022 | Cincotta |

FOREIGN PATENT DOCUMENTS

| | | |
|---|---|---|
| CN | 102727894 | 10/2015 |
| JP | H02-121919 | 5/1990 |
| WO | WO 2002/083141 | 10/2002 |
| WO | WO 2009/091576 | 7/2009 |
| WO | WO 2013/165902 | 11/2013 |
| WO | WO 2017/184875 | 10/2017 |

OTHER PUBLICATIONS

Berge et al., "Pharmaceutical Salts," Journal of Pharmaceutical Sciences, 1977, 66(1):1-19.

Dietrich et al., "Non-alcoholic fatty liver disease, obesity and the metabolic syndrome," Best Practice & Research Clinical Gastroenterology, 2014, 28:637-653.

Pan, "Industrial Pharmaceutics," China Medical Science and Technology Press, the first printing of the 3rd edition, Aug. 2015, p. 47 (Partial English Translation only).

PCT International Search Report and Written Opinion in Application No. PCT/US2017/028656, dated Jul. 7, 2017, 13 pages.

Pukngam et al., "Development and Validation of a Stability-Indicating HPLC Method for Determination of Bromocriptine Mesylate in Bulk Drug and Tablets," Current Pharmaceutical Analysis, 2013, 9:92-101.

Rowe et al., "Mannitol," Handbook of Pharmaceutical Excipients, 7th ed., 2012, 479-482.

Rowe et al., "Stearic Acid," Handbook of Pharmaceutical Excipients, 6th ed, 2009, 697-699.

Singh et al., "Dosage Forms: Non-Parenteral," Encyclopedia of Pharmaceutical Technology, 2008, 749-761.

Stahl et al., "Pharmaceutical Salts: Properties, Selection, and Use," Wiley-VCH, IUPAC, 2002, 329-345.

Vicchi et al., "Dopaminergic drugs in type 2 diabetes and glucose homeostasis," Pharmacological Research, 2016, 109:74-80.

U.S. Appl. No. 16/623,183. dated Dec. 16, 2019.

* cited by examiner

Graph of Dissolution Test Results for VS-ER-NL-55F-A (1.5% BC)

Graph of Dissolution Test Results for VS-ER-NL-55F-A (1.43% BC)

Graph of Dissolution Test Results for VS-ER-NL-55F-C (1.43% BC)

Graph of Dissolution Test Results for VS-ER-NL-55F-D (1.5% BC)

Calibration Curve for 56F Series Dissolution Tests y = 40723x - 8.5657  R² = 0.99989

Graph of Dissolution Test Results for VS-ER-NL-56F-A (1.43% BC)

Graph of Dissolution Test Results for VS-ER-NL-56F-B (2.14% BC)

Graph of Dissolution Test Results for VS-ER-NL-56F-C (1.43% BC)

Graph of Dissolution Test Results for VS-ER-NL-56F-D (1.43% BC)

Graph of Dissolution Test Results for VS-ER-NL-56F-E (2.14% BC)

Graph of Dissolution Test Results for VS-ER-NL-56F-F (=1.43% BC)

BROMOCRIPTINE FORMULATIONS

TECHNICAL FIELD

This invention relates to pharmaceutical formulations and methods of their manufacture and use, and more particularly to formulations of bromocriptine that are useful for treating metabolic or physiological disorders, including type 2 diabetes mellitus (T2DM) and also to synthesis of bromocriptine citrate, and to compositions and dosage forms containing bromocriptine citrate that provide increased stability and water solubility compared to prior art bromocriptine dosage forms. The present invention also relates to synthesis of bromocriptine citrate, and to compositions and dosage forms containing bromocriptine citrate that provide increased heat and humidity stability and water solubility and water stability compared to prior art bromocriptine dosage forms. In another aspect, the invention relates to methods for using these compositions and dosage forms for the treatment of metabolic disorders including type 2 diabetes mellitus (T2DM).

BACKGROUND

Bromocriptine ((5'α)-2-bromo-12'-hydroxy-2'-(1-methylethyl)-5'-(2-methylpropyl)-ergotaman-3',6',18-trione, CAS Registry No. 25614-03-3) is an ergot alkaloid which is a potent dopamine D2 receptor agonist. The compound has the following formula:

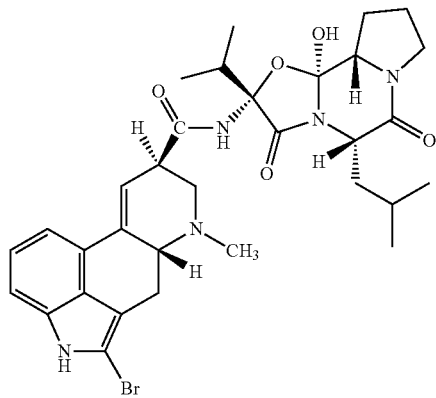

Solid oral dosage forms of bromocriptine are available as bromocriptine mesylate ((5'α)-2-bromo-12'-hydroxy-2'-(1-methylethyl)-5'-(2-methylpropyl)-ergotaman-3',6',18-trione monomethanesulfonate salt, CAS Registry No. 22260-51-1) in a pharmaceutical formulation (e.g., a tablet) containing up to 2.5 mg bromocriptine or in capsule form containing 5 mg bromocriptine. This dosage form of bromocriptine is useful in the treatment of certain hyperprolactinemia-associated dysfunctions and acromegaly, in the prevention of physiological lactation, and in the treatment of Parkinson's disease and prevention of tolerance to Levodopa therapy for Parkinson's disease. In clinical trials, adverse effects included nausea, headache, dizziness, fatigue, lightheadedness, vomiting, abdominal cramps, nasal congestion, constipation, diarrhea, and drowsiness. When bromocriptine is used as described above at appropriate doses, prolactin is reduced to low levels throughout a 24 hour period. CYCLOSET®, a pharmaceutical formulation of bromocriptine mesylate providing a 0.8 mg dose of bromocriptine per tablet, is FDA-approved for once-daily administration to improve glycemic control in adults with type 2 diabetes mellitus, at a dose of 2-6 tablets (1.6 to 4.8 mg total dose). U.S. Pat. Nos. 8,741,918 and 9,41,005 disclose compositions for parenteral administration using dopamine agonists such as bromocriptine, that are useful for treating metabolic-related conditions such as type 2 diabetes.

Bromocriptine, especially the bromocriptine mesylate salt, is prone to light, heat and water decomposition via oxidation and isomerization to form bromocriptinine and other byproducts and to chemical degradation in acidic environments. Bromocriptine and bromocriptine mesylate are particularly susceptible to water-facilitated degradation, particularly to acidic water-facilitated degradation, limiting the biological utility of the bromocriptine.

U.S. Pat. No. 4,654,345 describes a lyophilized formulation of bromocriptine for ophthalmic administration providing reconstituted formulations with improved stability.

U.S. Pat. No. 5,066,495 describes a process for preparing bromocriptine formulations with improved stability by inclusion in an excipient or by separated granulation of excipients and mixing granulate with a mixture of the active ingredient and an excipient having low moisture content.

U.S. Pat. Nos. 5,344,832, 5,554,623, and 5,716,957 discuss a method for modifying and regulating lipid and glucose metabolism by administering a dopamine agonist, e.g., bromocriptine, and/or a prolactin stimulator to reset hormonal timing in the neural centers of the brain to control insulin resistance, hyperinsulinemia, and hyperglycemia.

U.S. Pat. Nos. 5,468,755, 5,756,513, and 5,866,584 discuss a method to modify and regulate lipid and carbohydrate metabolism-generally to reduce obesity, insulin resistance, hyperinsulinemia and hyperglycemia, by administration of a dopamine agonist such as bromocriptine to inhibit prolactin over a limited period at a time of day to reset normal hormonal timing and control insulin resistance, hyperinsulinemia, and hyperglycemia.

U.S. Pat. No. 5,523,082 describes lyophilized formulations of bromocriptine mesylate for ophthalmic administration providing solutions with improved stability of bromocriptine in solution.

U.S. Pat. No. 5,679,685 discusses accelerated release bromocriptine mesylate formulations for regulating prolactin levels that are abnormal during particular times during the day.

U.S. Pat. No. 5,814,638 discusses lyophilized bromocriptine formulations containing cyclodextrin with improved stability.

U.S. Pat. Nos. 9,192,576; 8,613,947; and 8,431,155 describe pharmaceutical formulations of micronized bromocriptine mesylate for oral use.

SUMMARY

Bromocriptine mesylate is not stable under high heat conditions, under exposure to light, or in aqueous environments, particularly acidic aqueous environments. Moreover, bromocriptine is very poorly soluble in aqueous environments. This circumstance limits the shelf life of the compound and importantly also limits the biological utility of the compound, as biological systems (e.g., plasma and cells) are largely aqueous. What is needed is a bromocriptine formulation that is both highly water soluble (much more water soluble than bromocriptine mesylate) and also at the same time stable in the aqueous environment (not labile to water-facilitated degradation). Since water destroys the bromocriptine, enhancing the stability of bromcoritpine by making it more soluble in (i.e, accessible to) water is highly counterintuitive.

The present invention provides for such a unique bromocriptine formulation.

After substantial experimentation with various dosage regimens, and contrary to the general teaching in the art that mesylate salts confer greater water solubility relative to other salts including citrate, it is surprisingly found that bromocriptine formulated as a citrate salt (referred to as bromocriptine citrate) has a markedly increased water solubility versus bromocriptine mesylate. Moreover, bromocriptine mesylate or bromocriptine citrate in combination with certain excipients has the unique ability to markedly improve the heat stability (i.e., protect against heat degradation), aqueous/water stability (i.e., protect against the aqueous/water degradation of bromocriptine) and aqueous/water solubility of bromocriptine compared to the mesylate salt of bromocriptine in its traditional pharmaceutical form (see Table 1). As a result, compared to bromocriptine mesylate in its traditional pharmaceutical form (see Table 1) bromocriptine citrate, particularly in the formulations described herein of excipients containing a short chain saccharide, fatty acid or triglyeride, and citric acid, exhibits a better shelf life (storage stability) in pharmaceutical preparations and additionally provides for longer term stability profiles (i.e., longer duration of appropriate drug activity) in pharmaceutical preparations with respect to bromocriptine dissolution, allowing for a longer storage period between drug manufacture and drug administration, and/or less stringent (e.g., in terms of humidity or temperature) storage conditions. This feature allows for a more flexible (and, thus, less expensive) manufacturing process.

In one aspect, the present disclosure provides a pharmaceutical formulation (e.g., a tablet) that includes bromocriptine (e.g., bromocriptine mesylate or a different bromocriptine salt, e.g., bromocriptine citrate) and an excipient; wherein the bromocriptine is present in an amount that provides a dose of at least about 0.1 mg of bromocriptine per pharmaceutical formulation; and wherein the excipient comprises a triglyceride.

In some embodiments, at least about 80% of the acyl groups of the triglyceride are fatty acid acyl groups of $C_{14}$-$C_{26}$ fatty acids. In some embodiments, at least about 90% of the acyl groups of the triglyceride are fatty acid acyl groups of $C_{14}$-$C_{26}$ fatty acids. In some embodiments, at least about 80% of the acyl groups of the triglyceride are fatty acid acyl groups of $C_{16}$-$C_{20}$ fatty acids. In some embodiments, at least about 90% of the acyl groups of the triglyceride are fatty acid acyl groups of $C_{16}$-$C_{20}$ fatty acids. In some embodiments, at least about 80% of the acyl groups of the triglyceride are fatty acid acyl groups of $C_{18}$ fatty acids. In some embodiments, at least about 90% of the acyl groups of the triglyceride are fatty acid acyl groups of $C_{18}$ fatty acids. In some embodiments, at least about 80% of the acyl groups of the triglyceride are stearoyl or 12-hydroxystearoyl groups. In some embodiments, at least about 90% of the acyl groups of the triglyceride are stearoyl or 12-hydroxystearoyl groups. In some embodiments, at least about 80% of the acyl groups of the triglyceride are saturated. In some embodiments, at least about 90% of the acyl groups of the triglyceride are saturated.

In some embodiments, the excipient includes a hydrogenated vegetable oil. In some embodiments, the excipient includes hydrogenated castor oil, hydrogenated coconut oil, 5 hydrogenated cottonseed oil, hydrogenated palm oil, hydrogenated palm kernel oil, hydrogenated soybean oil or a combination thereof. In some embodiments, the excipient includes hydrogenated castor oil. In some embodiments, the excipient comprises KOLLIWAX® HCO.

In some embodiments, the triglyceride excipient is present in an amount from about 0.5% to about 20% by weight of the formulation.

In some embodiments, an excipient is a particular saccharide (e.g., a monosaccharide, or a disaccharide, excluding lactose).

In some embodiments, the excipient is extragranular.

In some embodiments, the pharmaceutical formulation (e.g., a tablet) when prepared in pharmaceutical standard foil sealed plastic containers and with desiccant included is stable as in the following embodiments: In some embodiments, the pharmaceutical formulation (e.g., a tablet) is stable such that the pharmaceutical formulation contains no more than 5% total related substances (degradant) as determined by HPLC analysis using detection of UV absorption at 300 nm following storage of the pharmaceutical formulation at a temperature of 25±2° C. at about 60±5% relative humidity for about 18 months. In some embodiments, the pharmaceutical formulation is stable such that the pharmaceutical formulation contains no more than 5% total related substances as determined by HPLC analysis using detection of UV absorption at 300 nm following storage of the pharmaceutical formulation at a temperature of 25±5° C. and about 60±5% relative humidity for about 24 months. In some embodiments, the pharmaceutical formulation is stable such that the pharmaceutical formulation contains no more than 5% of bromocriptinine as determined by HPLC analysis using detection of UV absorption at 300 nm following storage of the pharmaceutical formulation at a temperature of 25±2° C. at about 60±5% relative humidity for about 18 months. In some embodiments, the pharmaceutical formulation is stable such that the pharmaceutical formulation contains no more than 5% of bromocriptinine as determined by HPLC analysis using detection of UV absorption at 300 nm following storage of the pharmaceutical formulation at a temperature of 25±5° C. and about 60±5% relative humidity for about 24 months. In some embodiments, the pharmaceutical formulation is stable such that the pharmaceutical formulation contains no more than 3% total related substances as determined by HPLC analysis using detection of UV absorption at 300 nm following storage of the pharmaceutical formulation at a temperature of 40±2° C. at about 70±5% relative humidity for about 6 weeks.

In some embodiments, the pharmaceutical formulation (e.g., a tablet) is stable such that the pharmaceutical formulation contains no more than 8% total related substances (degradant) as determined by HPLC analysis using detection of UV absorption at 300 nm following storage of the pharmaceutical formulation at a temperature of 25±2° C. at about 60±5% relative humidity for about 18 months.

In some embodiments, the pharmaceutical formulation is stable such that the pharmaceutical formulation contains no more than 8% total related substances as determined by HPLC analysis using detection of UV absorption at 300 nm following storage of the pharmaceutical formulation at a temperature of 25±5° C. and about 60±5% relative humidity for about 24 months.

In some embodiments, the pharmaceutical formulation is stable such that the pharmaceutical formulation contains no more than 8% of bromocriptine as determined by HPLC analysis using detection of UV absorption at 300 nm following storage of the pharmaceutical formulation at a temperature of 25±2° C. at about 60±5% relative humidity for about 18 months.

In some embodiments, the pharmaceutical formulation is stable such that the pharmaceutical formulation contains no more than 8% of bromocriptine as determined by HPLC analysis using detection of UV absorption at 300 nm following storage of the pharmaceutical formulation at a temperature of 25±5° C. and about 60±5% relative humidity for about 24 months.

In some embodiments, the pharmaceutical formulation is stable such that the pharmaceutical formulation contains no more than 1% total related substances as determined by HPLC analysis using detection of UV absorption at 300 nm following storage of the pharmaceutical formulation at a temperature of 40±2° C. at about 70±5% relative humidity for about 6 weeks.

In some embodiments, the pharmaceutical formulation is stable such that the pharmaceutical formulation contains no more than 8% total related substances as determined by HPLC analysis using detection of UV absorption at 300 nm following storage of the pharmaceutical formulation at a temperature of 40±2° C. at about 70±5% relative humidity for about 6 months.

In some aspects, the present disclosure provides a pharmaceutical formulation (e.g., a tablet) comprising micronized bromocriptine in an amount that provides a dose of at least about mg of bromocriptine per pharmaceutical formulation; wherein the pharmaceutical formulation is stable such that the pharmaceutical formulation contains no more than 5% of bromocriptine as determined by HPLC analysis using detection of UV absorption at 300 nm following storage of the pharmaceutical formulation at a temperature of 25±2° C. at about 60±5% relative humidity for about 18 months. In some embodiments, the pharmaceutical formulation is stable such that the pharmaceutical formulation contains no more than 5% total related substances as determined by HPLC analysis using detection of UV absorption at 300 nm following storage of the pharmaceutical formulation at a temperature of 25±2° C. at about 60±5% relative humidity for about 18 months. In some embodiments, the pharmaceutical formulation is stable such that the pharmaceutical formulation contains no more than 5% of bromocriptine as determined by HPLC analysis using detection of UV absorption at 300 nm following storage of the pharmaceutical formulation at a temperature of 25±2° C. at about 60±5% relative humidity for about 24 months. In some embodiments, the pharmaceutical formulation is stable such that the pharmaceutical formulation contains no more than 5% total related substances as determined by HPLC analysis using detection of UV absorption at 300 nm following storage of the pharmaceutical formulation at a temperature of 25±2° C. at about 60±5% relative humidity for about 24 months. In some embodiments the pharmaceutical formulation is stable such that the pharmaceutical formulation contains no more than 3% of bromocriptine as determined by HPLC analysis using detection of UV absorption at 300 nm following storage of the pharmaceutical formulation at a temperature of 25±2° C. at about 60±5% relative humidity for about 18 months. In some embodiments, the pharmaceutical formulation is stable such that the pharmaceutical formulation contains no more than 3% total related substances as determined by HPLC analysis using detection of UV absorption at 300 nm following storage of the pharmaceutical formulation at a temperature of 25±2° C. at about 60±5% relative humidity for about 18 months. In some embodiments, the pharmaceutical formulation is stable such that the pharmaceutical formulation contains no more than 3% of bromocriptine as determined by HPLC analysis using detection of UV absorption at 300 nm following storage of the pharmaceutical formulation at a temperature of 25±2° C. at about 60±5% relative humidity for about 24 months. In some embodiments, the pharmaceutical formulation is stable such that the pharmaceutical formulation contains no more than 3% total related substances as determined by HPLC analysis using detection of UV absorption at 300 nm following storage of the pharmaceutical formulation at a temperature of 25±2° C. at about 60±5% relative humidity for about 24 months.

In some embodiments the pharmaceutical formulation is stable such that the pharmaceutical formulation contains no more than 8% of bromocriptinine ine as determined by HPLC analysis using detection of UV absorption at 300 nm following storage of the pharmaceutical formulation at a temperature of 25±2° C. at about 60±5% relative humidity for about 18 months.

In some embodiments, the pharmaceutical formulation is stable such that the pharmaceutical formulation contains no more than 8% total related substances as determined by HPLC analysis using detection of UV absorption at 300 nm following storage of the pharmaceutical formulation at a temperature of 25±2° C. at about 60±5% relative humidity for about 18 months.

In some embodiments, the pharmaceutical formulation is stable such that the pharmaceutical formulation contains no more than 8% of bromocriptine as determined by HPLC analysis using detection of UV absorption at 300 nm following storage of the pharmaceutical formulation at a temperature of 25±2° C. at about 60±5% relative humidity for at least 24 months.

In some embodiments, the pharmaceutical formulation is stable such that the pharmaceutical formulation contains no more than 8% total related substances as determined by HPLC analysis using detection of UV absorption at 300 nm following storage of the pharmaceutical formulation at a temperature of 25±2° C. at about 60=5% relative humidity for about 24 months.

In some embodiments, the pharmaceutical formulation is stable such that the pharmaceutical formulation contains no more than 1% total related substances as determined by HPLC analysis using detection of UV absorption at 300 nm following storage of the pharmaceutical formulation at a temperature of 40±2° C. at about 70±5% relative humidity for about 6 weeks.

In some embodiments, the pharmaceutical formulation is stable such that the pharmaceutical formulation contains no more than 8% total related substances as determined by HPLC analysis using detection of UV absorption at 300 nm following storage of the pharmaceutical formulation at a temperature of 40±2° C. at about 70±5% relative humidity for about 6 months.

In some embodiments of the pharmaceutical formulations described above, the bromocriptine is micronized.

In some embodiments, the bromocriptine has a Dv90 of about 20 μm or lower. In some embodiments, the bromocriptine has a Dv90 of about 10 μm or lower.

In some embodiments, the bromocriptine has a Dv90 of about 5 μm or lower. In some embodiments, the bromocriptine has a Dv99 of about 20 μm or lower. In some embodiments, the bromocriptine has a Dv99 of about 10 μm or lower.

In some embodiments, the bromocriptine has a volume-based particle size distribution wherein not more than about 20% of the bromocriptine has a particle size of less than about 1 μm.

In some embodiments, the pharmaceutical formulation provides a dissolution profile, when tested in USP Apparatus Type 2 Paddle Method at 50 rpm in 500 ml of 0.1 N hydrochloric acid at about 37° C., wherein at least about 80% of the bromocriptine has been released at about 30 minutes.

In some embodiments, the pharmaceutical formulation provides a dissolution profile, when tested in USP Apparatus Type 2 Paddle Method at 50 rpm in 500 ml of 0.1 N hydrochloric acid at about 37° C., wherein at least about 90% of the bromocriptine has been released at about 30 minutes.

In some embodiments, the pharmaceutical formulation provides a dissolution profile, when tested in USP Apparatus Type 2 Paddle Method at 50 rpm in 500 ml of 0.1 N hydrochloric acid at about 37° C., wherein at least about 95% of the bromocriptine has been released at about 30 minutes.

In some embodiments, the pharmaceutical formulation provides a dissolution profile, when tested in USP Apparatus Type 2 Paddle Method at 50 rpm in 500 ml of 0.1 N hydrochloric acid at about 37° C., wherein at least about 90% of the bromocriptine has been released at about 20 minutes.

In some embodiments, the pharmaceutical formulation provides a dissolution profile, when tested in USP Apparatus Type 2 Paddle Method at 50 rpm in 500 ml of 0.1 N hydrochloric acid at about 37° C., wherein not more than about 50% of the bromocriptine has been released at about 7 minutes.

In some embodiments, the pharmaceutical formulation provides a dissolution profile, when tested in USP Apparatus Type 2 Paddle Method at 50 rpm in 500 ml of 0.1 N hydrochloric acid at about 37° C., wherein not more than about 75% of the bromocriptine has been released at about 10 minutes.

In some embodiments, the pharmaceutical formulation provides a pharmacokinetic profile wherein the time to maximum plasma concentration ($T_{max}$) following administration of the pharmaceutical formulations (e.g., six pharmaceutical formulations each comprising a dose of 0.8 mg of bromocriptine) to adult subjects is between about 30 and 60 minutes when the pharmaceutical formulations are administered under fasting conditions.

In some embodiments, the pharmaceutical formulation provides a pharmacokinetic profile comprising) a Tmax at about 1 to about 90 minutes after administration of the parenteral dosage form; and b) a plasma drug concentration of at least 50% Cmax for a duration of about 90 to about 360 minutes after Tmax when said dosage form is administered parenterally In some embodiments, the pharmaceutical formulation comprises citric acid as an excipient. In some embodiments, the citric acid is present in an amount from about 1% to about 7% by weight.

In some embodiments, the pharmaceutical formulation comprises a disintegrant. In some embodiments, disintegrant is present in an amount from about 5% to about 20% by weight.

In some embodiments, the bromocriptine is present in an amount that provides a dose of about 0.8 mg of bromocriptine per pharmaceutical formulation.

In some embodiments, the pharmaceutical formulation comprises a triglyceride or diglyceride or a phospholipid, including phosphatidylcholine.

In some embodiments, the pharmaceutical formulation comprises a shortchain saccharide exclusive of lactose.

In some embodiments the short chain saccharide comprises mannitol

In some embodiments the pharmaceutical formulation comprises the fatty acid, stearic acid. In another aspect, the present disclosure provides a method for the manufacture of a bromocriptine pharmaceutical formulation comprising blending the bromocriptine with excipients to form a mixture wherein the bromocriptine is substantially evenly distributed in the mixture, and compressing the mixture to form a pharmaceutical formulation.

In some embodiments, the method includes processing bromocriptine to reduce the average particle size of the bromocriptine to provide bromocriptine that has a Dv90 of about 20 μm or less prior to the blending.

In some embodiments, the method includes determining that bromocriptine has a particle size distribution equivalent to a volume-based particle size distribution with a Dv90 of about 20 μm or less prior to the blending, so that the bromocriptine that is blended is of determined particle size distribution.

In some embodiments, the bromocriptine can have a particle size of 0.1 to 100 μm diameter.

In an aspect, the present disclosure provides a pharmaceutical formulation prepared according to such methods.

In some embodiments the present disclosure provides a method for treating metabolic disorders including T2DM in a subject in need of such treatment, the method including administering to the subject a solid dosage form such as a tablet or capsule containing bromocriptine citrate, a short chain saccharide such as mannitol and stearic acid.

In another embodiment the method can include orally and/or parenterally administering the solid dosage form containing bromocriptine citrate, a short chain saccharide such as mannitol and stearic acid to the subject. The formulation can also contain citric acid.

Any of the above-described methods can include the administration of between about 0.05 μg and about 0.5 mg/kg per day of bromocriptine citrate to the subject.

Oral formulations generally contain 30-60% by weight of a short chain saccharide, while parenteral (sublingual) formulations contain 60-90% by weight of a short chain saccharide.

Any of the above-described methods can further include treating the subject with one or more additional therapeutic regimens. The additional therapeutic regimens can include, e.g., administering one or more dopamine D1 receptor agonists, alpha-1 adrenergic antagonists, alpha-2 adrenergic agonists, serotonergic inhibitors, and/or serotonin 5HT1b agonists. Alternately or in addition, the additional therapeutic regimens can include, e.g., administering one or more peripheral acting agents.

In some embodiments the present disclosure provides for a formulation containing micronized bromocriptine citrate, a short chain saccharide such as mannitol, a fatty acid such as stearic acid or a triglyceride, and citric acid as an excipient.

In some embodiments, the present disclosure provides a formulation containing between 0.1-10% bromocriptine citrate, 0.1-10% citric acid, 30-90% non-lactose short chain saccharide, and 0.2-10% free fatty acid, phospholipid or triglyceride.

In some embodiments, the present disclosure provides a formulation containing between 0.1-10% bromocriptine citrate, 0.1-10% citric acid, 60-90% non-lactose short chain saccharide, and 0.2-10% free fatty acid, phospholipid or triglyceride.

In another embodiment the present disclosure provides a formulation containing (by weight) between 0.1-8% bromocriptine citrate, 0.5-8% citric acid, 65-90% non-lactose short chain saccharide, and 0.2-5% free fatty acid, phospholipid or triglyceride.

In one preferred embodiment the present disclosure provides a formulation containing (by weight) 0.1-5% bromocriptine citrate, 0.5-5% citric acid, 70-90% non-lactose short chain saccharide, and 0.2-3.0% free fatty acid, phospholipid or triglyceride In some embodiments the present disclosure provides a method for treating metabolic disorders including T2DM in a subject in need of such treatment, by administering to the subject a solid dosage form such as a tablet or capsule containing (micronized) bromocriptine citrate, a short chain saccharide such as mannitol, a fatty acid such as stearic acid or a triglyceride, and citric acid.

In another embodiment the method can include orally and/or parenterally administering the solid dosage form containing bromocriptine citrate, a short chain saccharide such as mannitol a fatty acid such as stearic acid or a triglyceride to the subject. The formulation can also contain citric acid.

The term "parenteral administration" is defined herein to mean a form of administration or dosage form that provides for the absorption of a substantial amount of the drug through other than the gastric and/or intestinal mucosa of the GI tract.

Any of the above-described methods can include the administration of between about 0.05 μg and about 0.5 mg/kg per day of bromocriptine citrate to the subject.

Any of the above-described methods can further include treating the subject with one or more additional therapeutic regimens. Alternately or in addition, the additional therapeutic regimens can include, e.g., administering one or more peripheral acting agents. In an aspect, the present disclosure provides a method of treatment for improving glycemic control in a type 2 diabetes patient comprising administering to the patient or providing to the patient for administration one or more bromocriptine pharmaceutical formulations as described herein.

In an aspect, the present disclosure provides a method of treatment for improving metabolic disorders such as glycemic control in a type 2 diabetes patient or key elements of metabolic disorders comprising manufacturing one or more bromocriptine pharmaceutical formulations according to the methods of manufacture disclosed herein and administering the one or more of the pharmaceutical formulations to the patient or providing one or more of the pharmaceutical formulations to the patient for administration.

In an aspect, the present disclosure provides a method of treating a metabolic disorder or key element thereof by administering the herein described bromocriptine formulations within 4 hours of waking in the morning or so as to produce a daily peak in dopamine agonist activity in the body within about 4 hours of waking in the morning.

The details of one or more embodiments of the invention are set forth in the accompanying drawings and the description below. Other features, objects, and advantages will be apparent from the description and drawings, and from the claims.

DETAILED DESCRIPTION

Figure 1A:
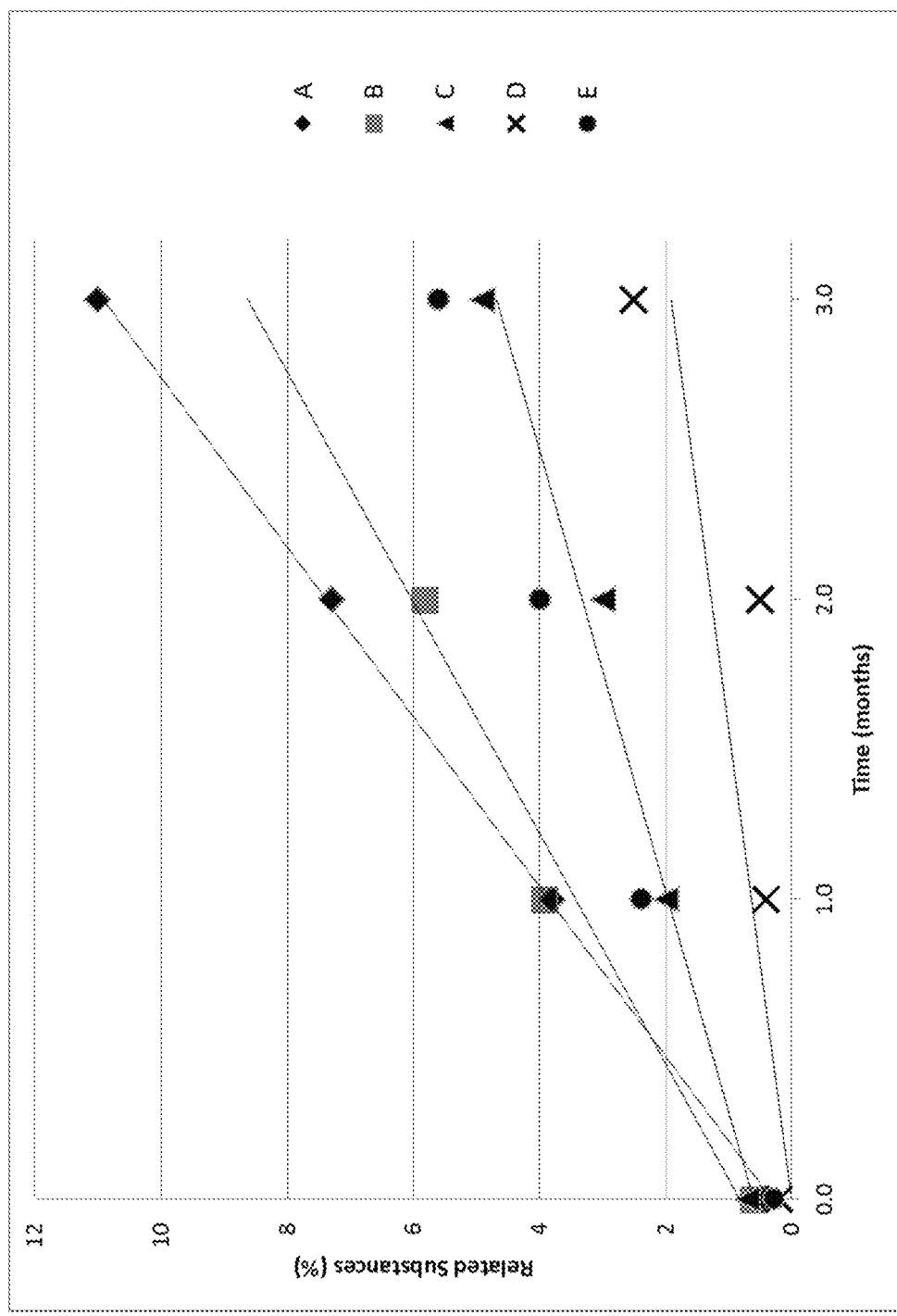
FIG. 1A shows a plot of the total related substances impurity measured for bromocriptine mesylate pharmaceutical formulation formulations prepared using micronized bromocriptine mesylate and various lubricants at the beginning of an experiment to measure product stability (T=0) and following storage at 40±2° C. and 75±5% RH for 1, 2 or 3 months.

"About" or "Approximately," as used herein, means approximately, e.g., plus or minus approximately ten percent of the indicated value. "Particle," as used herein, refers to an aggregated physical unit of a compound (e.g., bromocriptine mesylate or a different bromocriptine salt, e.g., bromocriptine citrate), i.e., a piece or a grain.

"Particle size," as used herein, refers to the average linear dimension of a particle of a compound, for example the diameter of a spherical particle of a compound.

"Micronization," as used herein, refers to a process of reducing the average particle size of a solid material, typically to provide particles with a particle size of a few micrometers.

"Micronized," as used herein, refers to a material that has been subjected to micronization.

"Short chain saccharide" as used herein refers to monosaccharides or disaccharides, (excluding lactose) including but not limited to, mannitol, xylitol, dextrose, maltose, sucrose, galactose, fructose, and sorbitol The term "oral dosage form" refers to a drug dosage form that provides for absorption of a substantial amount of the drug through the gastric and/or intestinal mucosa of the gastrointestinal tract.

The term "pharmaceutical formulation" refers to an oral dosage form that comprises a mixture of active substances and excipients, usually in powder form, pressed or compacted from a powder into a solid dose.

"Particle size distribution," as used herein, refers to the relative proportions of particles of a compound, such as bromocriptine mesylate or a different bromocriptine salt, e.g., bromocriptine citrate, having a given particle size. While the particle size of a spherical object can be unambiguously and quantitatively defined by its diameter, particles comprising an active pharmaceutical ingredient, such as bromocriptine mesylate for example, may be non-spherical and irregular in shape. There are several methods by which those of ordinary skill in the art measure and express the size of non-spherical and irregular particles, such as measuring the size of such particles using laser diffractometry and expressing the size of such particles based on replacing a given particle with an imaginary sphere that has one of a number of properties of the particle. Such properties can be selected from, e.g., but are not limited to, the diameter of an imaginary sphere having the same volume of the particle being measured (volume-based particle size), the diameter of an imaginary sphere having the same weight as the particle being measured (weight-based particle size), and the diameter of an imaginary sphere having the same surface area as the particle being measured (area-based particle size). Those having ordinary skill in the art are familiar with such methods, and the manner in which the results of such methods are expressed, and such methods can be applied to the embodiments disclosed herein without undue experimentation. The particle size distribution may be represented, e.g., graphically as a plot. A common type of plot is a cumulative undersize plot which represents the fraction (e.g., by number, volume or mass) of particles that are smaller than the stated particle size.

The parameters Dv10, Dv50, Dv90 and Dv99 represent the particle size at the 10%, 50%, 90% and 99% points of the cumulative volume undersize particle size distribution. Thus, a "Dv10" for a material represents a particle size wherein 10% of the volume of the material consists of particles having a particle size equal to the Dv10 value or smaller. A "Dv50" for a material represents a particle size wherein 50% of the volume of the material consists of particles having a particle size equal to the Dv50 value or smaller. A "Dv90" for a material represents a particle size wherein 90% of the volume of the material consists of particles having a particle size equal to the Dv90 value or smaller. A "Dv99" for a material represents a particle size wherein 99% of the volume of the material consists of particles having a particle size equal to the Dv99 value or smaller.

The term "span" as used herein means a measure of the width of the distribution of given particle sizes of a given compound comprising an embodiment disclosed herein. In particular, the span of a given embodiment can be provided by measuring the size of the particles of a given compound using a volume-based particle size distribution method and applying the formula below, wherein Dv90, Dv10 and Dv50 are as hereinbefore defined:

$$\text{Span} = \frac{Dv90 - Dv10}{Dv50}$$

The term "fatty acid" as used herein is a carboxylic acid with a long aliphatic chain (tail) containing from about 4 to about 26 carbon atoms. An "unsaturated" fatty acid is a fatty acid that contains at least one C=C double bond between carbon atoms of the fatty acid aliphatic chain. A "saturated" fatty acid is a fatty acid that lacks any C=C double bonds between the carbon atoms of the aliphatic chain.

A "triglyceride" is an ester that is formally derived from glycerol and three fatty acids, i.e., a triacylglyceride wherein the acyl groups are derived fatty acids.

The term "treating" or "treatment" as used herein means the treating or treatment of a disease or medical condition (such as type 2 diabetes) in a patient, such as a mammal (particularly a human) that comprises ameliorating the disease or medical condition, i.e., eliminating or causing regression of the disease or medical condition in a patient, suppressing the disease or medical condition, i.e., slowing or arresting the development of the disease or medical condition in a patient; or alleviating the symptoms of the disease or medical condition in a patient.

The present disclosure describes improved bromocriptine formulations for improving glycemic control and treating type 2 diabetes, manufacturing methods for preparing such formulations, as well as methods of using such formulations. The formulations may contain bromocriptine (e.g., bromocriptine mesylate or a different bromocriptine salt, e.g., bromocriptine citrate) in an amount that provides a dose of at least about 0.1 mg, e.g., about 0.8 mg, of bromocriptine. The bromocriptine may be present in the formulations as the sole pharmaceutically active ingredient. The bromocriptine formulations may be an oral dosage form, e.g., pharmaceutical formulations (e.g., a tablet). The bromocriptine may be substantially evenly distributed in the pharmaceutical formulations.

Bromocriptine citrate can be prepared directly from the bromocriptine free base or from the bromocriptine mesylate salt after desalting to the bromocriptine free base. Bromocriptine mesylate as well as the free base is commercially available from several sources (e.g., Sigma Aldrich and Euticals). In contrast to the mesylate, bromocriptine citrate is not an alkylating agent and is therefore safer for long term parenteral (e.g. sublingual)) administration. Desalting of the bromocriptine mesylate to generate the bromocriptine free base can be accomplished by any of a variety of known desalting techniques. Such techniques are generally known in the art and include desalting by, e.g., gel filtration (e.g., Sephadex (cross-linked dextran gel) filtration column), dialysis, ion exchange column purification (effecting removal of mesylate by binding to the charged column), and/or diafiltration or ultrafiltration (use of permeable membranes to separate molecules based upon size). The solvent for the desalting process can be a variety of organic solvents and/or combinations of solvents, such as, e.g., methanol, ethanol, and/or chloroform. Also, the desalting process may additionally employ phase separation between aqueous and organic solvent phases, with the salt isolated in the aqueous phase and the bromocriptine isolated in the organic phase. Additionally, the free base of bromocriptine can be generated from the mesylate salt by extraction of the mesylate from bromocriptine by dissolving the bromocriptine mesylate in an organic solvent (not miscible with water) that forms a bilayer upon addition of an aqueous solution of a pH in which the mesylate migrates into the aqueous phase while the bromocriptine remains in the organic phase. The free base bromocriptine can subsequently be washed with repeated organic/aqueous separations and dried to purity.

Citric acid is a tribasic compound with pKa values of 3.13, 4.76, and 6.40. As such, the bromocriptine citrate described herein may be of the mono, di, or tri citrate forms or combinations thereof. Starting with the bromocriptine free base, the preparation of the citrate salt can be accomplished by any of the following general methods.

Method 1: Citric acid (about 1-3 grams) is dissolved in absolute (i.e., about 100%) ethanol at room temperature in a reaction vessel, to which an ethanol solution of bromocriptine (about 2-10 grams) is then added in an equi-mole amount to the citric acid. Citric acid may also be present in excess of the bromocriptine free base. The resulting solution is stirred for about some time, e.g., 2-24 hours at room temperature and is then evaporated under vacuum, e.g., on a rotary evaporator. The resulting semi-solid or solid product is then dissolved in, e.g., an ethanol type mixture, e.g., straight ethanol or acetone-ethanol mixture (e.g., a 50:50 mixture) and subsequently dried under vacuum. Other mixtures (e.g., other organic solvent systems, e.g., methanol) and/or other mixture ratios (e.g., a 5:95, 10:90, 20:80, 25:75, 30:70, 40:60, 60:40, 70:30, 75:25, 80:20, 90:10, or 95:5 mixture) can be used. The resulting precipitate is bromocriptine citrate.

Method 2: Citric acid (about 1-3 grams) is dissolved in methanol. Bromocriptine (about 2-10 grams) is also dissolved in methanol then added directly to the citrate citric acid solution in an equi-mole amount to the citric acid Citric acid may also be present in excess of the bromocriptine free base. The two solutions are then mixed and then stirred (about 2-24 hours at room temperature) and then evaporated to dryness (e.g., under vacuum, e.g., using a rotary evaporator). The resulting residue is bromocriptine citrate.

Method 3: Citric acid (about 1-3 grams) is dissolved in butanol and bromocriptine (about 2-10 grams) dissolved in butanol is then added to this solution in an equi-mole amount to the citric acid (citric acid may also be present in excess of the bromocriptine free base) and stirred at room temperature for about 2-24 hours. The solvent is removed under vacuum; the resulting precipitate is bromocriptine citrate. The isolated precipitate may be re-dissolved in butanol and water to create a two phase system. The phases are separated and the organic phase is evaporated to dryness to yield purified bromocriptine citrate.

Method 4: Citric acid (about 1-3 grams) is dissolved in a water/ethanol solvent, to which a water/ethanol solution containing bromocriptine (about 2-10 grams) is added in an equi-mole amount to the citric acid. Citric acid may also be present in excess of the bromocriptine free base. Various organic solution(s) containing bromocriptine can be used. For example, bromocriptine can be dissolved in one or more organic solvents, e.g., methanol, propanol, or butanol. The resulting solution is stirred at room temperature for about 2-24 hours; the solution is then evaporated to dryness. The dried solid can be washed in methanol and re-precipitated by evaporation to dryness. The resulting residue is bromocriptine citrate.

Method 5 Citric acid (about 1-3 grams) is dissolved in any organic solvent or aqueous/organic solvent in which bromocriptine is soluble. Bromocriptine (about 2-10 grams) is dissolved in the same organic solvent or aqueous/organic solvent as the citric acid or in a solvent that is miscible with the solvent used to solvate the citric acid and then added to and mixed with the citric acid/organic solution in an equi-mole amount to the citric acid. Citric acid may alsobe present in excess of the bromocriptine free base. The resulting solution is stirred at room temperature for about 2-24 hours. The solution is evaporated to dryness to yield bromocriptine citrate. In each of the above examples it is preferred to use the citric acid and bromocriptine solutions at near their saturation point). One or more chemical modifications generally known in the art can be made to the above-described methods to enhance or optimize the purity and/or yield of bromocriptine citrate. For example, the pH of the bromocriptine and citric acid solutions may be adjusted to optimize the formation of the bromocriptine citrate. As further non-limiting examples, one or more organic solvents (e.g., methanol, propanol, or butanol) can be used to dissolve, re-suspend, and/or re-precipitate citric acid, bromocriptine, and/or bromocriptine citrate. The pKa of bromocriptine and citric acid can be adjusted, for example, by changing the solvent used to prepare the citric acid or bromocriptine solutions. The basic forms of citric acid may also be employed in these methods (e.g. sodium citrate), though the citric acid form is preferred. One or more steps in any of the above-described methods can be carried out at a different (i.e., lower or higher) temperature or pH; alternately or in addition, the temperature can be varied over time during one or more steps. The final product (i.e., bromocriptine citrate) can be re-precipitated to reduce and/or remove any impurities (such as, e.g., bromocriptine free base or unassociated/unbound citric acid or water). In each method, the product can be "cleaned" (e.g., using one or more of the above-described techniques, e.g., dissolution, resuspension, and/or re-precipitation) to remove unreacted bromocriptine or citrate. Water may be removed by fractional distillation or other standard dewatering techniques known to those skilled in the art.

Further, bromocriptine citrate will provide for pharmaceutical preparations with more efficient absorption across biological cellular membranes relative to bromocriptine mesylate. Still further, due to the unexpectedly improved degradation resistance of bromocriptine citrate to heat and water (e.g., in a physiological environment) and its simultaneously increased aqueous solubility (a phenomenon not predicted by the art) relative to bromocriptine mesylate, minimum and preferred dosages of bromocriptine citrate for treating vertebrates are lower than the minimum and preferred dosages of bromocriptine mesylate for an equivalent therapeutic effect and treatment duration. Taken together, the unanticipated advantages of bromocriptine citrate provide for a substantial improvement over the use of bromocriptine mesylate in the current commercial bromocriptine pharmaceutical preparations (e.g., CYCLOSET® or PARLODEL®), providing a more stable, more efficient and more biologically compatible compound, with more predictable and reproducible effects, for pharmaceutical preparations of bromocriptine for the treatment of any of a variety of medical disorders including prediabetes, obesity, insulin resistance, hyperinsulinemia, hyperglycemia and type 2 diabetes mellitus (T2DM). The enhanced properties of pharmaceutical preparations of bromocriptine citrate cannot be mimicked by the mere addition of citrate to pharmaceutical preparations of bromocriptine mesylate. Due to its increased solubility in water, bromocriptine citrate will display increased absorption in vivo as compared to bromocriptine mesylate.

Bromocriptine citrate may be administered, with or without a dopamine $D_i$ receptor agonist such as SKF-38393, SKF-82958 or SU-82957 to treat one or more of the metabolic disorders associated with MS, including, e.g., T2DM, hypertension, hypertriglyceridemia, a pro-inflammatory state, insulin resistance, fatty liver, NASH, CVD, and/or obesity Bromocriptine citrate may further optionally be administered in conjunction with one or more of an alpha-1 adrenergic antagonist, an alpha-2 adrenergic agonist, or a serotonergic inhibitor, optionally further in combination with a serotonin $5HT_{1b}$ agonist. Examples of such agents are known in the art and are disclosed in, e.g., U.S. Pat. No. 5,877,183. Bromocriptine citrate may still further optionally be administered in conjunction with various peripheral acting agents, e.g., HMGCoA reductase inhibitors, anti-hypertensives, anti-diabetes agents including, e.g., postprandial insulin secretagogues or insulin itself, anti-inflammatory agents, and anti-coagulative agents. Examples of such agents are known in the art and are disclosed in, e.g., Int'l. Pat. App. Pub. No. WO 2009/091576 A2.

Bromocriptine citrate is administered to the vertebrate, animal or human, preferably orally or sublingually, optionally parenterally, for the treatment of any one or more symptoms desirable of change, e.g., obesity or hyperglycemia.

The solid pharmaceutical compositions of the invention should include an amount of the compound(s) of the invention effective for treatment of metabolic diseases and disorders such as, but not limited to, T2DM, obesity, prediabetes, Metabolic Syndrome, cardiometabolic risk, hypertension, dyslipidemia, insulin resistance, hyperinsulinemia, hepatic steatosis, renal disease, cardiovascular disease, cerebrovascular disease, and peripheral vascular disease and biomarkers of impending vascular disease. The effective dosage will depend on the severity of the diseases and the activity of the particular compound(s) employed, and is thus within the ordinary skill of the art to determine for any particular host mammal or other host organism. Suitable dosages of bromocriptine citrate for a vertebrate (e.g., a human) may be, e.g., in the range of about 0.05 μg to about 0.5 mg per kg BW, optionally in the range of about 0.1 μg to about 0.3 mg per kg BW or in one preferred embodiment between about 2 μg and 0.1 mg/kg, BW per day. A suitable pharmaceutical dosage form comprising bromocriptine citrate may have a total weight of, e.g., (including excipients) of between about 2.5 mg and about 2000 mg.

In each of the above examples it is preferred to use the citric acid and bromocriptine solutions at near their saturation point. One or more chemical modifications generally known in the art can be made to the above-described methods to enhance or optimize the purity and/or yield of bromocriptine citrate. For example, the pH of the bromocriptine and citric acid solutions may be adjusted to optimize the formation of the bromocriptine citrate. As further non-limiting examples, one or more organic solvents (e.g., methanol, propanol, or butanol) can be used to dissolve, re-suspend, and/or re-precipitate citric acid, bromocriptine, and/or bromocriptine citrate. The pKa of bromocriptine and citric acid can be adjusted, for example, by changing the solvent used to prepare the citric acid or bromocriptine solutions. The basic forms of citric acid may also be employed in these methods (e.g. sodium citrate), though the citric acid form is preferred. One or more steps in any of the above-described methods can be carried out at a different (i.e., lower or higher) temperature or pH; alternately or in addition, the temperature can be varied over time during one or more steps. The final product (i.e., bromocriptine citrate) can be re-precipitated to reduce and/or remove any impurities (such as, e.g., bromocriptine free base or unassociated/unbound citric acid or water). In each method, the product can be "cleaned" (e.g., using one or more of the above-described techniques, e.g., dissolution, resuspension, and/or re-precipitation) to remove unreacted bromocriptine or citrate. Water may be removed by fractional distillation or other standard dewatering techniques known to those skilled in the art.

Further, bromocriptine citrate provides for pharmaceutical preparations with much greater water solubility (about 7-fold greater) than would be expected versus bromocriptine mesylate and therefore also more efficient absorption across biological cellular membranes relative to bromocriptine mesylate. Still further, due to the unexpectedly improved degradation resistance of bromocriptine citrate to water (e.g., in a physiological environment) and its simultaneously increased aqueous solubility (a phenomenon not predicted by the art) relative to bromocriptine mesylate, minimum and preferred dosages of bromocriptine citrate for treating vertebrates are lower than the minimum and preferred dosages of bromocriptine mesylate for an equivalent therapeutic effect and treatment duration. Taken together, the unanticipated advantages of bromocriptine citrate provide for a substantial improvement over the use of bromocriptine mesylate in current commercial bromocriptine pharmaceutical preparations 5 (e.g., CYCLOSET® or PARLODEL®), providing a more stable, more efficient and more biologically compatible and useful compound, with more predictable and reproducible effects, for pharmaceutical preparations of bromocriptine for the treatment of any of a variety of medical disorders including prediabetes, obesity, insulin resistance, hyperinsulinemia, hyperglycemia, cardiovascular disease, and type 2 diabetes mellitus (T2DM). Due to its increased solubility in water, bromocriptine citrate displays increased absorption in vivo as compared to bromocriptine mesylate. The enhanced physical and biological properties of pharmaceutical preparations of bromocriptine citrate cannot be mimicked by the mere addition of citrate to pharmaceutical preparations of bromocriptine mesylate. Moreover, the incorporation of bromocriptine citrate into a pharmaceutical formulation that contains acidic compounds such as fatty acid combined with citric acid enhances the stability of the bromocriptine which is unexpected and counterintuitive inasmuch as bromocriptine stability is hindered in an acidic environment. Substituting magnesium stearate with stearic acid surprisingly enhances the stability of the bromocriptine molecule, especially in the presence of the acid, citric acid. This stability is further enhanced by the removal or exclusion of lactose and its replacement with mannitol. Additionally, the stability of the bromocriptine citrate can be further enhanced by the presence of triglyceride in the formulation without alteration of its water solubility. This is surprising in that lubricants such as triglyceride do not have a known use to enhance stability of bromocriptine and are known to be hydrophobic not hydrophilic.

The resulting formulation of (i) bromocriptine citrate, (ii) a non-lactose short chain saccharide such as mannitol (ii) stearic acid or a triglyceride, and (iv) citric acid produces a unique and unexpected bromocriptine formulation that is both highly water soluble, a circumstance not true for bromocriptine or bromocriptine mesylate, and yet stable in water, an environment that normally destroys bromocriptine and bromocriptine mesylate, and such is accomplished in part by adding certain acidic excipients together with other certain excipients and a particular salt of bromocriptine. Bromocriptine citrate may be administered, with or without a dopamine $D_1$ receptor agonist such as SKF-38393, SKF-82958 or SKF-82957 to treat one or more of the metabolic disorders associated with MS, including, e.g., T2DM, hypertension, hypertriglyceridemia, a pro-inflammatory state, insulin resistance, fatty liver, NASH, CVD, and/or obesity. Bromocriptine citrate may further optionally be administered in conjunction with one or more agents that increase central dopaminergic neuronal activity or decrease central noradrenergic neuronal activity. Examples of such agents are known in the art and are disclosed in, e.g., U.S. Pat. Nos. 5,877,183 and 9,655,865 Bromocriptine citrate may still further optionally be administered in conjunction with various peripheral acting agents, e.g., HMGCoA reductase inhibitors, anti-hypertensives, anti-diabetes agents including, e.g., postprandial insulin secretagogues or insulin itself, anti-inflammatory agents, and anti-coagulative agents. Examples of such agents are known in the art and are disclosed in, e.g., Int'l. Pat. App. Pub. No. WO 2009/091576 A2.

Bromocriptine citrate is administered to the vertebrate animal or human, preferably orally or sublingually, optionally parenterally, for the treatment of any one or more symptoms desirable of change, e.g., obesity or hyperglycemia.

The solid pharmaceutical compositions of the invention should include an amount of the compound(s) of the invention effective for treatment of metabolic diseases and disorders such as, but not limited to, T2DM, obesity, prediabetes, Metabolic Syndrome, cardiometabolic risk, hypertension, dyslipidemia, insulin resistance, hyperinsulinemia, hepatic steatosis, renal disease, cardiovascular disease, cerebrovascular disease, and peripheral vascular disease and biomarkers of impending vascular disease and key elements thereof such as arteriosclerosis, coronary artery disease, peripheral vascular disease, or cerebrovascular disease), congestive heart failure, obesity, elevated plasma norepinephrine, elevated cardiovascular-related inflammatory factors, hyperlipoproteinemia, atherosclerosis, hyperphagia, hyperglycemia, hyperlipidemia, and hypertension or high blood pressure, increased plasma postprandial triglyceride or free fatty acid levels, increased cellular oxidative stress or plasma indicators thereof, increased circulating hypercoagulative state, renal disease including renal insufficiency. The effective dosage will depend on the severity of the diseases and the activity of the particular compound(s) employed, and is thus within the ordinary skill of the art to determine for any particular host mammal or other host organism. Suitable dosages of bromocriptine citrate for a vertebrate (e.g., a human) may be, e.g., in the range of about 0.05 µg to about 0.5 mg per kg BW, optionally in the range of about 0.1 µg to about 0.3 µg per kg BW or in one preferred embodiment between about 2 µg and mg/kg, 8W per day. A suitable pharmaceutical dosage form comprising bromocriptine citrate may have a total weight of, e.g., (including excipients) of between about 2.5 mg and about 2000 mg.

In one aspect, the present disclosure describes that in the preparation of bromocriptine formulations for improving glycemic control and treating type 2 diabetes, it has been discovered including certain excipients in the formulations may improve the stability of the bromocriptine. The present disclosure therefore describes bromocriptine pharmaceutical formulations with improved stability and bromocriptine pharmaceutical formulations that include an excipient that improves the stability of the bromocriptine in the formulation.

The bromocriptine pharmaceutical formulations are manufactured to have a uniform content, such that the bromocriptine is uniformly distributed within an ingredient blend that is compressed to form pharmaceutical formulations, and each pharmaceutical formulation contains substantially the same amount of bromocriptine and, as a result, provides substantially the same dose of bromocriptine to the patient. This property is desirable so that bromocriptine pharmaceutical formulations provide consistent efficacy, by ensuring that each pharmaceutical formulation provides an efficacious amount of bromocriptine, but also does not provide too high a dose of bromocriptine which may lead to side effects.

The mode of action involved in using bromocriptine to improve glycemic control and treating type 2 diabetes presents challenges in developing and manufacturing formulations that are suitable for this purpose. Many drugs work best when the pharmacological action of the drug (e.g., blocking a receptor or inhibiting an enzyme) is maintained throughout the period of treatment. While not being limited by theory, results from preclinical studies suggest that appropriately timed daily administration of bromocriptine in the morning normalizes aberrant hypothalamic neurotransmitter activities that induce, potentiate, and maintain the insulin-resistant, glucose-intolerant state.

Thus, it is believed that a formulation of bromocriptine manufactured to improve glycemic control and treat type 2 diabetes should provide a consistent, rapid and substantially complete release of the bromocriptine from the formulation to provide the optimum pharmacokinetic profile for treating diabetes. For example, while not being limited by theory, it is understood that bromocriptine for improving glycemic control should be formulated in a pharmaceutical formulation that provides a dose of at least about 0.1 mg of bromocriptine and which releases at least about 80%, or preferably at least about 90%, of the bromocriptine within about 30 minutes. Drug release can be measured, e.g., using the methods and apparatus described in the U.S. Pharmacopoeia (USP), General Chapter 711, Dissolution, 34$^{th}$ Edition, 2011. A suitable method for measuring release of bromocriptine from the pharmaceutical formulations described in the present disclosure can use USP Apparatus Type 2 Paddle Method at 50 rpm in 500 ml of 0.1 N hydrochloric acid. The dissolution experiment is typically carried out at about 37° C. A bromocriptine citrate product as described herein can be manufactured that consistently provides the specified dose and release profile, the resulting product may be less effective for improving metabolic disorders including key elements thereof including but not limited to, type 2 diabetes, prediabetes (impaired fasting glucose or impaired glucose tolerance), metabolic syndrome or indices (key elements) thereof (increased waist circumference, increased fasting plasma glucose, increased fasting plasma triglycerides, decreased fasting high density lipoprotein level, increased blood pressure), insulin resistance, hyperinsulinemia, cardiovascular disease (or key elements thereof such as arteriosclerosis, coronary artery disease, peripheral vascular disease, or cerebrovascular disease), congestive heart failure, obesity, elevated plasma norepinephrine, elevated cardiovascular-related inflammatory factors, hyperlipoproteinemia, atherosclerosis, hyperphagia, hyperglycemia, hyperlipidemia, and hypertension or high blood pressure, increased plasma postprandial triglyceride or free fatty acid levels, increased cellular oxidative stress or plasma indicators thereof, increased circulating hypercoagulative state, renal disease including renal insufficiency (all of which can be treated with the formulations disclosed herein).

In addition to providing a suitable consistent release profile, another important aspect of manufacturing a safe and effective bromocriptine formulation is that the bromocriptine in the formulation must be stable over a prolonged period so that the formulation provides a consistent therapeutic dose of bromocriptine as well as avoiding possible side effects from the presence of bromocriptine degradation products that do not provide therapeutic benefit. The degradation of bromocriptine to bromocriptinine, with or without the concurrent formation of a browning reaction (i.e., degradation-associated browning of the white pharmaceutical formulation and/or powdered excipients), represent major degradants of bromocriptine formulations with magnesium stearate and lactose that both occur at increased levels under stress conditions (i.e., conditions with higher heat and/or humidity relative to normal bromocriptine storage conditions, e.g., a temperature of 25±2° C. and a relative humidity of about 60±5%).

Without wishing to be bound by theory, a possible facilitator of the browning reaction and bromocriptinine production is the interaction of bromocriptine with lactose when in the presence of an alkaline environment (e.g., an environment caused by the presence of alkaline magnesium stearate [Mg stearate] or in the presence of magnesium). Such an interaction can result in a general base-catalyzed reaction of lactose. Alternately or in addition, Mg stearate can interact directly with bromocriptine (either in the presence or absence of lactose) to catalyze its isomerization to bromocriptinine. Bromocriptinine itself can also potentially participate in a browning reaction with lactose. Surprisingly, Mg interaction with lactose in the presence of bromocriptine can be expected to facilitate a degradative browning reaction (see FIG. 2). That is to say, the magnesium and not the magnesium stearate, especially in the presence of lactose, can be particularly damaging to bromocriptine. Any or all of the above degradative reactions can be accelerated by increased heat and/or humidity, e.g., higher heat and/or humidity relative to normal bromocriptine storage conditions. Any or all of the above reactions can be accelerated by increased pH, e.g., increased pH caused by the presence of one or more impurities in a bromocriptine formulation. As such, it is counterintuitive to add acidic compounds together in combination with bromocriptine in a pharmaceutical formulation to enhance bromocriptine stability. It is further counterintuitive to add compounds such as lubricants to enhance stability of bromocriptine that are not generally accepted as having this function.

As shown in Example 4, various bromocriptine formulations were studied to investigate the effects of reducing or eliminating Mg stearate and/or lactose from the presence of bromocriptine mesylate in the browning reaction. It was found that reducing or removing Mg stearate, lactose, or both Mg stearate and lactose from the bromocriptine mesylate formulation decreased the rate of degradation of bromocriptine to bromocriptinine and the rate of formation of the browning reaction. Removing both Mg stearate and lactose decreased the rate of formation of the browning reaction to the greatest extent (relative to removing only Mg stearate or removing only lactose). Furthermore, Mg stearate can be replaced with one or more acidic compounds, e.g., stearic acid, or one or more non-magnesium salt glidants (e.g., solid castor oil) to decrease the rate of degradation of bromocriptine and the rate of formation of the browning reaction. Alternately or in addition to the above-described bromocriptine formulation alterations, lactose can be replaced with mannitol and/or one or more other short chain saccharides to decrease the rate of degradation of bromocriptine and the rate of formation of the browning reaction. Alternately or in addition, one or more acidic compounds, e.g., citric acid or stearic acid, can be added to a bromocriptine formulation of mannitol to decrease the rate of degradation of bromocriptine and the rate of formation of the browning reaction. Again, this particular degradative reaction of bromocriptine is counterintuitively reduced by adding acids to the formulation, an interaction normally known to destroy bromocriptine.

An accelerated release formulation of bromocriptine mesylate was described in U.S. Pat. No. 5,679,685, which discusses that accelerated release from bromocriptine mesylate formulations could be achieved by formulating bromocriptine, an antioxidant, a filler, a disintegrant, a water scavenging agent and a lubricant. In the preferred formulation, the bromocriptine formulation included bromocriptine mesylate together with citric acid, corn starch, non-lactose filler, silicon dioxide and magnesium stearate. Use of an anhydrous filler is preferred to minimize moisture content. Citric acid is an antioxidant. Corn starch is a disintegrant. Colloidal silicone dioxide acts as a water-scavenger. Magnesium stearate acts as a lubricant.

While the '685 patent describes the preparation of rapid release bromocriptine mesylate on a laboratory scale, difficulties were encountered in manufacturing such a formulation on a large scale suitable for commercial use because a high degree of variation in the dissolution and rate of release of bromocriptine mesylate from the finished drug product, and problems in achieving acceptable product uniformity were found. Additionally, this formulation displays poor long term stability in storage under standard pharmaceutical conditions (25 C and 60% humidity) and worse stability at 40 C and 75% RH, and is very poorly water soluble and very labile to water degradation. It was found that that the manufacture of bromocriptine mesylate pharmaceutical formulations for improving glycemic control in patients with type 2 diabetes can be improved significantly by carefully controlling the size of the bromocriptine mesylate particles used in manufacturing the pharmaceutical formulations. By controlling the particle size, pharmaceutical formulations could be manufactured which consistently provide a release profile wherein about 90% or greater of the bromocriptine mesylate has been released at about 30 minutes or even within 20 minutes thereby ensuring that the product is produced with a consistently acceptable potency and safety profile for improving glycemic control and treating type 2 diabetes. This is particularly useful when a manufacturing method is employed that achieves improved content uniformity by employing direct transfer of the bromocriptine formulation mixture for, e.g., tableting after blending without allowing time for the ingredients to settle in the blended mixture. Advantages include the ability to reproducibly produce drug product with a defined drug content and drug release profile to meet quality standards mandated by drug regulatory authorities such as the Food and Drug Administration.

In particular, it is desirable to control the particle size of the bromocriptine used in bromocriptine pharmaceutical formulations for improving glycemic control in patients with type 2 diabetes so that the bromocriptine may have a Dv90 of about 20 µm or lower and thus the bromocriptine pharmaceutical formulations described herein can have a particular particle size distribution. In some embodiments, the bromocriptine used for manufacturing the pharmaceutical formulations may have a Dv90 of about 20 µm or lower, about 18 µm or lower, about 16 µm or lower, about 15 µm or lower, about 10 µm or lower, or about 5 µm or lower. In some embodiments, the bromocriptine used for manufacturing the pharmaceutical formulations may have a Dv99 of about 15 µm or lower, about 10 µm or lower, or about 5 µm or lower. In some embodiments, the bromocriptine used for manufacturing the pharmaceutical formulations may have a Dv50 of about 10 µm or lower, about 8 µm or lower, about 7 µm or lower, about 5 µm or lower, or about 2 µm or lower. In some embodiments, the bromocriptine used for manufacturing the pharmaceutical formulations may have a Dv10 of about 5 µm or lower, about 3 µm or lower, or about 2 µm or lower. In some embodiments, the bromocriptine used for manufacturing the pharmaceutical formulations may have a volume-based particle size distribution such that not more than about 40%, not more than about 20%, not more than 10% or not more than about 5% of the bromocriptine has a particle size of less than about 1 µm.

In some embodiments, the bromocriptine used for manufacturing the pharmaceutical formulations may have a particle size such that the particle size distribution has a Dv90 of about 20 µm or lower, a Dv50 of about 10 µm or lower and a Dv10 of about 5 µm or lower. In some embodiments, the bromocriptine used for manufacturing the pharmaceutical formulations may have a particle size such that the particle size distribution has a Dv90 of about 15 µm or lower, a Dv50 of about 8 µm or lower and a Dv10 of about 3 µm or lower. In some embodiments, the bromocriptine used for manufacturing the pharmaceutical formulations may have a particle size such that the particle size distribution has a Dv90 of about 10 µm or lower, a Dv50 of about 5 µm or lower and a Dv10 of about 3 µm or lower. In some embodiments, the bromocriptine used for manufacturing the pharmaceutical formulations may have a particle size such that the particle size distribution has a Dv90 of about 8 µm or lower, a Dv50 of about 5 µm or lower and a Dv10 of about 3 µm or lower. In some embodiments, the bromocriptine used for manufacturing the pharmaceutical formulations may have a particle size such that the particle size distribution has a Dv90 of about 5 µm or lower, a Dv50 of about 3 µm or lower and a Dv10 of about 1 µm or lower.

In some embodiments, the bromocriptine used for manufacturing the pharmaceutical formulations may have a volume-based particle size such that the particle size span is about 5 or lower, about 3 or lower, about 2.5 or lower, or about 2 or lower, or about 1.5 or lower.

In some embodiments the bromocriptine has a particle size diameter of 0.1 to 100 um.

In one embodiment the bromocriptine has an average particle size diameter between 0.5 and 3.0 µm.

By using bromocriptine with controlled particle size, bromocriptine pharmaceutical formulations can be manufactured that consistently provide drug release profiles that are effective for improving glycemic control and treating type 2 diabetes.

The bromocriptine pharmaceutical formulation prepared using bromocriptine having controlled particle size is formulated to provide a dissolution profile such that, when tested in USP Apparatus Type 2 paddle method at 50 rpm in 500 ml of 0.1 N hydrochloric acid at about 37° C., the pharmaceutical formulation has released at least about 80%, preferably at least about 90% of the bromocriptine at about 30 minutes. In some embodiments, the bromocriptine pharmaceutical formulation provides a dissolution profile such that the pharmaceutical formulation has released at least about 95% of the bromocriptine at about 30 minutes. In some embodiments, the bromocriptine pharmaceutical formulation provides a dissolution profile such that the pharmaceutical formulation has released at least about 80%, or at least about 90%, of the bromocriptine at about 20 minutes. Although the bromocriptine pharmaceutical formulation is formulated to provide a dissolution profile such that, when tested in USP Apparatus Type 2 paddle method at 50 rpm in 500 ml of 0.1 N hydrochloric acid at about 37° C., the pharmaceutical formulation has released at least about 80%, preferably about 90%, of the bromocriptine at about 30 minutes, extremely rapid release of bromocriptine from the formulation may not be desired, since a formulation that releases bromocriptine extremely rapidly may result in an undesired spike in in vivo drug levels and may not be suitable for treating type 2 diabetes, or give rise to side-effects. Therefore, in some embodiments, the bromocriptine pharmaceutical formulation prepared using micronized bromocriptine is formulated to provide a dissolution profile such that, when tested in USP Apparatus Type 2 paddle method at 50 rpm in 500 ml of 0.1 N hydrochloric acid at about 37° C., not more than about 75%, not more than about 60%, or not more than about 50% of the bromocriptine has been released at about 7 minutes, and/or not more than about 90%, not more than about 85%, not more than about 80%, or, not more than about 75% of the bromocriptine has been released at about 10 minutes. The release profiles may be achieved by producing bromocriptine pharmaceutical formulations using bromocriptine having a particular particle size distribution so that the finished drug product consistently provides a dissolution profile that is suitable for treatment of type 2 diabetes.

The bromocriptine pharmaceutical formulation prepared using bromocriptine having controlled particle size is formulated to provide a pharmacokinetic profile wherein the time to maximum plasma concentration ($T_{max}$) following administration of bromocriptine pharmaceutical formulations, (e.g., administration of six bromocriptine pharmaceutical formulations each providing a dose of about 0.8 mg of bromocriptine), is between about 30 and about 60 minutes, such as about 50 minutes, e.g., about 53 minutes, when the pharmaceutical formulations are administered under fasting conditions, or between about 90 and about 120 minutes, when the pharmaceutical formulations are administered under high fat fed conditions, to adult subjects.

The bromocriptine pharmaceutical formulation may contain an amount of bromocriptine e.g. bromocriptine citrate that provides a dose of at least about 0.1 mg of bromocriptine per pharmaceutical formulation, or, e.g., about 0.8 mg per pharmaceutical formulation. The bromocriptine pharmaceutical formulation may contain an amount of bromocriptine that provides a dose per pharmaceutical formulation of bromocriptine of, e.g., about 0.8 ma, about 1.6 mg, about 2.4 mg, about 3.2 mg, about 4.0 mg, about 4.8 mg, about 5.6 mg, about 6.4 mg, about 7.2 mg, about 8.0 mg, about 8.8 mg, or about 9.6 mg.

In some embodiments, the particle size may be controlled by use of micronized bromocriptine. It has been discovered that a superior bromocriptine formulation for improving glycemic control and treating type 2 diabetes can be prepared by using micronized bromocriptine for manufacturing bromocriptine pharmaceutical formulations. The micronized bromocriptine may have Dv99, Dv90, Dv50, Dv10, span and other properties of the particle size distribution with the values described above, including any embodiment thereof, or combination thereof. The pharmaceutical formulations manufactured using the micronized bromocriptine may have any of the dissolution profiles described above as being effective for improving glycemic control and treating type 2 diabetes, including any embodiment thereof or combination thereof. In addition, the formulation manufactured using micronized bromocriptine may provide a pharmacokinetic profile as described above and may contain an amount of bromocriptine as described above.

Micronization provides for reduction of particle size to provide particles that are on the order of microns in diameter as measured by methods known to those of ordinary skill in the art, such as the volume distribution method. Methods of micronizing bromocriptine to afford formulations disclosed herein include those that are known to those of ordinary skill in the art and include, but are not limited to, milling, grinding, and the use of supercritical fluids. For example, one method of micronization (the "rapid expansion of supercritical solutions" or RESS method), material is dissolved in supercritical fluid under high temperature and pressure and the resulting solution is expanded through a nozzle to form small particles.

Micronization by jet milling is a method that can be used to produce particles in the lower micrometer range, and is the preferred method for micronizing bromocriptine. In brief, the raw material with a maximum size of about 1 to 2 mm is introduced into the milling chamber via a gas stream. Within the milling chamber a circular gas stream accelerates the particles which are micronized by collision with each other or with the wall of the chamber. The ground particles are removed from the milling chamber by the gas stream, while the larger ones stay inside due to centrifugal forces. In the preferred process for micronizing bromocriptine, micronization is performed using a jet mill under a nitrogen atmosphere at a controlled temperature of about 0° C. However, reducing the particle size of bromocriptine as described above also very significantly increases the instability of the bromocriptine. Consequently, new methods need to be developed that can preserve the stability of micronized bromocriptine while also making it much more water soluble, an environment that destroys bromocriptine. It has surprisingly been found that including certain excipients traditionally used as lubricants in the bromocriptine formulation can improve the stability of the pharmaceutical formulation. Moreover, it has surprisingly been found that excluding certain excipients to be used as lubricants (e.g., magnesium stearate) or as fillers/disintegrants (e.g., lactose) in the bromocriptine formulation can improve the stability of the pharmaceutical formulation of micronized bromocriptine. Lubricants are agents that are added, usually in small quantities, to a pharmaceutical formulation and capsule formulations to improve certain processing characteristics. The lubricants serve to decrease friction at the interface between a pharmaceutical formulation and a die wall during formation of the pharmaceutical formulation to assist with, e.g., allowing the pharmaceutical formulation to be ejected from a die and reduce wear on punches and dies. In addition, the lubricants can serve an anti-adherent role, e.g., preventing the pharmaceutical formulation from sticking to punch faces or capsule-filling equipment. Lubricants can also serve a glidant role, e.g., enhancing product flow by reducing inter particulate friction. Lubricants, particularly acidic lubricants, are not typically used to reduce degradation reactions of agents such as bromocriptine. The excipients or lubricants that are effective for improving the stability of micronized bromocriptine pharmaceutical formulations as described herein comprise a triglyceride or a free fatty acid. The triglycerides can have fatty acid acyl groups with from 6 to 14 carbon atoms ($C_6$-$C_{14}$ fatty acids), 14 to 26 carbon atoms ($C_{14}$-$C_{26}$ fatty acids), from 14 to 24 carbon atoms ($C_{14}$-$C_{24}$ fatty acids), from 14 to 22 carbon atoms ($C_{14}$-$C_{22}$ fatty acids), from 14 to 20 carbon atoms ($C_{14}$-$C_{20}$ fatty acids), from 14 to 18 carbon atoms ($C_{14}$-$C_{18}$ fatty acids), from 16 to 24 carbon atoms ($C_{16}$-$C_{24}$ fatty acids), from 16 to 22 carbon atoms ($C_{16}$-$C_{22}$ fatty acids), from 16 to 20 carbon atoms ($C_{16}$-$C_{20}$ fatty acids), from 16 to 18 carbon atoms ($C_{16}$-$C_{18}$ fatty acids), from 18 to 24 carbon atoms ($C_{18}$-$C_{24}$ fatty acids), from 18 to 22 carbon atoms ($C_{18}$-$C_{22}$ fatty acids) or from 18 to 20 carbon atoms ($C_{18}$-$C_{20}$ fatty acids). In some embodiments, at least about 80%, at least about 85%, at least about 90%, at least about 95%, at least about 98% or at least about 99% of the acyl groups of the triglyceride can be fatty acid acyl groups of $C_{14}$-$C_{26}$ fatty acids. In some embodiments, at least about 80%, at least about 85%, at least about 90%, at least about 95%, at least about 98% or at least about 99% of the acyl groups of the triglyceride can be fatty acid acyl groups of $C_6$-$C_{14}$ fatty acids. In some embodiments, at least about 80%, at least about 85%, at least about 90%, at least about 95%, at least about 98% or at least about 99% of the acyl groups of the triglyceride can be fatty acid acyl groups of $C_{14}$-$C_{24}$ fatty acids. In some embodiments, at least about 80%, at least about 85%, at least about 90%, at least about 95%, at least about 98% or at least about 99% of the acyl groups of the triglyceride can be fatty acid acyl groups of $C_{14}$-$C_{22}$ fatty acids. In some embodiments, at least about 80%, at least about 85%, at least about 90%, at least about 95%, at least about 98% or at least about 99% of the acyl groups of the triglyceride can be fatty acid acyl groups of $C_{14}$-$C_{20}$ fatty acids. In some embodiments, at least about 80%, at least about 85%, at least about 90%, at least about 95%, at least about 98% or at least about 99% of the acyl groups of the triglyceride can be fatty acid acyl groups of $C_{14}$-$C_{18}$ fatty acids. In some embodiments, at least about 80%, at least about 85%, at least about 90%, at least about 95%, at least about 98% or at least about 99% of the acyl groups of the triglyceride can be fatty acid acyl groups of $C_{16}$-$C_{26}$ fatty acids. In some embodiments, at least about 80%, at least about 85%, at least about 90%, at least about 95%, at least about 98% or at least about 99% of the acyl groups of the triglyceride can be fatty acid acyl groups of $C_{16}$-$C_{24}$ fatty acids. In some embodiments, least about 80%, at least about 85%, at least about 90%, at least about 95%, at least about 98% or at least about 99% of the acyl groups of the triglyceride can be fatty acid acyl groups of $C_{16}$-$C_{22}$ fatty acids. In some embodiments, at least about 80%, at least about 85%, at least about 90%, at least about 95%, at least about 98% or at least about 99% of the acyl groups of the triglyceride can be fatty acid acyl groups of $C_{16}$-$C_{20}$ fatty acids. In some embodiments, at least about 80%, at least about 85%, at least about 90%, at least about 95%, at least about 98% or at least about 99% of the acyl groups of the triglyceride can be fatty acid acyl groups of $C_{16}$-$C_{18}$ fatty acids. In some embodiments, at least about 80%, at least about 85%, at least about 90%, at least about 95%, at least about 98% or at least about 99% of the acyl groups of the triglyceride can be fatty acid acyl groups of $C_{18}$-$C_{26}$ fatty acids. In some embodiments, at least about 80%, at least about 85%, at least about 90%, at least about 95%, at least about 98% or at least about 99% of the acyl groups of the triglyceride can be fatty acid acyl groups of $C_{18}$-$C_{24}$ fatty acids. In some embodiments, at least about 80%, at least about 85%, at least about 90%, at least about 95%, at least about 98% or at least about 99% of the acyl groups of the triglyceride can be fatty acid acyl groups of $C_{18}$-$C_{22}$ fatty acids. In some embodiments, at least about 80%, at least about 85%, at least about 90%, at least about 95%, at least about 98% or at least about 99% of the acyl groups of the triglyceride can be fatty acid acyl groups of $C_{18}$-$C_{20}$ fatty acids. In some embodiments, at least about 80%, at least about 85%, at least about 90%, at least about 95%, at least about 98% or at least about 99% of the acyl groups of the triglyceride can be fatty acid acyl groups of $C_{18}$ fatty acids. In some embodiments, the acyl groups of the triglyceride can be fatty acid acyl groups of saturated fatty acids. In some embodiments, at least about 80%, at least about 85%, at least about 90%, at least about 95%, at least about 98% or at least about 99% of the acyl groups of the triglyceride can be fatty acid acyl groups of saturated fatty acids. In some embodiments, at least about 80%, at least about 85%, at least about 90%, at least about 95%, at least about 98% or at least about 99% of the acyl groups of the triglyceride can be a stearoyl group or a 12-hydroxystearoyl group.

Examples of suitable excipients or lubricants include, without limitation, waxes, glycerides, vegetable oils and hydrogenated vegetable oils. Examples of vegetable oils include almond oil, apricot kernel oil, canola oil, castor oil, cinnamon oil, coconut oil, corn oil, cottonseed oil, flaxseed oil, palm oil, palm kernel oil, olive oil, peanut oil, rapeseed oil, safflower oil, soybean oil and sunflower oil and mixtures thereof. Examples of hydrogenated vegetable oils include hydrogenated castor oil (castor wax), hydrogenated coconut oil, hydrogenated cottonseed oil, hydrogenated palm oil, hydrogenated palm kernel oil, hydrogenated soybean oil and mixtures thereof. Examples of suitable excipients or lubricants include, without limitation, BBS (partially hydrogenated vegetable oil); BBS-C (partially hydrogenated vegetable oil); CASTORWAX® (hydrogenated castor oil), CASTORWAX® MP-70 (hydrogenated castor oil), CASTORWAX® MP-80 (hydrogenated castor oil), CENWAX®G (hydrogenated castor oil), CERIT™ SH (hydrogenated castor oil), CUTINA® HR (hydrogenated castor seed oil); HYDRO~KOTE® 112 (hydrogenated palm kernel oil); HYDRO~KOTE® C (hydrogenated cottonseed oil); HYDRO~KOTE® NI (hydrogenated palm kernel oil); HYDRO~KOTE® S (hydrogenated soybean oil); KOLLIWAX® HCO (hydrogenated castor oil), LUBRITAB® (hydrogenated cottonseed oil, STEROTEX® K (hydrogenated soybean oil and castor wax), STEROTEX® (hydrogenated cottonseed oil), STEROTEX® FL (hydrogenated soybean oil).

The lubricant, the formulation, or both can be substantially free of lactose.

The lubricant, the formulation, or both can be substantially free of magnesium. "Substantially free" in this context means magnesium ions may be present in the parts per million range (preferably less than about 10 ppm) and preferably not in the parts per hundred (percentage) range.

The lubricant contained in the pharmaceutical formulation may comprise less than about 0.75% by weight of magnesium stearate by weight compared to the total weight of the pharmaceutical formulation.

The excipient or lubricant used to stabilize the formulation can be used in an amount from about 0.1% to about 25% by weight. In some embodiments, the excipient or lubricant is used in an amount from about 0.5% to about 5% by weight. In some embodiments, the excipient or lubricant is used in an amount from about 1% to about 5% by weight. In some embodiments, the excipient or lubricant is used in an amount from about 1.5% to about 5% by weight. In some embodiments, the excipient or lubricant is used in an amount from about 2% to about 5% by weight. In some embodiments, the excipient or lubricant is used in an amount from about 0.1% to about 3% by weight. In some embodiments, the excipient or lubricant is used in an amount from about 0.5% to about 3% by weight. In some embodiments, the excipient or lubricant is used in an amount from about 1.5% to about 3% by weight. In some embodiments, the excipient or lubricant is used in an amount from about 2% to about 3% by weight. In some embodiments, the excipient or lubricant is used in an amount from about 0.5% to about 2.5% by weight. In some embodiments, the excipient or lubricant is used in an amount from about 0.5% to about 1.5% by weight. In some embodiments, the excipient or lubricant is used in an amount from about 1.5% to about 2.5% by weight. In some embodiments, the excipient or lubricant is used in an amount 30 of about 2% by weight.

In some embodiments, the excipient or lubricant is extragranular. The excipient or lubricant can be added after blending the remaining ingredients prior to, e.g., tableting.

The present application also describes pharmaceutical formulations comprising micronized bromocriptine that include, exclude or reduce the amounts of certain excipients in the pharmaceutical formulations can reduce the amount of related substances or impurities contained in the pharmaceutical formulations when they are stored under particular conditions over a period of time. In one aspect pharmaceutical formulations are provided comprising micronized bromocriptine and no magnesium stearate in the total weight of the pharmaceutical formulation. In a further aspect pharmaceutical formulations are provided comprising micronized bromocriptine and one or more lubricants selected from stearic acid, fatty acids, and at least one triglyceride, or combinations thereof. The triglyceride can be or have any of the properties of the triglyceride-containing lubricants or excipients described above.

Exemplary pharmaceutical formulations were prepared using micronized bromocriptine mesylate formulations with various lubricants (see, e.g., Example 6). The formulations had the compositions shown in Table 8. Formulation A was a control that used magnesium stearate (0.76% by weight) as a lubricant. Formulation B used stearic acid (2%) as a lubricant. Formulation C used sodium stearyl fumarate (2%) as a lubricant. Formulation D used hydrogenated castor oil (KOLLIWAX® HCO) (2%) as a lubricant. Finally, Formulation E used magnesium stearate as a lubricant (0.44%, a reduced amount compared to Formulation A). Each pharmaceutical formulation was then stored at 25±2° C. and 60±5% RH, at 30±2° C. and 65±5% RH, or at 40±2° C. and 75±5% RF for up to 3 months and analyzed for related substance impurities at the beginning of the experiment and at 1, 2, and/or 3 months. The results shown in Table 9 and FIGS. 1A, 1B, and 1C indicate that the formulation using hydrogenated castor oil as a lubricant was significantly more stable, forming smaller amounts of related substance impurities, than any of the other formulations. Formulations which used sodium stearyl fumarate or less than about 0.75% by weight of magnesium stearate compared to the total weight of the pharmaceutical formulation were also more stable, forming smaller amounts of related substance impurities, relative to the control Formulation A. In addition, the dissolution of Formulations A and C-E was tested both before and after storage at 25±2° C. and 60±5% RH for 3 months with the results, shown in Table 10, demonstrating that the lubricants described above had no significant effect on dissolution for any of the formulations before or after storage.

The formulations that include excipients or lubricants that stabilize the formulation as described above can be prepared using bromocriptine of controlled particle size may have Dv99, Dv90, Dv50, Dv10, span and other properties of the particle size distribution with the values described above, including any embodiment thereof, or combination thereof. The bromocriptine particle size can be controlled by micronization or any of the other methods described above. The pharmaceutical formulations manufactured using the bromocriptine of controlled particle size and a diluent may have any of the dissolution profiles described above as being effective for improving metabolic disorders or key elements thereof such as dysglycemic control and type 2 diabetes, including any embodiment thereof or combination thereof. In addition, the formulation manufactured using excipients or lubricants that stabilize the formulation as described above may provide a pharmacokinetic profile as described above and may contain an amount of bromocriptine as described above.

In another aspect, the present disclosure provides bromocriptine pharmaceutical formulations containing micronized bromocriptine that have enhanced stability. The stability of the pharmaceutical formulation can be such that the pharmaceutical formulation contains no more than 8% total related substances following storage of the pharmaceutical formulation at a temperature of 25±2° C. at about 60±5% relative humidity for about 18 months. In some embodiments, stability of the pharmaceutical formulation can be such that the pharmaceutical formulation contains no more than 8% total related substances following storage of the pharmaceutical formulation at a temperature of 25±2° C. at about 60±5% relative humidity for about 24 months. In some embodiments, stability of the pharmaceutical formulation can be such that the pharmaceutical formulation contains no more than 8% total related substances following storage of the pharmaceutical formulation at a temperature of 25±2° C. at about 60±5% relative humidity for about 36 months. In some embodiments, stability of the pharmaceutical formulation can be such that the pharmaceutical formulation contains no more than 8% total related substances following storage of the pharmaceutical formulation at a temperature of 25±2° C. at about 60±5% relative humidity for about 48 months. The stability of the pharmaceutical formulation can be such that the pharmaceutical formulation contains no more than 8% of bromocriptinine following storage of the pharmaceutical formulation at a temperature of 25±2° C. at about 60±5% relative humidity for about 18 months. In some embodiments, stability of the pharmaceutical formulation can be such that the pharmaceutical formulation contains no more than 8% of bromocriptinine following storage of the pharmaceutical formulation at a temperature of 25±2° C. at about 60±5% relative humidity for about 24 months. In some embodiments, stability of the pharmaceutical formulation can be such that the pharmaceutical formulation contains no more than 8% of bromocriptinine following storage of the pharmaceutical formulation at a temperature of 25±2° C. at about 60±5% relative humidity for about 36 months. In some embodiments, stability of the pharmaceutical formulation can be such that the pharmaceutical formulation contains no more than 8% of bromocriptinine following storage of the pharmaceutical formulation at a temperature of 25±2° C. at about 60±5% relative humidity for about 48 months. The stability of the pharmaceutical formulation can be such that the pharmaceutical formulation contains no more than 5% total related substances following storage of the pharmaceutical formulation at a temperature of 25±2° C. at about 60±5% relative humidity for about 18 months. In some embodiments, stability of the pharmaceutical formulation can be such that the pharmaceutical formulation contains no more than 5% total related substances following storage of the pharmaceutical formulation at a temperature of 25±2° C. at about 60±5% relative humidity for about 24 months. In some embodiments, stability of the pharmaceutical formulation can be such that the pharmaceutical formulation contains no more than 5% total related substances following storage of the pharmaceutical formulation at a temperature of 25±2° C. at about 60±5% relative humidity for about 36 months. In some embodiments, stability of the pharmaceutical formulation can be such that the pharmaceutical formulation contains no more than 5% total related substances following storage of the pharmaceutical formulation at a temperature of 25±2° C. at about 60±5% relative humidity for about 48 months. The stability of the pharmaceutical formulation can be such that the pharmaceutical formulation contains no more than 5% of bromocriptinine following storage of the pharmaceutical formulation at a temperature of 25±2° C. at about 60±5% relative humidity for about 18 months. The stability of the pharmaceutical formulation can be such that the pharmaceutical formulation contains no more than 3% of bromocriptinine following storage of the pharmaceutical formulation at a temperature of 25±2° C. at about 60±5% relative humidity for about 18 months. In some embodiments, stability of the pharmaceutical formulation can be such that the pharmaceutical formulation contains no more than 5% of bromocriptinine following storage of the pharmaceutical formulation at a temperature of 25±2° C. at about 60±5% relative humidity for about 24 months. In some embodiments, stability of the pharmaceutical formulation can be such that the pharmaceutical formulation contains no more than 5% of bromocriptinine following storage of the pharmaceutical formulation at a temperature of 25±2° C. at about 60±5% relative humidity for about 36 months. In some embodiments, stability of the pharmaceutical formulation can be such that the pharmaceutical formulation contains no more than 5% of bromocriptinine following storage of the pharmaceutical formulation at a temperature of 25±2° C. at about 60±5% relative humidity for about 48 months. The stability of the pharmaceutical formulation can be such that the pharmaceutical formulation contains no more than 3% total related substances following storage of the pharmaceutical formulation at a temperature of 25±2° C. at about 60±5% relative humidity for about 18 months. In some embodiments, stability of the pharmaceutical formulation can be such that the pharmaceutical formulation contains no more than 3% total related substances following storage of the pharmaceutical formulation at a temperature of 25±2° C. at about 60±5% relative humidity for about 24 months. In some embodiments, stability of the pharmaceutical formulation can be such that the pharmaceutical formulation contains no more than 3% total related substances following storage of the pharmaceutical formulation at a temperature of 25±2° C. at about 60±5% relative humidity for about 36 months. In some embodiments, stability of the pharmaceutical formulation can be such that the pharmaceutical formulation contains no more than 3% total related substances following storage of the pharmaceutical formulation at a temperature of 25±2° C. at about 60±5% relative humidity for about 48 months. In some embodiments, the stability of the pharmaceutical formulation can be such that the pharmaceutical formulation contains no more than 3% of bromocriptinine following storage of the pharmaceutical formulation at a temperature of 25±2° C. at about 60±5% relative humidity for about 18 months. In some embodiments, stability of the pharmaceutical formulation can be such that the pharmaceutical formulation contains no more than 3% of bromocriptinine following storage of the pharmaceutical formulation at a temperature of 25±2° C. at about 60±5% relative humidity for about 24 months. In some embodiments, stability of the pharmaceutical formulation can be such that the pharmaceutical formulation contains no more than 3% of bromocriptinine following storage of the pharmaceutical formulation at a temperature of 25±2° C. at about 60±5% relative humidity for about 36 months. In some embodiments, stability of the pharmaceutical formulation can be such that the pharmaceutical formulation contains no more than 3% of bromocriptinine following storage of the pharmaceutical formulation at a temperature of 25±2° C. at about 60±5% relative humidity for about 48 months.

The amount of total related substances or the amount of bromocriptine is determined by HPLC analysis using detection of UV absorption at 300 nm.

In some embodiments, the pharmaceutical formulation is stable such that the pharmaceutical formulation contains no more than 1% total related substances as determined by HPLC analysis using detection of UV absorption at 300 nm following storage of the pharmaceutical formulation at a temperature of 40±2° C. at about 70±5% relative humidity for about 6 weeks.

In some embodiments, the pharmaceutical formulation is stable such that the pharmaceutical formulation contains no more than 8% total related substances as determined by HPLC analysis using detection of UV absorption at 300 nm following storage of the pharmaceutical formulation at a temperature of 40±2° C. at about 70±5% relative humidity for about 6 months.

In some embodiments, the pharmaceutical formulation is stable such that the pharmaceutical formulation contains no more than 8% total related substances as determined by HPLC analysis using detection of UV absorption at 300 nm following storage of the pharmaceutical formulation at a temperature of 40±2° C. at about 70±5% relative humidity for at least 6 months.

In some embodiments, the pharmaceutical formulation is stable such that the pharmaceutical formulation contains no more than 8% total related substances as determined by HPLC analysis using detection of UV absorption at 300 nm following storage of the pharmaceutical formulation at a temperature of 40±2° C. at about 70±5% relative humidity for at least 12 months. The amount of total related substances or the amount of bromocriptine is determined by HPLC analysis using detection of UV absorption at 300 nm.

The formulations disclosed herein may also include permeation enhancing agents, bioadhesives, film forming agents, plasticizers, stabilizers, fillers and mucosal tissue irritant reducers, binders, disintegrants, lubricants and fillers.

Bioadhesives are included, for example, in adhesive tablets, solutions, colloidal suspensions, gels, ointments, patches, films, pastes, and lozenges. Examples of bioadhesives polymers include, without limitation, Klucel, Benecel® MP814, Kollidon, chitosan, cellulose derivatives, Carbopol 934P, Carbopol 974P, 1Voveou AA-1, carbopole resins, carbomer, xanthan gum, polycarbophil and polyethylene oxide combined with an inert diluent and an active ingredient, and ionic polysaccharides. Several synthetic and semi-synthetic bioadhesive polymers of different molecular weight and variations in degree of substitution include, without limitation, hydroxyethylcellulose, polyvinylalcohol, polyacrylic acid, sodium carboxymethyl cellulose, polyvinylpyrrolidone, polyethylene glycols and others. Mucosal adhesion of these bioadhesive formulations is based on the interpenetration of hydrated hydrocolloid chains of the bioadhesive formulation and glycoprotein chains of the oral mucosa.

Examples of suitable film forming agents include, but are not limited to, hydroxypropylmethylcellulose, ethylcellulose and polymethacrylates.

Examples of suitable plasticizers include, but are not limited to, polyethylene glycols of different molecular weights (e.g., 200-8000 Da), plant gums, and propylene glycol and triethyl citrate.

Examples of permeation enhancing agents include, without limitation, bile salts, fatty acids, fatty acid derivatives, surfactants, fatty acid esters, such as laureate, myristate and stearate monoesters of polyethylene glycol, enamine, derivatives and alpha-keto aldehydes; sodium cholate; sodium glycocholate; sodium deoxycholate; sodium lauryl sulfate; sodium salicylate; sodium ethylenediaminetetraacetic acid (EDTA); aprotinin; azone; sodium 5-methoxysalicylate; 1-oleylazacycloheptan-2-one; and/or silicas with a high affinity for aqueous solvents, such as the precipitated silica better known by the trade mark Syloid®, maltodextrins, ß-cyclodextrins, surfactants, chelators, cyclodextrins, chitosan, and lower alcohols.

Examples of stabilizers include, without limitation, citric acid, ascorbic acid, oleic acid, caprylic acid, capric acid, polyvinylpyrrolidone, waxes, block co-polymers, poloxamers, Poloxamer 188 and 407, poloxamines, Poloxamine 908, polyvinyl pyrrolidone, polyvinyl alcohol, gelatine, polysaccharide, hyaluronic acid, chitosan, derivatives of chitosan, polyacryl acid, derivatives of polyacryl acid, polycarbophil, cellulose derivatives, methyl cellulose, hydroxypropyl cellulose, carboxymethyl cellulose, sugar esters, saccharose monostearate, sodium citrate individually, fatty acids, fatty alcohols, alcohols, long chain fatty acid esters, long chain ethers, hydrophilic derivatives of fatty acids, polyvinylethers, polyvinyl alcohols, hydrocarbons, hydrophobic polymers, moisture-absorbing polymers, and combinations thereof.

Examples of anhydrous mucosal tissue irritant-reducing agent include, without limitation, plant oils like but not limited to olive oil, corn oil or mineral oil. Examples of fillers include, without limitation, microcellulose, e.g., Pro-Solv; Pharmaburst; Cab-o-sil; and saccharides, e.g., mannitol, lactose, xylitol and mixtures thereof.

Examples of suitable binders include, without limitation, either individually or in combination, such binding agents as sucrose, gelatin, glucose, starch, cellulose materials, polyethylene glycols, povidone, methylcellulose, sodium carboxymethylcellulose, sodium alginate, agar, alginic acid and salts of alginic acid, calcium carrageenan, magnesium aluminum silicate, polyethylene glycol, guar gum, polysaccharide acids, bentonites, polyvinylpyrrolidone (povidone), hydroxymethyl polyvinyl pyrolidone, polymethacrylates (such as Eudragit), methylcellulose, hydroxypropyl methylcellulose (HPMC), hydroxypropyl cellulose (Klucel™), ethyl cellulose (Ethocel™), hydroxypropylmethylcellulose, pregelatinized starch (such as National™ 1511 and Starch 1500), sucrose, lactose, starch paste, povidone polyethyleneglycol, Pullulan and corn syrup, waxes, and natural and synthetic gums, such as acacia, tragacanth, vegetable gum, castor oil, microcrystalline cellulose, dextrin, liquid glucose, guar gum, pectin, PEG, povidone, pregelatinized starch etc. Examples of suitable disintegrants include, without limitation, Klucel, starches such as maize starch and rice starch, cross-linked N-vinyl-2-pyrrolidone (CLPVP), alginic acid or alginates, microcrystalline cellulose, hydroxypropyl cellulose and other cellulose derivatives, croscarmellose sodium, crospovidone, polacrillin potassium, starch, pregelatinized starch, Pharmablast® carboxymethyl starch (e.g. Primogel® and Explotab® (sodium starch glycolate and sodium carboxymethyl starch)), sodium starch glycolate, and formaldehyde casein. Effervescent disintegrants include without limitation, for example, starch, potassiumbicarbonate, and sodium bicarbonate in combination with citric or tartaric acids. The disintegrant is present as an intra-granular disintegrant or extra-granular disintegrant.

Examples of suitable lubricants include, without limitation, sodium oleate, sodium stearate, sodium stearyl fumarate, stearic acid, magnesium stearate, sodium benzoate, sodium acetate, sodium chloride, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, and sodium acetate.

Examples of suitable flavoring agents include, without limitation, menthol, peppermint, vanilla, fruit flavorings, and sweeteners, e.g., aspartame or sodium saccharinate.

The formulations disclosed herein may further include citric acid as an excipient. Citric acid as an excipient may act to improve the stability of the bromocriptine citrate in water (counter to the known effect of bromocriptine to be degraded in acidic environments), and also may enhance bromocriptine solubility and absorption. Other agents used as antioxidants may include, but are not limited to, vitamins A, C, E, beta-carotene, zinc, selenium, glutathione, coenzyme Q-10 and *echinacea*. The citric acid or other antioxidant can be used in an amount from about 0.1% to about 5% by weight. In some embodiments, the citric acid or other antioxidant is used in an amount from about 0.5% to about 5% by weight. In some embodiments, the citric acid or other antioxidant is used in an amount from about 1% to about 5% by weight. In some embodiments, the citric acid or other antioxidant is used in an amount from about 0.5% to about 3% by weight. In some embodiments, the citric acid or other antioxidant is used in an amount from about 1% to about 2% by weight. In some embodiments, the citric acid or other antioxidant is used in an amount of about 1.5% by weight. Citric acid used in the formulations can be of a particle size such about 3% or less of said citric acid is greater than 600 μm when sieved and about 5% or greater of said citric acid is 150 μm or less when sieved.

The formulations disclosed herein may also include one or more (non-lactose) disintegrants. Examples of suitable disintegrants include, but are not limited to, starches such as corn starch, maize starch, pregelatinized starch, rice starch, sodium starch glycolate, and sodium carboxymethyl starch, alginic acid or alginates such as sodium alginate, croscarmellose sodium, crospovidone, cross-linked N-vinyl-2-pyrrolidone (CLPVP), cellulose derivatives such as sodium carboxymethyl cellulose, calcium carboxymethyl cellulose, polyvinylpyrrolidone, methyl cellulose, microcrystalline cellulose, and lower alkyl-substituted hydroxypropyl cellulose, formaldehyde casein, and polacrillin potassium. Effervescent disintegrants include without limitation, for example, starch, potassium bicarbonate, and sodium bicarbonate in combination with citric or tartaric acids. The disintegrant can be used in an amount from about 2% to about 50% by weight. In some embodiments, the disintegrant is used in an amount from about 5% to about 20% by weight. In some embodiments, the disintegrant is used in an amount from about 5% to about 15% by weight. In some embodiments, the disintegrant is used in an amount of about 10% by weight.

The formulations disclosed herein may also include one or more diluents such as short chain saccharides (e.g., monosaccharides or disaccharides, excluding lactose). Examples of such short chain saccharides include, but are not limited to, mannitol, xylitol, dextrose, maltose, sucrose, galactose, fructose, and sorbitol. In some embodiments, the diluent is used in an amount from about 60% to about 90% by weight. In some embodiments, the diluent is used in an amount from about 65% to about 90% by weight. In some embodiments, the diluent is used in an amount from about 70% to about 90% by weight. In some embodiments, diluent is used in an amount of about 85% by weight. The preferred formulation excludes lactose from the formulation.

In some embodiments, the pharmaceutical formulation may have a pharmacokinetic profile wherein the time to maximum plasma concentration ($T_{max}$) following administration of bromocriptine pharmaceutical formulations (e.g., six pharmaceutical formulations each providing a dose of about 0.8 mg of bromocriptine) is between about 30 and about 60 minutes, such as about 50 minutes, e.g., about 53 minutes, when the pharmaceutical formulations are administered under fasting conditions, or between about 90 and about 120 minutes, when the pharmaceutical formulations are administered under high fat fed conditions, to adult subjects.

The bromocriptine pharmaceutical formulations (e.g., tablets) described herein, and bromocriptine pharmaceutical formulations prepared by the methods herein, may be used to treat type 2 diabetes by improving glycemic control in an individual with type 2 diabetes. The pharmaceutical formulation may be administered within about two hours after waking in the morning with food. The initial dose may be about 0.1 mg of bromocriptine daily, which may be increased weekly until a maximal tolerated daily dose of about 1.6 to about 7.2 mg is achieved.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Therefore, in summary:

¶1. The present disclosure therefore provides a pharmaceutical formulation (e.g., a tablet) comprising bromocriptine (e.g., bromocriptine mesylate or a different bromocriptine salt, e.g., bromocriptine citrate) and an excipient; wherein the bromocriptine is present in an amount that provides a dose of at least about 0.1 mg of bromocriptine per pharmaceutical formulation; and wherein the excipient comprises a fatty acid or triglyceride. The excipient can be devoid of magnesium, magnesium stearate, and/or lactose. The excipient can include one or more non-lactose saccharides. Moreover, the present disclosure provides a pharmaceutical formulation of bromocriptine that is stable to heat and humidity and that has a water solubility of at least 500 mg/ml of water and that can be stable in an aqueous environment. Specifically, the present disclosure provides a pharmaceutical formulation comprising bromocriptine citrate, a free fatty acid such as stearic acid or triglyceride, a non-lactose saccharide such as mannitol, and citric acid as an excipient. The excipient can be devoid of magnesium or magnesium stearate. More specifically the present disclosure provides a pharmaceutical formulation of bromocriptine citrate, a free fatty acid such as stearic acid or a triglyceride, a non-lactose saccharide such as mannitol, and citric acid as an excipient wherein the bromocriptine formulation to stable to heat and humidity and wherein the bromocriptine formulation has a high water solubility (e.g., at least 200 mg/L or 500 mg/L solubility in water) and can be stable in an aqueous environment (minimal degradation at 25 C for 6 hours). More specifically yet, the present disclosure provides a pharmaceutical formulation comprising bromocriptine citrate, a free fatty acid such as stearic acid or a triglyceride, a non-lactose saccharide such as mannitol, and citric acid as an excipient wherein the bromocriptine formulation is more stable to heat and humidity and wherein the bromocriptine formulation has a much greater water solubility (e.g., at least 500 mg/L or at least 200 mg/L solubility in water) and can be more stable in an aqueous environment than a traditional pharmaceutical formulation comprising bromocriptine as the mesylate salt plus lactose, magnesium stearate, and citric acid as excipients.

¶2. The present disclosure provides a pharmaceutical formulation as described in ¶1, wherein at least about 80% of the acyl groups of the triglyceride are fatty acid acyl groups of $C_6$-$C_{14}$ fatty acids.

The present disclosure provides a pharmaceutical formulation as described in ¶1, wherein at least about 80% of the acyl groups of the triglyceride are fatty acid acyl groups of $C_{14}$-$C_{26}$ fatty acids.

¶3. The present disclosure provides a pharmaceutical formulation as described in paragraph ¶2, wherein at least about 90% of the acyl groups of the triglyceride are fatty acid acyl groups of $C_{14}$-$C_{26}$ fatty acids.

¶4. The present disclosure provides a pharmaceutical formulation as described in paragraph ¶2, wherein at least about 80% of the acyl groups of the triglyceride are fatty acid acyl groups of $C_{16}$-$C_{20}$ fatty acids.

¶5. The present disclosure provides a pharmaceutical formulation as described in paragraph ¶3, wherein at least about 90% of the acyl groups of the triglyceride are fatty acid acyl groups of $C_{16}$-$C_{20}$ fatty acids.

¶6. The present disclosure provides a pharmaceutical formulation as described in paragraph ¶4, wherein at least about 80% of the acyl groups of the triglyceride are fatty acid acyl groups of $C_{18}$ fatty acids. ¶7. The present disclosure provides a pharmaceutical formulation as described in paragraph ¶5, wherein at least about 90% of the acyl groups of the triglyceride are fatty acid acyl groups of $C_{18}$ fatty acids.

¶8. The present disclosure provides a pharmaceutical formulation as described in paragraph ¶6, wherein at least about 80% of the acyl groups of the triglyceride are stearoyl or 12-hydroxystearoyl groups.

¶9. The present disclosure provides a pharmaceutical formulation as described in paragraph ¶5, wherein at least about 90% of the acyl groups of the triglyceride are stearoyl or 12-hydroxystearoyl groups.

¶10. The present disclosure provides a pharmaceutical formulation as described in any one of paragraphs ¶1 to 9, wherein at least about 80% of the acyl groups of the triglyceride are saturated.

¶11. The present disclosure provides a pharmaceutical formulation as described in paragraph ¶10, wherein at least about 90% of the acyl groups of the triglyceride are saturated.

¶12. The present disclosure provides a pharmaceutical formulation as described in any one of paragraphs ¶1 to 11, wherein the excipient comprises a hydrogenated vegetable oil.

¶13. The present disclosure provides a pharmaceutical formulation as described in any one of paragraphs ¶1 to 12, wherein the excipient comprises hydrogenated castor oil, hydrogenated coconut oil, hydrogenated cottonseed oil, hydrogenated palm oil, hydrogenated palm kernel oil, hydrogenated soybean oil or a combination thereof.

¶14. The present disclosure provides a pharmaceutical formulation as described in any one of paragraphs ¶1 to 13, wherein the excipient comprises hydrogenated castor oil.

¶15. The present disclosure provides a pharmaceutical formulation as described in paragraphs ¶1 to 14, wherein the excipient comprises KOLLIWAX® HCO.

¶16. The present disclosure provides a pharmaceutical formulation as described in any one of paragraphs ¶1 to 15, wherein the excipient is present in an amount from about 0.5% to about 3% by weight of the formulation.

¶17. The present disclosure provides a pharmaceutical formulation as described in any one of paragraph ¶1 to 16, wherein the excipient is extragranular.

¶18. The present disclosure provides a pharmaceutical formulation as described in any one of paragraphs ¶1 to 17, wherein the pharmaceutical formulation is stable such that the formulation contains no more than 5% total related substances as determined by HPLC analysis using detection of UV absorption at 300 nm following storage of the formulation at a temperature of 25±2° C. at about 60±5% relative humidity for about 18 months.

¶19. The present disclosure provides a pharmaceutical formulation as described in paragraph ¶18, wherein the pharmaceutical formulation is stable such that the formulation contains no more than 5% total related substances as determined by HPLC analysis using detection of UV absorption at 300 nm following storage of the formulation at a temperature of 25±5° C. and about 60±5% relative humidity for about 24 months.

¶20. The present disclosure provides a pharmaceutical formulation as described in any one of paragraphs ¶1 to 17, wherein the pharmaceutical formulation is stable such that the formulation contains no more than 5% of bromocriptinine as determined by HPLC analysis using detection of UV absorption at 300 nm following storage of the formulation at a temperature of 25±2° C. at about 60±5% relative humidity for about 18 months.

¶21. The present disclosure provides a pharmaceutical formulation as described in paragraph ¶20, wherein the pharmaceutical formulation is stable such that the formulation contains no more than 5% of bromocriptine as determined by HPLC analysis using detection of UV absorption at 300 nm following storage of the formulation at a temperature of 25±5° C. and about 60±5% relative humidity for about 24 months.

¶22. The present disclosure provides a pharmaceutical formulation as described in any one of paragraphs ¶1 to 17, wherein the pharmaceutical formulation is stable such that the formulation contains no more than 3% total related substances as determined by HPLC analysis using detection of UV absorption at 300 nm following storage of the formulation at a temperature of 25±2° C. at about 60±5% relative humidity for about 18 months.

¶23. The present disclosure provides a pharmaceutical formulation as described in paragraph ¶22, wherein the pharmaceutical formulation is stable such that the formulation contains no more than 3% total related substances as determined by HPLC analysis using detection of UV absorption at 300 nm following storage of the formulation at a temperature of 25±5° C. and about 60±5% relative humidity for about 24 months.

¶24. The present disclosure provides a pharmaceutical formulation as described in any one of paragraphs ¶1 to 17, wherein the pharmaceutical formulation is stable such that the formulation contains no more than 3% of bromocriptinine as determined by HPLC analysis using detection of UV absorption at 300 nm following storage of the formulation at a temperature of 25±2° C. at about 60±5% relative humidity for about 18 months.

¶25. The present disclosure provides a pharmaceutical formulation as described in paragraph ¶20, wherein the pharmaceutical formulation is stable such that the formulation contains no more than 3% of bromocriptinine as determined by HPLC analysis using detection of UV absorption at 300 nm following storage of the formulation at a temperature of 25±5° C. and about 60±5% relative humidity for about 24 months.

¶26. The present disclosure provides a pharmaceutical formulation comprising micronized bromocriptine (e.g., bromocriptine mesylate or a different bromocriptine salt, e.g., bromocriptine citrate); wherein the micronized bromocriptine is present in an amount that provides a dose of at least about 0.8 mg of bromocriptine per pharmaceutical formulation; and the pharmaceutical formulation is stable such that the formulation contains no more than 5% of bromocriptinine as determined by HPLC analysis using detection of UV absorption at 300 nm following storage of the formulation at a temperature of 25±2° C. at about 60±5% relative humidity for about 18 months.

¶27. The present disclosure provides a pharmaceutical formulation as described in paragraph ¶26, wherein the pharmaceutical formulation is stable such that the formulation contains no more than 5% total related substances as determined by HPLC analysis using detection of UV absorption at 300 nm following storage of the formulation at a temperature of 25±2° C. at about 60±5% relative humidity for about 18 months.

¶28. The present disclosure provides a pharmaceutical formulation as described in paragraph ¶26, wherein the pharmaceutical formulation is stable such that the formulation contains no more than 5% of bromocriptinine as determined by HPLC analysis using detection of UV absorption at 300 nm following storage of the formulation at a temperature of 25±2° C. at about 60±5% relative humidity for about 24 months.

¶29. The present disclosure provides a pharmaceutical formulation as described in paragraph ¶26, wherein the pharmaceutical formulation is stable such that the formulation
contains no more than 5% total related substances as determined by HPLC analysis using detection of UV absorption at 300 nm following storage of the formulation at a temperature of 25±2° C. at about 60±5% relative humidity for about 24 months.

¶30. The present disclosure provides a pharmaceutical formulation as described in paragraph 126, wherein the pharmaceutical formulation is stable such that the formulation contains no more than 3% of bromocriptinine as determined by HPLC analysis using detection of UV absorption at 300 nm following storage of the formulation at a temperature of 25±2° C. at about 60±5% relative humidity for about 18 months.

¶31. The present disclosure provides a pharmaceutical formulation as described in paragraph ¶26, wherein the pharmaceutical formulation is stable such that the formulation contains no more than 3% total related substances as determined by HPLC analysis using detection of LV absorption at 300 nm following storage of the formulation at a temperature of 25±2° C. at about 60±5% relative humidity for about 18 months.

¶32. The present disclosure provides a pharmaceutical formulation as described in paragraph ¶26, wherein the pharmaceutical formulation is stable such that the formulation contains no more than 3% of bromocriptinine as determined by HPLC analysis using detection of UV absorption at 300 nm following storage of the formulation at a temperature of 25±2° C. at about 60±5% relative humidity for about 24 months.

¶33. The present disclosure provides a pharmaceutical formulation as described in paragraph ¶26, wherein the pharmaceutical formulation is stable such that the formulation contains no more than 3% of bromocriptinine as determined by HPLC analysis using detection of UV absorption at 300 nm following storage of the formulation at a temperature of 25±2° C. at about 60±5% relative humidity for about 24 months.

¶34. The present disclosure provides a pharmaceutical formulation as described in any one of paragraphs ¶1 to 25, wherein the bromocriptine is micronized.

¶35. The present disclosure provides a pharmaceutical formulation as described in any one of paragraphs ¶1 to 34, wherein the bromocriptine has a Dv90 of about 20 μm or lower.

¶36. The present disclosure provides a pharmaceutical formulation as described in paragraph ¶35, wherein the bromocriptine has a Dv90 of about 10 μm or lower.

¶37. The present disclosure provides a pharmaceutical formulation as described in paragraph ¶35, wherein the bromocriptine has a Dv90 of about 5 μm or lower.

¶38. The present disclosure provides a pharmaceutical formulation as described in any one of paragraphs ¶1 to 37, wherein the bromocriptine has a Dv99 of about 20 μm or lower.

¶39. The present disclosure provides a pharmaceutical formulation as described in paragraph ¶38, wherein the bromocriptine has a Dv99 of about 10 μm or lower.

¶40. The present disclosure provides a pharmaceutical formulation as described in paragraphs ¶1 to 39, wherein the bromocriptine has a volume-based particle size distribution wherein not more than about 20% of the bromocriptine has a particle size of less than about 1 μm.

¶41. The present disclosure provides a pharmaceutical formulation as described in any one of paragraphs ¶1 to 40, wherein the pharmaceutical formulation provides a dissolution profile, when tested in USP Apparatus Type 2 Paddle Method at 50 rpm in 500 ml of 0.1 N hydrochloric acid at about 37° C., wherein at least about 80% of the bromocriptine has been released at about 30 minutes.

¶42. The present disclosure provides a pharmaceutical formulation as described in paragraph ¶41, wherein the pharmaceutical formulation provides a dissolution profile, when tested in USP Apparatus Type 2 Paddle Method at 50 rpm in 500 ml of 0.1 N hydrochloric acid at about 37° C., wherein at least about 90% of the bromocriptine has been released at about 30 minutes.

¶43. The present disclosure provides a pharmaceutical formulation as described in paragraph ¶41, wherein the pharmaceutical formulation provides a dissolution profile, when tested in USP Apparatus Type 2 Paddle Method at 50 rpm in 500 ml of 0.1 N hydrochloric acid at about 37° C., wherein at least about 95% of the bromocriptine has been released at about 30 minutes.

¶44. The present disclosure provides a pharmaceutical formulation as described in paragraph ¶41, wherein the pharmaceutical formulation provides a dissolution profile, when tested in USP Apparatus Type 2 Paddle Method at 50 rpm in 500 ml of 0.1 N hydrochloric acid at about 37° C., wherein at least about 90% of the bromocriptine has been released at about 20 minutes.

The present disclosure provides for stable bromocriptine formulations wherein the dissolution (as tested in Example 11) of the formulation is 90% or greater within 10 minutes, 5 minutes, or 2 minutes.

¶45. The present disclosure provides a pharmaceutical formulation as described in paragraphs ¶41 to 44, wherein the pharmaceutical formulation provides a dissolution profile, when tested in USP Apparatus Type 2 Paddle Method at 50 rpm in 500 ml of 0.1 N hydrochloric acid at about 37° C., wherein not more than about 50% of the bromocriptine has been released at about 7 minutes.

¶46. The present disclosure provides a pharmaceutical formulation as described in any one of paragraphs ¶41 to 45, wherein the pharmaceutical formulation provides a dissolution profile, when tested in USP Apparatus Type 2 Paddle Method at 50 rpm in 500 ml of 0.1 N hydrochloric acid at about 37° C., wherein not more than about 75% of the bromocriptine has been released at about 10 minutes.

¶47. The present disclosure provides a pharmaceutical formulation as described in any one of paragraphs ¶1 to 46, wherein the pharmaceutical formulation provides a pharmacokinetic profile wherein the time to maximum plasma concentration ($T_{max}$) following administration of six of the formulations to adult subjects is between about 30 and 60 minutes when the formulations are administered under fasting conditions.

¶48. The present disclosure provides a pharmaceutical formulation as described in any one of paragraphs ¶1 to 47, wherein the pharmaceutical formulation provides a pharmacokinetic profile wherein the time to maximum plasma concentration ($T_{max}$) following administration of six of the formulations to adult subjects is between about 90 and about 120 minutes, when the formulations are administered under high fat fed conditions.

In another embodiment the dosage form is suitable for parenteral administration and exhibits a pharmacokinetic profile with a plasma $T_{max}$ from about 1 to about 90 minutes after administration, a plasma drug concentration of at least 50% $C_{max}$ for a duration of about 90 to about 360 minutes, and a decrease in plasma level that may approximate first order elimination kinetics.

¶49. The present disclosure provides a pharmaceutical formulation as described in any one of paragraphs ¶1 to 48, wherein the pharmaceutical formulation comprises citric acid.

¶50. The present disclosure provides a pharmaceutical formulation as described in paragraph ¶49, wherein the citric acid is present in an amount from about 1% to about 10% by weight.

¶51. The present disclosure provides a pharmaceutical formulation as described in any one of paragraphs ¶1 to 50, wherein the pharmaceutical formulation comprises a disintegrant.

¶52. The present disclosure provides a pharmaceutical formulation as described in ¶51, wherein the disintegrant is present in an amount from about 5% to about 90% by weight.

¶53. The present disclosure provides a pharmaceutical formulation as described in any one of paragraphs ¶1 to 52, wherein the bromocriptine is present in an amount that provides a dose of at least about 0.1 mg of bromocriptine per pharmaceutical formulation.

¶54. The present disclosure provides a method for the manufacture of a pharmaceutical formulation as described in any one of paragraphs ¶1 to 53 wherein the method comprises blending the bromocriptine with excipients to form a mixture wherein the bromocriptine is substantially evenly distributed in the mixture, and compressing the mixture to form a pharmaceutical formulation.

¶55. The present disclosure provides a method as described in paragraph ¶54 comprising processing bromocriptine to reduce the average particle size of the bromocriptine to provide bromocriptine that has a Dv90 of about 20 µm or less prior to the blending.

¶56. The present disclosure provides a method as described in paragraphs ¶54 or 55 comprising determining that bromocriptine has a particle size distribution equivalent to a volume-based particle size distribution with a Dv90 of about 20 µm or less prior to the blending, so that the bromocriptine that is blended is of determined particle size distribution.

¶57. The present disclosure provides a pharmaceutical formulation prepared by a method as described in any one of paragraphs ¶54 to 56.

¶58. The present disclosure provides a method of treatment for improving glycemic control in a type 2 diabetes patient comprising administering to the patient a bromocriptine pharmaceutical formulation as described in any one of paragraphs ¶1 to 53 or 57.

¶59. The present disclosure provides a method of treatment for improving glycemic control in a type 2 diabetes patient comprising providing to the patient for administration a bromocriptine pharmaceutical formulation as described in any one of paragraphs ¶1 to 53 or 57.

¶60. The present disclosure provides a method of treatment for improving glycemic control in a type 2 diabetes patient comprising preparing at least one pharmaceutical formulation by a method as described in any one of paragraphs ¶54 to 56 and providing the pharmaceutical formulation for administration to the patient.

¶61. The present disclosure provides a method of treatment of metabolic disorders or key elements thereof such as for improving glycemic control in a type 2 diabetes patient comprising preparing at least one pharmaceutical formulation by a method as described in any one of paragraphs ¶54 to 56 and administering the pharmaceutical formulation to the patient.

¶62. The present disclosure provides a solid pharmaceutical formulation comprising bromocriptine citrate, a free fatty acid or triglyceride, a non-lactose short chain saccharide such as mannitol, and citric acid.

¶63. The present disclosure provides a method for treating metabolic disorders such as type 2 diabetes mellitus, or key elements of metabolic disorders by administering to a patient in need of such treatment a pharmaceutical formulation comprising bromocriptine citrate, a free fatty acid or triglyceride, a non-lactose short chain saccharide such as mannitol, and citric acid.

¶64 The present disclosure provides an oral pharmaceutical formulation containing between 0.1-10% bromocriptine citrate, 0.1-10% citric acid, 30-90% non-lactose short chain saccharide, and 0.2-10% free fatty acid, phospholipid or triglyceride.

¶65 The present disclosure provides a parenteral pharmaceutical formulation containing between 0.1-10% bromocriptine citrate, 0.1-10% citric acid, 60-90% non-lactose short chain saccharide, and 0.2-10% free fatty acid, phospholipid or triglyceride

EXAMPLES

The inventor's discoveries are illustrated by the following examples, which are not intended to limit the scope of the claims. Other variations or embodiments of the invention will also be apparent to one of ordinary skill in the art from the above descriptions and the following Examples.

Example 1. Preparation of Stable, Micronized Bromocriptine Formulations

Milling of the bromocriptine (to prepare micronized bromocriptine) was accomplished using a Fluid Energy Model 00 Jet-O-Mizer jet mill. Enhanced stability of bromocriptine pharmaceutical formulations can be obtained by substituting either or both of two reactive excipients, magnesium and lactose, with alternative non-reactive lubricants and saccharides, respectively. Thus, to increase the stability of a bromocriptine pharmaceutical formulation, non-reactive alternatives to these reactive excipients were examined.

Stearic acid or triglyceride (as possible replacements for magnesium stearate) and mannitol (as a possible replacement for lactose) were evaluated. Tablet formulations were prepared using these non-reactive alternatives and accelerated stability tests were performed. The compositions of the formulations produced and evaluated in this project are found in Tables 1-4, below.

350 tablets of each formulation were produced. The tablets were formulated using dry granulation and pressed using a single stage tablet press. The tablets were flat round tablets with a diameter of 6.0 mm and with an average weight of 90 mg+/−5%.

TABLE 1

Formulation Guide for VS-54F-A (Bromocriptine pharmaceutical formulations with magnesium stearate and lactose).

| Excipient Name | % of total weight | Weight (mg) | Excipients for 350 Tablets (g) |
|---|---|---|---|
| Bromocriptine Mesylate | 1.05 | 0.945 | 0.331 |
| Citric Acid (Anhydrous) | 1.50 | 1.350 | 0.473 |
| Starch 1500 | 10.00 | 9.000 | 3.150 |
| Anhydrous Lactose | 86.20 | 77.580 | 27.153 |
| Fumed Silica | 0.50 | 0.450 | 0.158 |
| Magnesium Stearate | 0.75 | 0.675 | 0.236 |
| Total | 100.00 | 90.000 | 31.500 |

The hardness of the formulation was about 8-10 KP. The appearance of the tablets was white in color. The disintegration time for this formulation was about 5-8 minutes. The flow property of this granulation mixture was suitable for use in a gravity feed press.

TABLE 2

Formulation Guide for VS-54F-B (Bromocriptine pharmaceutical formulations with stearic acid substituted for magnesium stearate and mannitol substituted for lactose).

| Excipient Name | % of total weight | Weight (mg) | Excipients for 350 Tablets (g) |
|---|---|---|---|
| Bromocriptine Mesylate | 1.04 | 0.945 | 0.331 |
| Citric Acid (Anhydrous) | 1.49 | 1.350 | 0.473 |
| Starch 1500 | 9.93 | 9.000 | 3.150 |
| Anhydrous Mannitol | 85.56 | 77.580 | 27.153 |
| Fumed Silica | 0.50 | 0.450 | 0.158 |
| Stearic Acid | 1.49 | 1.350 | 0.473 |
| Total | 100.00 | 90.675 | 31.736 |

The hardness of the formulation was about 8-10 KP. The appearance of the tablets was white in color. The disintegration time for this formulation was about 5-8 minutes. The flow properties of this granulation mixture were suitable for use in a gravity feed press.

TABLE 3

Formulation Guide for VS-54F-C (Bromocriptine pharmaceutical formulations with castor oil substituted for magnesium stearate and mannitol substituted for lactose.

| Excipient Name | % of total weight | Weight (mg) | Excipients for 350 Tablets (g) |
|---|---|---|---|
| Bromocriptine Mesylate | 1.04 | 0.945 | 0.331 |
| Citric Acid (Anhydrous) | 1.50 | 1.350 | 0.473 |
| Starch 1500 | 10.00 | 9.000 | 3.150 |
| Anhydrous Mannitol | 86.20 | 77.580 | 27.153 |
| Fumed Silica | 0.50 | 0.450 | 0.158 |
| Castor Oil (Solid) | 0.75 | 0.675 | 0.236 |
| Total | 100.00 | 90.000 | 31.500 |

The hardness of the formulation was about 8-10 KP. The appearance of the tablets was white in color. The disintegration time for this formulation was abort 5-8 minutes. The flow property of this granulation mixture was suitable for use in a gravity feed press.

TABLE 4

Formulation Guide for VS-54F-B.1 (Bromocriptine pharmaceutical formulations with stearic acid substituted for magnesium stearate and mannitol substituted for lactose).

| Excipient Name | % of total weight | Weight (mg) | Excipients for 350 Tablets (g) |
|---|---|---|---|
| Bromocriptine Mesylate | 1.04 | 0.945 | 0.331 |
| Citric Acid (Anhydrous) | 1.49 | 1.350 | 0.473 |
| Starch 1500 | 9.93 | 9.000 | 3.150 |
| Anhydrous Mannitol | 85.56 | 77.580 | 27.153 |
| Fumed Silica | 0.50 | 0.450 | 0.158 |
| Stearic Acid | 1.49 | 1.350 | 0.473 |
| Total | 100.00 | 90.675 | 31.736 |

The hardness of the formulation was about 8-10 KP. The appearance of the tablets was white in color. The disintegration time for this formulation was about 5-8 minutes. The flow property of this granulation mixture was suitable for use in a gravity feed press.

Each of the above-described formulations was prepared and tested for assay, content uniformity and for starting bromocriptinine (the main degradation product of bromocriptine; BCI) content prior to being subjected to stress at 40° C./75% RH. For content uniformity, three tablets from each formulation were tested. The lot numbers for each of these formulations are shown below:
VS-54F-A
VS-54F-B
VS-54F-C
VS-54F-B.1 (Second preparation of Formulation B)

Example 2. Stability and Dissolution Studies of Three Tablet Bromocriptine Formulations Using HPLC, a calibration curve was set up to analyze each of the formulations described in Example 1. For assay and % bromocriptinine (the main degradation product of bromocriptine; BCI) determination, one tablet was dissolved in 10 ml of 0.1% citric acid solution in a volumetric flask to give a theoretical concentration of about 0.0945 mg/ml. Based on the new information regarding sample stability and our need for a $T_0$ we analyzed a tablet of each formulation stored at 5° C. bracketed by 2 tablets that were stressed at 40° C./75% RH. All 4 formulations were analyzed at T=2, 4, and 6 weeks for assay and % BCI. The percent BCI was calculated based on the area of the BCI peak and the total area of the BCI and API peaks.

TABLE 5

Bromocriptine Assay of Formulations.

| Condition | 2 weeks | 4 weeks | 6 weeks |
|---|---|---|---|
| A 40/75 | 91.9 | 91.5 | 90.4 |
| A 5C | 95.0 | 91.8 | 91.6 |
| B 40/75 | 78.6 | 86.5 | 98.9 |
| B 5C | 95.4 | 90.4 | 82.0 |
| C 40/75 | 86.1 | 84.5 | 91.1 |
| C 5C | 90.6 | 105.4 | 77.5 |
| B.1 40/75 | 112.0 | 107.4 | 108.0 |
| B.1 5C | 117.6 | 102.0 | 121.7 |

Assays for all of the formulations over the course of the stability study.

TABLE 6

% Bromocriptinine in Formulations.

| Condition | 2 weeks | 4 weeks | 6 weeks |
|---|---|---|---|
| A 40/75 | 0.74 | 1.24 | 2.26 |
| A 5C | 0.25 | 0.20 | 0.16 |
| B 40/75 | 0.42 | 0.53 | 0.78 |
| B 5C | 0.19 | 0.19 | 0.19 |
| C 40/75 | 0.12 | 0.20 | 0.26 |
| C 5C | 0.08 | 0.12 | 0.17 |
| B.1 40/75 | 0.59 | 0.73 | 0.89 |
| B.1 5C | 0.24 | 0.24 | 0.24 |

% BCI (degradation product of bromocriptine) for each formulation based on the area of the bromocriptine API and the BCI peaks.

As expected, there was a slight increase in % BCI in all of the samples stressed at 40/75 over the course of the study. Formulation C<VS-54F-C) had the lowest % BCI at the start and its % BCI remained low throughout the entire study (i.e., Formulation C gave the best stability with regard to bromocriptine decomposition as evidenced by % BCI). Formulation B had the next lowest percent of BCI throughout the study. The highest amount of decomposition was seen in Formulation A. Relative to Formulation A, Formulations B and C markedly reduced the degradation of bromocriptine under the test conditions employed, by 63% and 88%, respectively.

Each formulation was also tested for dissolution using a basket apparatus, a paddle apparatus, and a flow-through cell (Formulation C only). For the basket and paddle apparatus, 11 tablets from each formulation were weighed and added to 1,000 ml of 0.2% citric acid solution. Time points were taken at 10, 15, 20, 25, 30, 45, and 60 minutes. The samples were prepared for analysis by centrifugation and injection of the resulting mother liquors. For the flow-through cell, 1 tablet was used in 100 ml of solvent which continuously flowed through the cell. The samples were prepared in the same way as for the basket and paddle apparatus. Dissolution testing of all of the tablet formulations showed fast and high release recoveries of the API over the course of an hour. In all cases, the release after 30 minutes was >90% theory and in many cases reached the 90$^{th}$ percentiles early in the sampling.

It can be appreciated from a comparison of studies of degradation of bromocriptine from a formulation lacking magnesium stearate and lactose (see, e.g., Tables 5 and 6, Formulations B and C at 6 weeks at 40° C./75% RH) versus from a formulation containing magnesium stearate and lactose that the impact to reduce degradation of bromocriptine is much greater when both magnesium stearate and lactose are not present as constituents of the formulation.

Example 3: Methods Used in Examples 1 and 2

Bromocriptine HPLC assay. HPLC Setup: Agilent 1100; Column: Waters Symmetry Shield RP18, 3.5 micron 4.6× 150 mm; P/N 186000180
  Mobile Phase A: 0.1% TFA Water
  Mobile Phase B: 0.1% TFA Acetonitrile
  Gradient:

| Time | % A | % B |
|---|---|---|
| 0 | 80 | 20 |
| 5 | 65 | 35 |
| 20 | 60 | 40 |
| 21 | 80 | 20 |
| 25 | 80 | 20 |

Flow: 1 ml/min; Detection UV: 300 nm; Sample Diluent: 0.1% citric acid; Column Oven Temperature: 30° C.; Injection Volume: 100 µl Bromocriptine Particle Size Reduction using Jet Milling. Excipients: Bromocriptine Mesylate; Equipment: Malvern Mastersizer Particle Size Analyzer (Model MS/S); Scale 0.0000 readability; Spatulas; 500 ml Amber Glass Bottle With Teflon Lined Lid; Fluid Energy Model 00 Jet-O-Mizer; Dry Compressed Air; TA Instruments Differential Scanning Calorimeter; TA Instruments Thermo Gravimetric Analyzer; Olympus Microscope.

In a weighing dish 1.0 g bromocriptine was weighed to the nearest 0.000 grams. The material was then loaded into the vibratory feeder. After loading the sample the compressed air line set to 100 psi was connected to the mill, then the gas inlet switch to the instrument was moved to the on position. The grinding pressure was then set to 40 psi and the feeding pressure was set to 50 psi. After the pressures were set for the mill, the feeder power knob was then set to the zero position, and the current for the feeder was turned on. After the current was turned on, the power button on the feeder was turned until the desired feeding rate into the hopper was achieved this translated to a dial reading of about 1.5 from a scale of 1 to 10 (about 0.500 grams of API/min). Grinding at this feeding pressure was continued until all of the material was fed into the mill. When all of the material (1.000 gas initially weighed) was milled, the gas was then turned off. The milled material from this run was removed from the collecting filter, then another 1.000 g bromocriptine was weighed out and milling was resumed. After milling was completed, all of the milled material was placed in one 20 ml glass vial with cap. The total amount of product recovered was 1.500 grams (75% yield). The milled product was then characterized using the following methods: Microscopy, HPLC, and Particle Size Analysis.

Microscopy: Approximately 2-3 mg of KPT-350 was placed on a glass slide. Using a cover glass the material was carefully spread evenly on the surface of the slide. The spread material was covered with the cover glass and observations were made at 50×. Examination of these materials with polarized light revealed that the materials were crystalline in nature. No amorphous zones were observed. The un-milled material had particles that ranged in size from about 0.5-10 μm.

The jet milled material had an average particle size of about 0.5-3.0 μm.

HPLC: HPLC analysis of un-milled and milled material confirmed that there was no change to the chemical composition.

Tableting of Milled Bromocriptine. Chemicals: Milled Bromocriptine Mesylate (NAT) Lot #: VS-ER-001; Anhydrous Citric Acid (Fisher) Lot #: 100610; Starch 1500 (Colorcon) Lot #: IN510883; Mannitol (SPI Pharma) Lot #: 06N129; Lactose Lactopress Anhydrous 250 (DFE Pharma); Aerosil R202 (Evonik) Lot #: 3150090932; Magnesium Stearate (Spectrum Chemicals) Lot #: UL0756; Stearic Acid (Spectrum Chemicals) Lot #: TB1349; Fully Hydrogenated Castor Oil Acid (ACME Hardesty) Lot #: 07-H-29.

Equipment: Laboratory Scale (0.000 readability); TDP 1.5 Table Top Tablet Press; 6 mm Concave round punches; 6 mm Round Dies; 50 ml Vials With Caps; Variable Speed Roller.

Procedure for blending Formulation VS-54F-A: A 50 ml round flask with cap was charged with 0.331 g bromocriptine and 0.473 g citric acid. The mixture was briskly shaken for a few seconds, then placed in the roller where the blend was permitted to roll (at highest speed) for 10 minutes.

After rolling for 10 minutes, blending was stopped and 3.150 g starch 1500 was added to the blend. The mixture was then briskly shaken for a few seconds, then placed in the roller where the blend was permitted to roll (at highest speed) for 10 minutes.

After rolling for 10 minutes, blending was stopped and 27.153 g anhydrous lactose and 0.158 g fumed silica were added to the blend. The mixture was then briskly shaken for a few seconds, then placed in the roller where the blend was permitted to roll (at highest speed) for 10 minutes.

After rolling for 10 minutes, blending was stopped and 0.236 g magnesium stearate was added to the blend. After the addition of the magnesium stearate, the mixture was then briskly shaken for a few seconds, then rolled at the highest speed for two minutes.

After rolling for two minutes, the mixture was loaded into the feeder of the tablet press. The mixture was then pressed into tablets at the highest pressure tolerable for the TDP 1.5 (about 1.5 tons of pressure). The tablet shape was a 6 mm flat round with and the average weight was about 0.090+/−5% grams.

After completing the run hardness tests, disintegration tests, and observations were made.

Procedure for blending Formulation VS-54F-B: A 50 ml round flask with cap was charged with 0.331 g bromocriptine and 0.473 g citric acid. The mixture was briskly shaken for a few seconds, then placed in the roller where the blend was permitted to roll (at highest speed) for 10 minutes.

After rolling for 10 minutes, blending was stopped and 3.150 g starch 1500 was added to the blend. The mixture was then briskly shaken for a few seconds, then placed in the roller where the blend was permitted to roll (at highest speed) for 10 minutes.

After rolling for 10 minutes, blending was stopped and 27.153 g anhydrous mannitol and 0.158 g fumed silica were added to the blend. The mixture was then briskly shaken for a few seconds, then placed in the roller where the blend was permitted to roll (at highest speed) for 10 minutes.

After rolling for 10 minutes, blending was stopped and 0.473 g stearic acid was added to the blend. After the addition of the stearic acid, the mixture was briskly shaken for a few seconds, then rolled at the highest speed for two minutes.

After rolling for two minutes, the mixture was loaded into the feeder of the tablet press. The mixture was then pressed into tablets at the highest pressure tolerable for the TDP 1.5 (about 1.5 tons of pressure). The tablet shape was a 6 mm flat round with and the average weight was about 0.090+/−5% grams.

After completing the run hardness tests, disintegration tests, and observations were made.

Procedure for blending Formulation VS-54F-C: A 50 ml round flask with cap was charged with 0.331 g bromocriptine and 0.473 g citric acid. The mixture was briskly shaken for a few seconds, then placed in the roller where the blend was permitted to roll (at highest speed) for 10 minutes.

After rolling for 10 minutes, blending was stopped and 3.150 g starch 1500 was added to the blend. The mixture was then briskly shaken for a few seconds, then placed in the roller where the blend was permitted to roll (at highest speed) for 10 minutes.

After rolling for 10 minutes, blending was stopped and 27.153 g anhydrous mannitol and 0.158 g fumed silica were added to the blend. The mixture was briskly shaken for a few seconds, then placed in the roller where the blend was permitted to roll (at highest speed) for 10 minutes.

After rolling for 10 minutes, blending was stopped and 0.236 g fully hydrogenated castor oil was added to the blend. After the addition of the castor oil, the mixture was briskly shaken for a few seconds, then rolled at the highest speed for two minutes.

After rolling for two minutes, the mixture was loaded into the feeder of the tablet press. The mixture was then pressed into tablets at the highest pressure tolerable for the TDP 1.5 (about 1.5 tons of pressure). The tablet shape was a 6 mm flat round with and the average weight was about 0.090±5% grams.

After completing the run hardness tests, disintegration tests, and observations were made.

Procedure for blending Formulation VS-54F-B.1: A 50 ml round flask with cap was charged with 0.331 g bromocriptine and 0.473 g citric acid. The mixture was briskly shaken for a few seconds, then placed in the roller where the blend was permitted to roll (at highest speed) for 10 minutes.

After rolling for 10 minutes, blending was stopped and 3.150 g starch 1500 was added to the blend. The mixture was briskly shaken for a few seconds, then placed in the roller where the blend was permitted to roll (at highest speed) for 10 minutes.

After rolling for 10 minutes, blending was stopped and 27.153 g anhydrous mannitol and 0.158 g fumed silica were added to the blend. The mixture was briskly shaken for a few seconds, then placed in the roller where the blend was permitted to roll (at highest speed) for 10 minutes.

After rolling for 10 minutes, blending was stopped and 0.473 g stearic acid was added to the blend. After the addition of the stearic acid, the mixture was briskly shaken for a few seconds, then rolled at the highest speed for two minutes.

After rolling for two minutes, the mixture was loaded into the feeder of the tablet press. The mixture was then pressed into tablets at the highest pressure tolerable for the TDP 1.5 (about 1.5 tons of pressure). The tablet shape was a 6 mm flat round with and the average weight was about 0.090±5% grams.

After completing the run hardness tests, disintegration tests, and observations were made.

Example 4. Studies on the Browning (Degradation) Reactions of Bromocriptine Plus Magnesium Stearate, with or without Lactose A series of reaction vessels were prepared containing various combinations of bromocriptine mesylate, Mg stearate, and/or lactose, with or without citric acid, in aqueous suspension and reacted at 60° C. for 55 hours. Additionally, samples were prepared wherein the Mg stearate was replaced/substituted with stearic acid.

Mg stearate was from Sigma (MAGNESIUM STEARATE EXTRA PURE DAB, PH. E, Sigma Product Number: 26454); stearic acid was from Sigma (STEARIC ACID, REAGENT GRADE, 95%, Sigma Product Number: 175366); lactose was from Sigma (LACTOSE ANHYDROUS, PH EUR, Sigma Product Number: 17814); and citric acid was from Sigma (craw Am ANHYDROUS, Sigma Product Number: 27109). Any or all of these reagents can be acquired from other sources known in the art.

Figure 2:
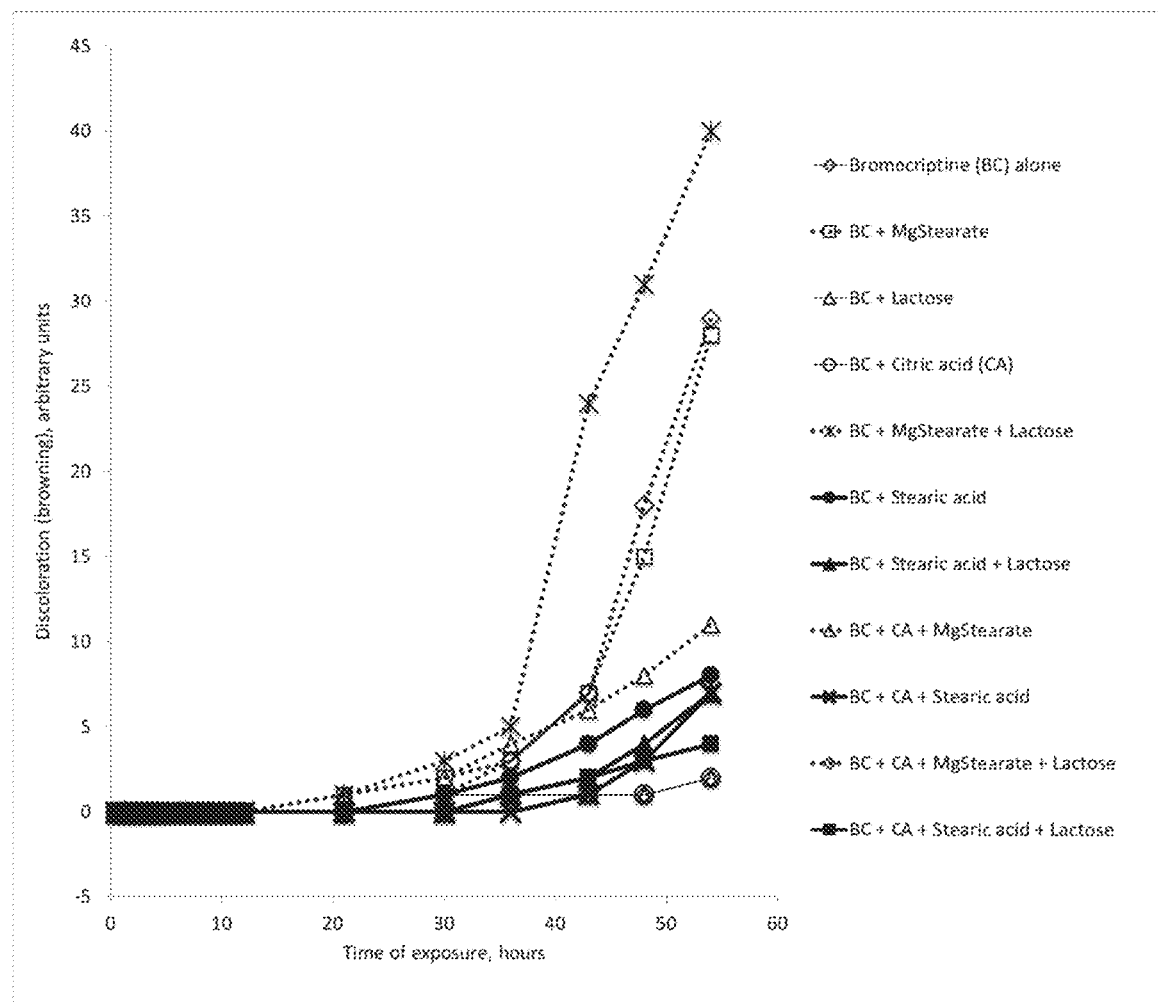
FIG. 2 shows a plot of the effect of various additives on the degradation of bromocriptine (evaluated via the formation of the browning reaction) as a function of time of exposure to a heated aqueous environment.

Reagents were weighed out as indicated in Table 7 below. 2 ml of distilled water was added to the samples, which were then mixed by vortexing, placed in a reaction chamber with thermostat set at 50° C. for 24 hours, then (after 24 hours) set at 60° C. The color change of the sample solutions/mixtures were evaluated by comparing the color of the solution with a Standardized Color Chart; the color intensities of the sample solutions/mixtures (from clear to dark brown) was graded at specified time points from time 0 to time 55 hours (see FIG. 2). In FIG. 2, a number "0" indicates a clear solution or white suspension; a number "40" represents the darkest solution/suspension observed.

5) Addition of citric acid and substitution of Mg stearate with stearic acid attenuated bromocriptine degradation and the browning reaction by the greatest magnitude (i.e., greater than either addition of citric acid alone or substitution of Mg stearate with stearic acid alone).

6) Substitution of Mg stearate with solid castor oil attenuated bromocriptine degradation to an even greater extent than substitution of Mg stearate with stearic acid.

In summary, removing Mg stearate from a bromocriptine formulation enhances its stability in terms of a browning reaction product formation, whether in the presence or absence of lactose. Lactose in the presence of Mg stearate further enhances the browning reaction. Importantly, it was found that of the two components of Mg stearate, it is the Mg, not the stearate that facilitates the browning reaction, as replacement of Mg stearate with stearic acid markedly improves bromocriptine stability. Removing Mg stearate from a bromocriptine formulation and replacing it with stearic acid or another non-magnesium salt glidant (e.g., solid castor oil) enhances the stability of the bromocriptine formulation. Removing lactose from a bromocriptine formulation and replacing it with mannitol or another short chain saccharide enhances the stability of the bromocriptine formulation. The addition of citric acid to a bromocriptine formulation that is substantially free of magnesium and lactose can to a finite degree further reduce (i.e., protect against) any/all of these degradation reactions, but it itself is not enough to prevent them.

TABLE 7

List of Ingredients in the Formulations Tested.

| | Bromocriptine, mg | Citric acid, mg | MgStearate, mg | Stearic acid, mg | Lactose, mg |
|---|---|---|---|---|---|
| Bromocriptine (BC) alone | 10 | | | | |
| BC + Mg stearate | 10 | | 7 | | |
| BC + Lactose | 10 | | | | 800 |
| BC + citric acid (CA) | 10 | 14 | | | 800 |
| BC + Mg stearate + Lactose | 10 | | 7 | | 800 |
| BC + Stearic acid | 10 | | | 7 | |
| BC + Stearic acid + Lactose | 10 | | | 7 | 800 |
| BC + CA + Mg stearate | 10 | 14 | 7 | | |
| BC + CA + Stearic acid | 10 | 14 | | 7 | |
| BC + CA + Mg stearate + Lactose | 10 | 14 | 7 | | 800 |
| BC + CA + Stearic acid + Lactose | 10 | 14 | | 7 | 800 |

Thus, it was observed that:
1) When Mg stearate was allowed to interact with bromocriptine in an aqueous environment, a browning product was produced even in the absence of lactose.
2) A more intense browning reaction occurred when bromocriptine was exposed to both Mg stearate and lactose.
3) Addition of citric acid attenuated bromocriptine degradation and the browning reaction when bromocriptine was exposed to Mg stearate alone, as well as when bromocriptine was exposed to both Mg stearate and lactose.
4) Substitution of Mg stearate with stearic acid attenuated bromocriptine degradation and the browning reaction when bromocriptine was not exposed to lactose, as well as when bromocriptine was exposed to lactose.

Example 5. Studies on the Stability of Bromocriptine Pharmaceutical Formulations Formulated with Replacement of Magnesium Stearate with Stearic Acid or Triglyceride and with Replacement of Lactose with Mannitol To test the relative stabilities of bromocriptine pharmaceutical formulations formulated with or without Mg stearate and lactose, several different bromocriptine formulations (e.g., tablets) were manufactured by standard mixing and tableting procedures known in the art:

Formulation A: Tableted bromocriptine formulation with Mg stearate and lactose 0.945 mg bromocriptine mesylate; 9.00 mg corn starch 1500; 1.350 mg anhydrous citric acid; 77.58 mg anhydrous lactose; 0.450 mg silicon dioxide; 0.675 mg magnesium stearate Formulation B: Tableted bromocriptine formulation with Mg stearate substituted with stearic acid and lactose substituted with mannitol 0.945 mg bromocriptine mesylate; 9.00 mg corn starch 1500; 1.350 mg anhydrous citric acid; 77.58 mg anhydrous mannitol; 0.450 mg silicon dioxide; 1.350 mg stearic acid Formulation C: Tableted bromocriptine formulation with Mg stearate substituted with solid castor oil and lactose substituted with mannitol.

0.945 mg bromocriptine mesylate; 9.00 mg corn starch 1500; 1.350 mg anhydrous citric acid; 77.58 mg anhydrous mannitol; 0.450 mg silicon dioxide; 0.675 mg solid castor oil The manufactured bromocriptine formulations were placed into sealed containers and subsequently subjected to an environment of 40° C. and 75% relative humidity for six weeks. Following six weeks' exposure to this environment, the formulations were dissolved and analyzed for bromocriptinine (the major degradant of bromocriptine) content by HPLC analysis. Relative to bromocriptine formulation A (which contained Mg stearate and lactose), bromocriptine formulation B (with stearic acid substituted for Mg stearate and mannitol substituted for lactose) and bromocriptine formulation C (with solid castor oil substituted for Mg stearate and mannitol substituted for lactose) displayed a reduction in the amount of the bromocriptine degradation product (i.e., bromocriptinine) in the formulations of 63% and 88%, respectively.

Example 6. Preparation, Stability and Dissolution of Micronized Bromocriptine Mesylate Pharmaceutical Formulations Prepared with Various Lubricants Test pharmaceutical formulations of micronized bromocriptine mesylate (identified as Formulations A-E) were prepared using micronized bromocriptine mesylate and various lubricants. The ingredients used for each formulation are listed in Table 8 below.

The formulations were then stored at 25±2° C. and 60±5% RH, at 30±2° C. and 65±5% RH or at 40±2° C. and 75±5% RH for up to 3 months.

The total related substances impurity in each batch of formulations was measured using an HPLC method was determined at the beginning of the experiment (T=0) and at 1, 2 and/or 3 months. Since bromocriptine is light sensitive, amber glassware was used for all solution preparations. To determine the amount of related substance, at least 5 formulations were weighed to determine the average formulation weight. An aliquot of the ground sample equivalent to 3.5 formulations (2.8 mg of bromocriptine) was accurately weighed and quantitatively transferred the sample into a 25 ml volumetric flask. Aqueous methanol (1:1 v/v, 15 ml) was added and the solution was sonicated for 10 minutes then diluted to 25 ml total volume and mixed well. The sample solution was then filtered and analyzed by reversed phase HPLC using a Waters 250×

4.6 mm SUNFIRE C18 column (5 µm particle size), an isocratic mobile phase of 0.1 M potassium phosphate buffer (pH 7.5)/acetonitrile (1:1 v/v), an autosampler temperature of 5° C., an injection volume of 100 µL, a flow rate of 1.5 µL/min, ambient column temperature and detection by UV absorption at 300 nm. Under these conditions, bromocriptine elutes in about 11-15 minutes and the impurity bromocriptinine elutes in about 35-45 minutes (a relative retention time of about 2.6). The related substances impurity was calculated using the formulae:

% Individual Related Substance=$A_i/A_t \times 100\%$

Total Impurities=$\Sigma$% Individual Related Substance wherein:

$A_i$=Peak area for an individual related substance in the sample solution chromatogram $A_t$=Total area for all peaks in the sample chromatogram, disregarding the void disturbance and any peaks observed in the chromatogram of the diluent.

Figure 1B:
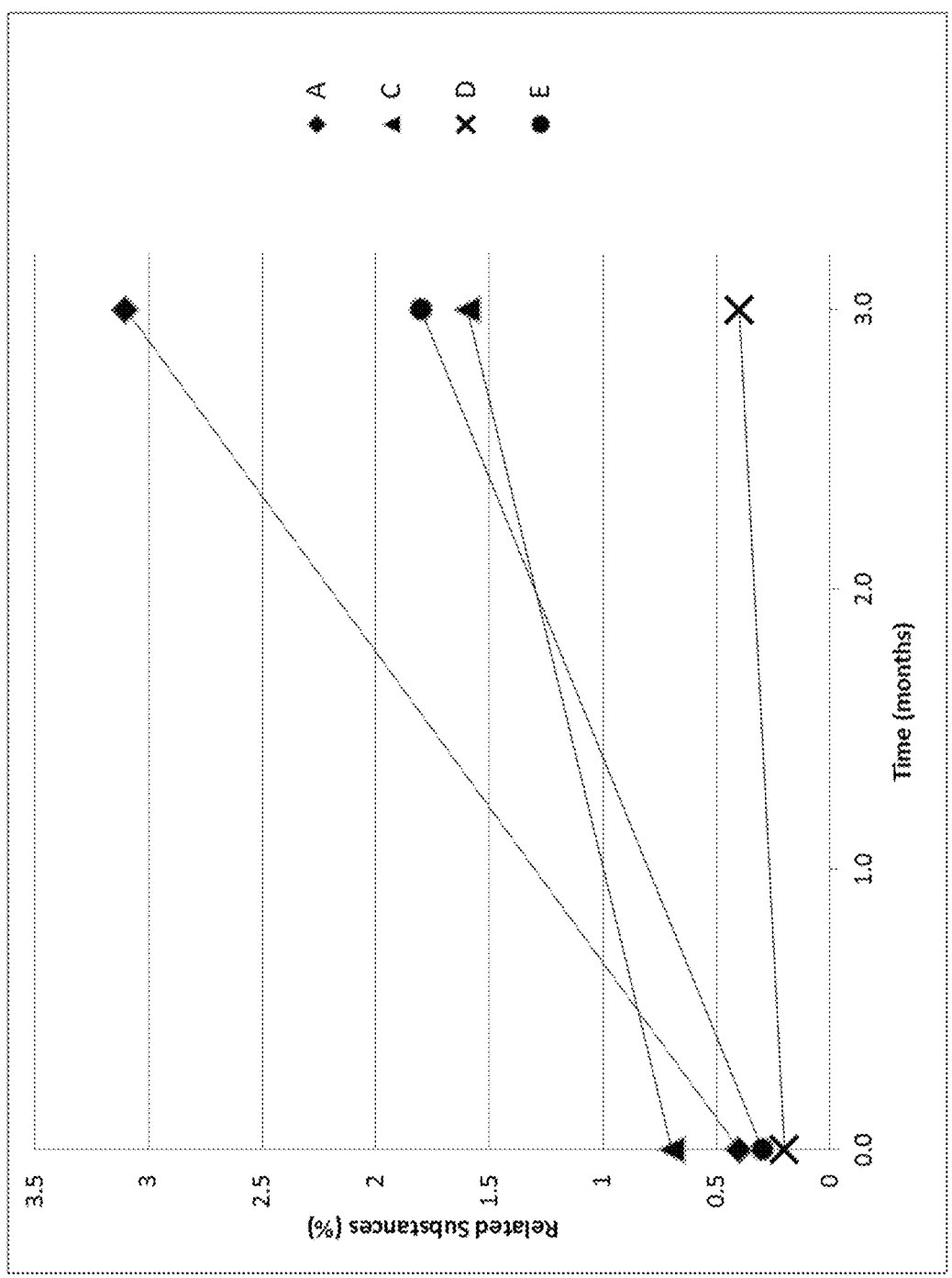
FIG. 1B shows a plot of the total related substances impurity measured for bromocriptine mesylate pharmaceutical formulation formulations prepared using micronized bromocriptine mesylate and various lubricants at the beginning of an experiment to measure product stability (T=0) and following storage at 30±2° C. and 65±5% RH for 3 months.
Figure 1C:
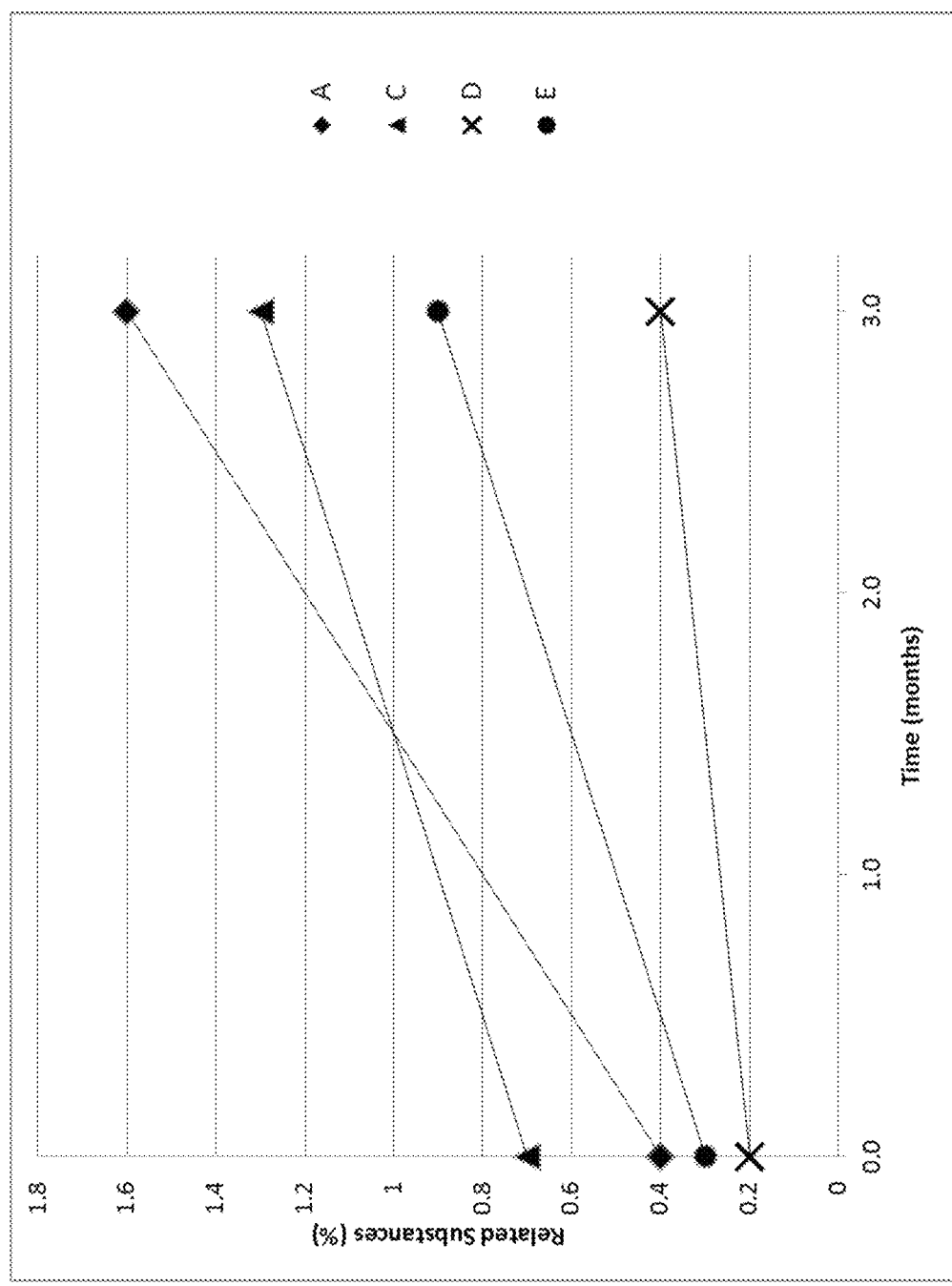
FIG. 1C shows a plot of the total related substances impurity measured for bromocriptine mesylate pharmaceutical formulation formulations prepared using micronized bromocriptine mesylate and various lubricants at the beginning of an experiment to measure product stability (T=0) and following storage at 25±2° C. and 60±5% RH for 3 months.
Figure 3:
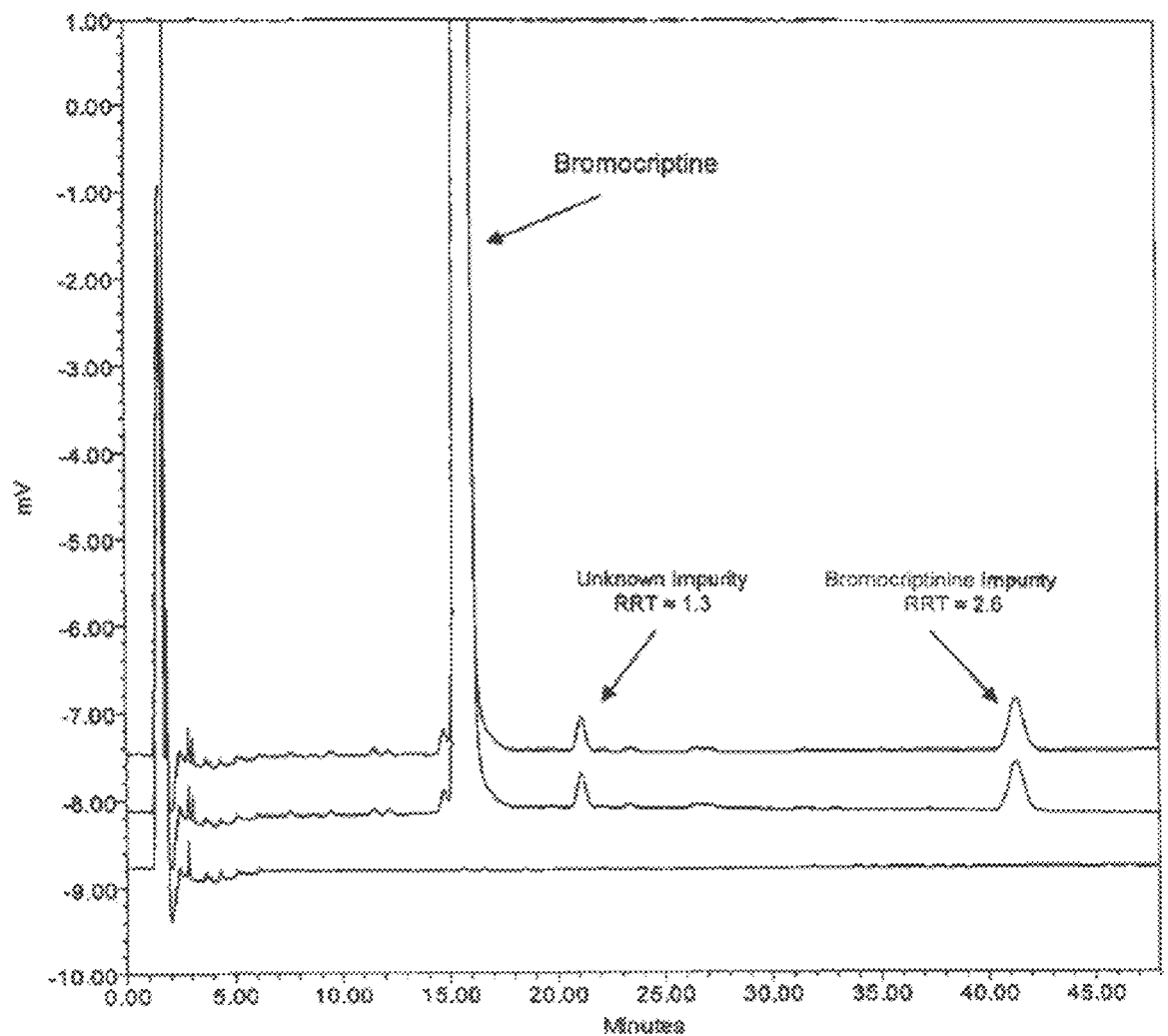
FIG. 3 shows a typical chromatogram of a blank solution, a reference bromocriptine mesylate solution containing 0.112 mg/ml of bromocriptine mesylate, and a sample solution prepared from bromocriptine mesylate pharmaceutical formulations.

The results of the stability testing are shown in Table 9 and FIGS. 1A, 1B, and 1C. FIG. 3 shows typical chromatograms of a blank solution, a reference solution containing 0.112 mg/ml of bromocriptine mesylate, and a sample solution.

TABLE 8

Bromocriptine Mesylate Pharmaceutical Formulations (PF) (Formulations A-E) Prepared Using Micronized Bromocriptine and Various Lubricants.

| | Formulation | | | | | | | | | |
|---|---|---|---|---|---|---|---|---|---|---|
| | A (control) | | B | | C | | D | | E | |
| Ingredient | mg/PF | g/batch | mg/PF | g/batch | mg/PF | g/batch | mg/PF | g/batch | mg/PF | g/batch |
| Bromocriptine mesylate (micronized) | 0.95 | 10.6 | 0.95 | 10.6 | 0.95 | 10.6 | 0.95 | 10.6 | 0.95 | 10.6 |
| Corn starch NF | 9.00 | 99.9 | 9.00 | 99.9 | 9.00 | 99.9 | 9.00 | 99.9 | 9.00 | 100.0 |
| Citric acid NF | 1.35 | 15.0 | 1.35 | 15.0 | 1.35 | 15.0 | 1.35 | 15.0 | 1.35 | 15.0 |
| Anhydrous lactose NF | 77.58 | 861.9 | 76.48 | 849.5 | 76.48 | 849.5 | 76.48 | 849.5 | 77.88 | 865.0 |
| Colloidal SiO$_2$ NF | 0.45 | 5.0 | 0.45 | 5.0 | 0.45 | 5.0 | 0.45 | 5.0 | 0.45 | 5.0 |
| Magnesium stearate NF | 0.68 | 7.6 | | | | | | | 0.4 | 4.4 |
| Stearic acid NF | | | 1.8 | 20 | | | | | | |
| Sodium stearyl fumarate NF | | | | | 1.8 | 20 | | | | |
| Hydrogenated castor oil (KOLLIWAX ® HCO) | | | | | | | 1.8 | 20 | | |
| Total Weight | 90.0 | 1000 | 90.0 | 1000 | 90.0 | 1000 | 90.0 | 1000 | 90.0 | 1000 |

TABLE 9

Measurement of Related Substances in Bromocriptine Mesylate
Pharmaceutical Formulations (Formulations A-E) Prepared Using
Micronized Bromocriptine Mesylate and Various Lubricants.

| Formulation | Conditions | Related Substances (%) | | | |
|---|---|---|---|---|---|
| | | T = 0 | T = 1 month | T = 2 months | T = 3 months |
| A (control) | 40° C./75% RH | 0.4 | 3.8 | 7.3 | 11.0 |
| | 30° C./65% RH | — | — | — | 3.1 |
| | 25° C./60% RH | — | — | — | 1.6 |
| B | 40° C./75% RH | 0.6 | 3.9 | 5.8 | Not tested |
| C | 40° C./75% RH | 0.7 | 2.0 | 3.0 | 4.9 |
| | 30° C./65% RH | — | — | — | 1.6 |
| | 25° C./60% RH | — | — | — | 1.3 |
| D | 40° C./75% RH | 0.2 | 0.4 | 0.5 | 2.5 |
| | 30° C./65% RH | — | — | — | 0.4 |
| | 25° C./60% RH | — | — | — | 0.4 |
| E | 40° C./75% RH | 0.3 | 2.4 | 4.0 | 5.6 |
| | 30° C./65% RH | — | — | — | 1.8 |
| | 25° C./60% RH | — | — | — | 0.9 |

The results summarized in Table 9 are also shown in FIGS. 1A, 1B, and 1C.

FIG. 1A shows a plot of the total related substances impurity measured for bromocriptine mesylate pharmaceutical formulations (formulations A-E) prepared using micronized bromocriptine mesylate and various lubricants at the beginning of the experiment (T=0) and following storage at 40±2° C. and 75±5% RH for 1, 2 or 3 months.

FIG. 1B shows a plot of the total related substances impurity measured for bromocriptine mesylate pharmaceutical formulations (formulations A and C-E) prepared using micronized bromocriptine mesylate and various lubricants at the beginning of the experiment (T=0) and following storage at 30±2° C. and 65±5% RH for 3 months.

FIG. 1C shows a plot of the total related substances impurity measured for bromocriptine mesylate pharmaceutical formulations (formulations A and C-E) prepared using micronized bromocriptine mesylate and various lubricants at the beginning of the experiment (T=0) and following storage at 25±2° C. and 60±5% RH for 3 months.

The results of this study demonstrate that substitution within the described tableted micronized bromocriptine formulation of magnesium stearate (Formulation A) with either stearic acid (Formulation B), sodium stearyl fumarate (Formulation C), or hydrogenated castor oil (Formulation D) in the otherwise same micronized bromocriptine formulation (and all containing lactose and citric acid) each markedly enhanced the stability of the micronized bromocriptine to heat and humidity over the test period in the test conditions employed.

In addition to testing for the presence of impurities, dissolution testing was performed for formulations A and C-E at the beginning of the experiment (T=0) and following storage at 25±2° C. and 60±5% RH for 3 months. The results of the dissolution testing are shown in Table 10. The samples were tested using a USP Type 2 Apparatus at 50 RPM in 500 ml of 0.1 N hydrochloric acid at 37±0.5° C. with the sample drawn at 30 minutes. The bromocriptine mesylate in the sample was quantitated by HPLC as described above.

TABLE 10

Dissolution of Bromocriptine Mesylate Pharmaceutical Formulations
(Formulations A and C-E) Prepared Using Micronized Bromocriptine
Mesylate and Various Lubricants after 30 min. (USP Type 2 Apparatus,
50 RPM) in 0.1N Hydrochloric Acid at 37 ± 0.5° C. Before
and After Storage at 25 ± 2° C. and 60 ± 5% RH for 3 months.

| Formulation | T = 0 | T = 3 months |
|---|---|---|
| A | 104.0% | 102.3% |
| C | 103.6% | 100.9% |
| D | 103.9% | 98.7% |
| E | 106.2% | 100.9% |

Example 7. Citric acid was dissolved, in separate reaction vessels, in one of either methanol, ethanol, or butanol at about 4 mg per ml at room temperature Free base bromocriptine was dissolved in separate reaction vessels in either methanol, ethanol, or butanol at about 12 mg per 5-30 ml. The like organic solutions of citric acid and of bromocriptine (i.e., ethanol-ethanol, methanol-methanol, butanol-butanol) were then mixed in an equi-mole amount of bromocriptine and citrate. The three resulting solutions were stirred for about 2-24 hours at room temperature until the solvent evaporated to dryness. The resulting solid product in each reaction vessel contains bromocriptine citrate.

Example 8. Solubility of Bromocriptine Citrate Relative to Bromocriptine Mesylate Solid samples of equal amounts of bromocriptine mesylate and bromocriptine citrate were added, under various pH conditions, to equal volumes of water or water/organic solutions in different vessels and the dissolution of the bromocriptine samples (aqueous solubility) was assessed over time. Bromocriptine citrate was found to dissolve much more quickly and with significantly greater solubility (increased mg of bromocriptine dissolved per ml of water in the citrate vs mesylate salt form) compared to bromocriptine mesylate.

Example 9. Citric acid was dissolved in ethanol and free base bromocriptine was dissolved in an organic solvent in separate reaction vessels. The organic solutions of citric acid and of bromocriptine were then mixed in an equi-mole amount of bromocriptine and citrate. The resulting solution was stirred for about 2-24 hours at low temperature and the solvent was evaporated to dryness. The resulting solid product contained bromocriptine citrate which was over 7-fold more water soluble at 20 C than bromocriptine mesylate.

Example 10. Effect of constituents on the stability and solubility of bromocriptine formulations. Different pharmaceutical formulations of bromocriptine are manufactured with varying inclusion/substitution of the constituents as described in Table 11 (below) and in the descriptions of herein versus a traditional formulation of bromocriptine mesylate as described in Table 1. The stability and solubility of the formulations are assessed versus a traditional formulation of bromocriptine mesylate as described in Table 1. Relative to the traditional pharmaceutical formulation described in Table 1, the pharmaceutical formulation of bromocriptine citrate, fatty acid or triglyceride, non-lactose short chain saccharide, and citric acid is found to have an improved stability to heat and humidity (tested at 40 C and 75% RH) and water solubility (at 20 C) versus the traditional pharmaceutical formulation of bromocriptine mesylate and also versus any 1, 2, or 3 combinations of components of the pharmaceutical formulation of bromocriptine citrate, fatty acid or triglyceride, non-lactose short chain saccharide, and citric acid.

After rolling for 10 minutes blending was stopped and to the blend 0.050 grams of stearic acid was added. After the addition of the stearic acid the mixture was then briskly

TABLE 11

EFFECT OF CONSTITUENTS ON THE STABILITY AND SOLUBILITY OF BROMOCRIPTINE FORMULATIONS

| Bromocriptine Mesylate Or Bromocriptine Citrate | Fatty Acid Such As Stearic Acid or Triglyceride Substituted For Mg Stearate | Short Chain Saccharide Such As Mannitol Substituted For Lactose | Citric Acid | Relative Improvement In Heat & Humidity Stability Versus Traditional Bromocriptine Mesylate Pharmaceutical Formulation* | Relative Improvement in Water Solubility Versus Traditional Bromocriptine Mesylate Pharmaceutical Formulation* |
|---|---|---|---|---|---|
| Bromocriptine Mesylate[1] | ✓ | | | ++[2] | − |
| | | ✓ | | + | − |
| | | | ✓ | ++ | ++ |
| | ✓ | ✓ | | +++ | − |
| | ✓ | | ✓ | +++++ | ++ |
| | | ✓ | ✓ | +++ | ++ |
| | ✓ | ✓ | ✓ | +++++++ | ++ |
| | ✓ | | | ++ | +++ |
| Bromocriptine Citrate[1] | ✓ | | | + | +++ |
| | | | ✓ | ++ | ++++++ |
| | ✓ | ✓ | | +++ | +++ |
| | ✓ | | ✓ | +++++ | ++++++ |
| | | ✓ | ✓ | +++ | ++++++ |
| | ✓ | ✓ | ✓ | ++++++++ | +++++++ |

*Traditional pharmaceutical formulation of bromocriptine mesylate as described in Table 1
[1]The bromocriptine may be micronized or not.
[2]each + represents a quantum improvement and a − represents no change.

Example 11

Procedure for Blending Formulations VS-55F-A, B, C, Formulation Guide for VS-55F-A

| Excipient Name | % Ratio | Weight (mg) | Excipients for 50 Tablets (gr.) |
|---|---|---|---|
| Bromocriptine mesylate | 1.50 | 1.500 | 0.075 |
| Citric Acid (Anhydrous) | 3.00 | 3.000 | 0.150 |
| HPC Klucel EF Pharm | 5.00 | 5.000 | 0.250 |
| Avicel Ph102 | 34.50 | 34.500 | 1.725 |
| Crosscarmellose Sodium | 7.00 | 7.000 | 0.350 |
| Mannitol | 47.00 | 47.000 | 2.350 |
| Fumed Silica | 1.00 | 1.000 | 0.050 |
| Stearic Acid | 1.00 | 1.000 | 0.050 |
| Total | 100.00 | 100.000 | 5.000 |

Procedure for Blending Formulation VS-55F-A:

A 50 ml round flask with cap was charged with 0.075 grams of Bromocriptine and 0.150 grams of Citric Acid. The mixture was then briskly shaken for a few seconds then it was placed in the roller where the blend was permitted to roll (at highest speed) for 10 minutes.

After rolling for 10 minutes blending was stopped and to the blend 0.250 grams of Klucel EF Pharm, 0.350 grams of crosscarmellos, and 0.050 fumed silica was added, The mixture was then briskly shaken for a few seconds then it was placed in the roller where the blend was permitted to roll (at highest speed) for 10 minutes.

After rolling for 10 minutes blending was stopped and to the blend 1.725 grams of Avicel PH 102, and 2.350 grams of Mannitol was added. The mixture was then briskly shaken for a few seconds then it was placed in the roller where the blend was permitted to roll (at highest speed) for 10 minutes.

shaken for a few seconds, then it was rolled at the highest speed for 5 minutes.

After rolling for two minutes the mixture was loaded into the feeder of the tablet press. The mixture was then pressed into tablets at the highest pressure tolerable for the TDP 1.5 (about 1.5 Tons of pressure). The tablet shape was a 6 mm convex round with an average weight of about 0.100+/−5% grams.

Formulation Guide for VS-55F-B

| Excipient Name | % Ratio | Weight (mg) | Excipients for 50 Tablets (gr.) |
|---|---|---|---|
| Bromocriptine Mesylate | 1.43 | 1.000 | 0.050 |
| Citric Acid (Anhydrous) | 3.00 | 2.100 | 0.105 |
| HPC Klucel EF Pharm | 5.00 | 3.500 | 0.175 |
| Avicel Ph102 | 34.57 | 24.200 | 1.210 |
| Crosscarmellose Sodium | 7.00 | 4.900 | 0.245 |
| Mannitol | 47.00 | 32.900 | 1.645 |
| Fumed Silica | 1.00 | 0.700 | 0.035 |
| Stearic Acid | 1.00 | 0.700 | 0.035 |
| Total | 100.00 | 70.000 | 3.500 |

Procedure for Blending Formulation VS-55F-B:

A 50 ml round flask with cap was charged with 0.050 grams of Bromocriptine and 0.105 grams of Citric Acid. The mixture was then briskly shaken for a few seconds then it was placed in the roller where the blend was permitted to roll (at highest speed) for 10 minutes.

After rolling for 5 minutes blending was stopped and to the blend 0.175 grams of Klucel EF Pharm, 0.245 grams of crosscarmellos, and 0.035 grams of fumed silica was added. The mixture was then briskly shaken for a few seconds then it was placed in the roller where the blend was permitted to roll (at highest speed) for 5 minutes.

After rolling for 5 minutes blending was stopped and to the blend 1.725 grams of Avicel PH 102, and 1.645 grams of mannitol was added. The mixture was then briskly shaken for a few seconds then it was placed in the roller where the blend was permitted to roll (at highest speed) for 5 minutes.

After rolling for 5 minutes blending was stowed and to the blend 0.035 grams of stearic acid was added. After the addition of the stearic acid the mixture was then briskly shaken for a few seconds, then it was rolled at the highest speed for five minutes.

After rolling for five minutes the mixture was loaded into the feeder of the tablet press. The mixture was then pressed into tablets at the lightest pressure tolerable for the TDP 1.5 (about 1.5 Tons of pressure). The tablet shape was a 6 mm convex round with an average weight of about 0.070+/−5% grams.

Results and Observations for VS-55F-B:

The hardness of the formulation was about 6.0-6.9 KP. The appearance of the tablets were white in color. The disintegration time for this formulation was about 3.17-3.65 minutes. The flow properties of this granulation mixture was suitable for use in a gravity feed press. Content uniformity is not within specifications.

Formulation Guide for VS-55F-C

| Excipient Name | % Ratio | Weight (mg) | Excipients for 50 Tablets (gr.) |
|---|---|---|---|
| Bromocriptine Mesylate | 1.43 | 1.000 | 0.050 |
| Citric Acid (Anhydrous) | 3.00 | 2.100 | 0.105 |
| HPC Klucel EF Pharm | 3.57 | 2.500 | 0.125 |
| Avicel Ph102 | 34.57 | 24.200 | 1.210 |
| Crosscarmellose Sodium | 8.43 | 5.900 | 0.295 |
| Mannitol | 47.00 | 32.900 | 1.645 |
| Fumed Silica | 1.00 | 0.700 | 0.035 |
| Stearic Acid | 1.00 | 0.700 | 0.035 |
| Total | 100.00 | 70.000 | 3.500 |

Procedure for Blending Formulation VS-55F-C:

A 50 ml round flask with cap was charged with 0.050 grams of Bromocriptine and 0.105 grams of Citric Acid. The mixture was then briskly shaken for a few seconds then it was placed in the roller where the blend was permitted to roll (at highest speed) for 10 minutes.

After rolling for 5 minutes blending was stopped and to the blend 0.125 grams of Klucel EF Pharm, 0.295 grains of crosscarmellos, and 0.035 grams of fumed silica was added. The mixture was then briskly shaken for a few seconds then it was placed in the roller where the blend was permitted to roll (at highest speed) for 5 minutes.

After rolling for 5 minutes blending was stowed and to the blend 1.210 grams of Avicel PH 102, and 1.645 grams of mannitol was added. The mixture was then briskly shaken for a few seconds then it was placed in the roller where the blend was permitted to roll (at highest speed) for 5 minutes.

After rolling for 5 minutes blending was stopped and to the blend 0.035 grams of stearic acid was added. After the addition of the stearic acid the mixture was then briskly shaken for a few seconds, then it was rolled at the highest speed for five minutes.

After rolling for five minutes the mixture was loaded into the feeder of the tablet press. The mixture was then pressed into tablets at the highest pressure tolerable for the TDP1.5 (about 1.5 Tons of pressure). The tablet shape was a 6 mm convex round with an average weight of about 0.070+/−5% grams.

Results and Observations for VS-54F-C:

The hardness of the formulation was about 7-8 KP. The appearance of the tablets were white in color. The disintegration time for this formulation was about 3.17-3.83 minutes. The flow properties of this granulation mixture was suitable for use in a gravity feed press. Content uniformity is within specifications.

Formulation Guide for VS-55F-D (53F-D.1)

| Excipient Name | % Ratio | Weight (mg) | Excipients for 50 Tablets (gr.) |
|---|---|---|---|
| VS1001 | 1.50 | 1.500 | 0.075 |
| Citric Acid (Anhydrous) | 3.00 | 3.000 | 0.150 |
| HPC Klucel EF Pharm | 5.00 | 5.000 | 0.250 |
| Avicel Ph102 | 34.50 | 34.500 | 1.725 |
| Crosscarmellose Sodium | 7.00 | 7.000 | 0.350 |
| Sorbitol | 47.00 | 47.000 | 2.350 |
| Fumed Silica | 1.00 | 1.000 | 0.050 |
| Stearic Acid | 1.00 | 1.000 | 0.050 |
| Total | 100.00 | 100.000 | 5.000 |

Procedure for Blending Formulation VS-55F-D:

A 50 ml round flask with cap was charged with 0.075 grams of Bromocriptine and 0.150 grams of Citric Acid. The mixture was then briskly shaken for a few seconds then it was placed in the roller where the blend was permitted to roll (at highest speed) for 10 minutes.

After rolling for 10 minutes blending was stopped and to the blend 0.250 grams of Klucel EF Pharm, 0.350 grams of crosscarmellos, and 0.050 fumed silica was added, The mixture was then briskly shaken for a few seconds then it was placed in the roller where the blend was permitted to roll (at highest speed) for 10 minutes.

After rolling for 10 minutes blending was stopped and to the blend 1.725 grams of Avicel PH 102, and 2.350 grams of sorbitol was added. The mixture was then briskly shaken for a few seconds then it was placed in the roller where the blend was permitted to roll (at highest speed) for 10 minutes.

After rolling for 10 minutes blending was stopped and to the blend 0.050 grams of stearic acid was added. After the addition of the stearic acid the mixture was then briskly shaken for a few seconds, then it was rolled at the highest speed for 5 minutes.

After rolling for two minutes the mixture was loaded into the feeder of the tablet press. The mixture was then pressed into tablets at the highest pressure tolerable for the TDP 1.5 (about 1.5 Tons of pressure). The tablet shape was a 6 mm convex round with an average weight of about 0.100+/−5% grams.

After completing the run hardness tests, disintegration tests, and observations were made.

Results and Observations for VS-54F-B.1:

The hardness of the formulation was about 16-16.5 KP. The appearance of the tablets were white in color. The disintegration time for this formulation was about 8.67-9.0 minutes. The flow properties of this granulation mixture was suitable for use in a gravity feed press. Content uniformity is within specifications.

Procedure for Blending Formulations VS-56F-A, B, C, D, E, and F:

Formulation Guide for VS 56F-A

| Excipient Name | % Ratio | Weight (mg) | Excipients for 50 Tablets (gr.) |
|---|---|---|---|
| Bromocriptine Mesylate | 1.43 | 1.000 | 0.050 |
| Citric Acid (Anhydrous) | 3.00 | 2.100 | 0.105 |
| Menthol | 0.50 | 0.350 | 0.018 |
| HPC Klucel EF Pharm | 5.00 | 3.500 | 0.175 |
| Avicel Ph102 | 34.07 | 23.850 | 1.193 |
| Crosscarmellose Sodium | 7.00 | 4.900 | 0.245 |
| Mannitol | 47.00 | 32.900 | 1.645 |
| Fumed Silica | 1.00 | 0.700 | 0.035 |
| Stearic Acid | 1.00 | 0.700 | 0.035 |
| Total | 100.00 | 70.000 | 3.500 |

Procedure for Blending Formulation VS-56F-A:

A 50 ml round flask with cap was charged with 0.050 grams of Bromocriptine 0.105 grams of Citric Acid, 0.018 grams of menthol, and 0.175 grams of Klucel EF Pharm. The mixture was then briskly shaken for a few seconds then it was placed in the roller where the blend was permitted to roll (at highest speed) for 5 minutes.

After rolling for 5 minutes blending was stopped and to the blend 1.193 grams of Avicel PH 102, 0.245 grams of crosscarmellos, and 0.035 grams of fumed silica was added, The mixture was then briskly shaken for a few seconds then it was placed in the roller where the blend was permitted to roll (at highest speed) for 5 minutes.

After rolling for 5 minutes blending was stopped and to the blend, and 1.645 grams of Mannitol was added. The mixture was then briskly shaken for a few seconds then it was placed in the roller where the blend was permitted to roll (at highest speed) for 5 minutes.

After rolling for 5 minutes blending was stopped and to the blend 0.035 grams of stearic acid was added. After the addition of the stearic acid the mixture was then briskly shaken for a few seconds, then it was rolled at the higher speed for 5 minutes.

After rolling for five minutes the mixture was loaded into the feeder of the tablet press. The mixture was then pressed into tablets at a pressure lower than the maximum for the TDP 1.5 (about 0.75 Tons of pressure). The tablet shape was a 6 mm flat round with an average weight of about 0.070+/−5% grams.

After completing the run hardness tests, disintegration tests, and observations were made Results and Observations for VS-56F-A:

The hardness of the formulation was about 2.8 KP. The appearance of the tablets were white in color. The disintegration time for this formulation was about 1.5 minutes. The flow properties of this granulation mixture was suitable for use in a gravity feed press. Content uniformity was within specifications.

Conclusion for VS-56F-A:

Formulation meets content uniformity and disintegration specifications. Tablet formulation will be evaluated for release of API.

Formulation Guide for VS-56F-B

| Excipient Name | % Ratio | Weight (mg) | Excipients for 50 Tablets (gr.) |
|---|---|---|---|
| Bromocriptine Mesylate | 2.14 | 1.500 | 0.075 |
| Citric Acid (Anhydrous) | 3.00 | 2.100 | 0.105 |
| Menthol | 0.50 | 0.350 | 0.018 |
| HPC Klucel EF Pharm | 5.00 | 3.500 | 0.175 |
| Avicel Ph102 | 33.36 | 23.350 | 1.168 |
| Crosscarmellose Sodium | 7.00 | 4.900 | 0.245 |
| Mannitol | 47.00 | 32.900 | 1.645 |
| Fumed Silica | 1.00 | 0.700 | 0.035 |
| Stearic Acid | 1.00 | 0.700 | 0.035 |
| Total | 100.00 | 70.000 | 3.500 |

Procedure for Blending Formulation VS-56F-B:

A 50 ml round flask with cap was charged with 0.075 grams of Bromocriptine 0.105 grams of Citric Acid, 0.018 grams of menthol, and 0.175 grams of Klucel EF Pharm. The mixture was then briskly shaken for a few seconds then it was placed in the roller where the blend was permitted to roll (at highest speed) for 5 minutes.

After rolling for 5 minutes blending was stopped and to the blend 1.168 grams of Avicel PH 102, 0.245 grams of crosscarmellos, and 0.035 grams of fumed silica was added, The mixture was then briskly shaken for a few seconds then it was placed in the roller where the blend was permitted to roll (at highest speed) for 5 minutes.

After rolling for 5 minutes blending was stepped and to the blend, and 1.645 grams of Mannitol was added. The mixture was then briskly shaken for a few seconds then it was placed in the roller where the blend was permitted to roll (at highest speed) for 5 minutes.

After rolling for 5 minutes blending was stopped and to the blend 0.035 grams of stearic acid was added. After the addition of the stearic acid the mixture was then briskly shaken for a few seconds, then it was rolled at the highest speed for 5 minutes.

After rolling for five minutes the mixture was loaded into the feeder of the tablet press. The mixture was then pressed into tablets at a pressure lower than the maximum for the TDP 1.5 (about 1.5 Tons of pressure). The tablet shape was a 6 mm flat round with an average weight of about 0.070+/−5% grams.

After completing the run hardness tests, disintegration tests, and observations were made.

Results and Observations for VS-56F-B:

The Hardness of the Formulation was about 3.9 KP. The Appearance of the tablets were white in color. The disintegration time for this formulation was about 1.38 minutes. The flow properties of this granulation mixture was suitable for use in a gravity feed press. Content uniformity is within specifications.

Conclusion for VS-56F-B:

Formulation meets content uniformity and disintegration specifications. Tablet formulation will be evaluated for release of API.

Formulation Guide for VS-56F-C

| Excipient Name | % Ratio | Weight (mg) | Excipients for 50 Tablets (gr.) |
|---|---|---|---|
| VS1001 | 1.43 | 1.000 | 0.050 |
| Citric Acid (Anhydrous) | 3.00 | 2.100 | 0.105 |
| Menthol | 0.50 | 0.350 | 0.018 |
| HPC Klucel EF Pharm | 5.00 | 3.500 | 0.175 |
| Avicel Ph102 | 34.07 | 23.850 | 1.193 |

-continued

| Excipient Name | % Ratio | Weight (mg) | Excipients for 50 Tablets (gr.) |
|---|---|---|---|
| Explotab | 7.00 | 4.900 | 0.245 |
| Mannitol | 47.00 | 32.900 | 1.645 |
| Fumed Silica | 1.00 | 0.700 | 0.035 |
| Stearic Acid | 1.00 | 0.700 | 0.035 |
| Total | 100.00 | 70.000 | 3.500 |

Procedure for Blending Formulation VS-56F-C:

A 50 ml round flask with cap was charged with 0.050 grams of Bromocriptine 0.105 grams of Citric Acid, 0.018 grams of menthol, and 0.175 grams of Klucel EF Pharm). The mixture was then briskly shaken for a few seconds then it was placed in the roller where the blend was permitted to roll (at highest speed) for 5 minutes.

After rolling for 5 minutes blending was stopped and to the blend 1.193 grams of Avicel PH 102, 0.245 grams of crosscarmellos, and 0.035 grams of fumed silica was added, The mixture was then briskly shaken for a few seconds then it was placed in the roller where the blend was permitted to roll (at highest speed) for 5 minutes.

After rolling for 5 minutes blending was stopped and to the blend, and 1.645 grams of Mannitol was added. The mixture was then briskly shaken for a few seconds then it was placed in the roller where the blend was permitted to roll (at highest speed) for 5 minutes.

After rolling for 5 minutes blending was stopped and to the blend 0.035 grams of stearic acid was added. After the addition of the stearic acid the mixture was then briskly shaken for a few seconds, then it was rolled at the highest speed for 5 minutes.

After rolling for five minutes the mixture was loaded into the feeder of the tablet press. The mixture was then pressed into tablets at a pressure lower than the maximum for the TDP 1.5 (about 1.5 Tons of pressure). The tablet shape was a 6 mm flat round with an average weight of about 0.070+/−5% grams.

After completing the run hardness tests, disintegration tests, and observations were made.

Results and Observations for VS-56F-C

The hardness of the formulation was about 3-3.5 KP. The appearance of the tablets were white in color. The disintegration time for this formulation was about 1.33 minutes. The flow properties of this granulation mixture was suitable for use in a gravity feed press. Content uniformity is within specifications.

Conclusion for VS-56F-C:

Formulation meets content uniformity and disintegration specifications. Tablet formulation will be evaluated for release of API.

Formulation Guide for VS-56F-D

| Excipient Name | % Ratio | Weight (mg) | Excipients for 50 Tablets (gr.) |
|---|---|---|---|
| VS1001 | 1.43 | 1.000 | 0.050 |
| Citric Acid (Anhydrous) | 3.00 | 2.100 | 0.105 |
| PEG 3350 | 0.14 | 0.100 | 0.005 |
| HPC Klucel EF Pharm | 5.00 | 3.500 | 0.175 |
| Avicel Ph102 | 34.43 | 24.100 | 1.205 |

-continued

| Excipient Name | % Ratio | Weight (mg) | Excipients for 50 Tablets (gr.) |
|---|---|---|---|
| Explotab | 7.00 | 4.900 | 0.245 |
| Mannitol | 47.00 | 32.900 | 1.645 |
| Fumed Silica | 1.00 | 0.700 | 0.035 |
| Stearic Acid | 1.00 | 0.700 | 0.035 |
| Total | 100.00 | 70.000 | 3.500 |

Procedure for Blending Formulation VS-56F-D:

A 50 ml round flask with cap was charged with 0.050 grams of Bromocriptine 0.105 grams of Citric Acid, 0.005 grams of PEG 3350, and 0.175 grams of Klucel EF Pharm. The mixture was then briskly shaken for a few seconds then it was placed in the roller where the blend was permitted to roll (at highest speed) for 5 minutes.

After rolling for 5 minutes blending was stooped and to the blend 1.205 grams of Avicel PH 102, 0.245 grams of crosscarmellos, and 0.035 grams of fumed silica was added, The mixture was then briskly shaken for a few seconds then was placed in the roller where the blend was permitted to roll (at highest speed) for 5 minutes.

After rolling for 5 minutes blending was stepped and to the blend, and 1.645 grams of Mannitol was added. The mixture was then briskly shaken for a few seconds then it was placed in the roller where the blend was permitted to roll (at highest speed) for 5 minutes.

After rolling for 5 minutes blending was stopped and to the blend 0.035 grams of stearic acid was added. After the addition of the stearic acid the mixture was then briskly shaken for a few seconds, then it was rolled at the highest speed for 5 minutes.

After rolling for five minutes the mixture was loaded into the feeder of the tablet press. The mixture was then pressed into tablets at a pressure lower than the maximum for the TDP 1.5 (about 1.5 Tons of pressure). The tablet shape was a 6 mm flat round with an average weight of about 0.070+/−5% grams.

After completing the run hardness tests, disintegration tests, and observations were made.

Results and Observations for VS-56F-D:

The hardness of the formulation was about 3.8 KP. The appearance of the tablets were white in color. The disintegration time for this formulation was about 1.08 minutes. The flow properties of this granulation mixture was suitable for use in a gravity feed press. Content uniformity is within specifications.

Conclusion for VS-56F-D:

Formulation meets content uniformity and disintegration specifications. Tablet formulation will be evaluated for release of API.

Formulation Guide for VS-56F-E

| Excipient Name | % Ratio | Weight (mg) | Excipients for 50 Tablets (gr.) |
|---|---|---|---|
| VS1001 | 2.14 | 1.500 | 0.075 |
| Citric Acid (Anhydrous) | 3.00 | 2.100 | 0.105 |
| Menthol | 0.50 | 0.350 | 0.018 |
| HPC Klucel EF Pharm | 5.00 | 3.500 | 0.175 |
| Avicel Ph102 | 33.36 | 23.350 | 1.168 |
| Explotab | 7.00 | 4.900 | 0.245 |

-continued

| Excipient Name | % Ratio | Weight (mg) | Excipients for 50 Tablets (gr.) |
|---|---|---|---|
| Mannitol | 47.00 | 32.900 | 1.645 |
| Fumed Silica | 1.00 | 0.700 | 0.035 |
| Stearic Acid | 1.00 | 0.700 | 0.035 |
| Total | 100.00 | 70.000 | 3.500 |

Procedure for Blending Formulation VS-56F-E:

A 50 ml round flask with cap was charged with 0.075 grams of Bromocriptine 0.105 grams of Citric Acid, 0.018 grams of menthol, and 0.175 grams of Klucel EF Pharm. The mixture was then briskly shaken for a few seconds then it was placed in the roller where the blend was permitted to roll (at highest speed) for 5 minutes.

After rolling for 5 minutes blending was stopped and to the blend 1.168 grams of Avicel PH 102, 0.245 grams of Explotab, and 0.035 grams of fumed silica was added, The mixture was then briskly shaken for a few seconds then it was placed in the roller where the blend was permitted to roll (at highest speed) for 5 minutes.

After rolling for 5 minutes blending was stopped and to the blend, and 1.645 grams of Mannitol was added. The mixture was then briskly shaken for a few seconds then it was placed in the roller where the blend was permitted to roll (at highest speed) for 5 minutes.

After rolling for 5 minutes blending was stopped and to the blend 0.035 grams of stearic acid was added. After the addition of the stearic acid the mixture was then briskly shaken for a few seconds, then it was rolled at the highest speed for 5 minutes.

After rolling for five minutes the mixture was loaded into the feeder of the tablet press. The mixture was then pressed into tablets at a pressure lower than the maximum for the TDP 1.5 (about 1.5 Tons of pressure). The tablet shade was a 6 mm flat round with an average weight of about 0.070+/−5% grams.

After completing the run hardness tests, disintegration tests, and observations were made.

Results and Observations for VS-56F-E:

The hardness of the formulation was about 4.0 KP. The appearance of the tablets were white in color. The disintegration time for this formulation was about 1.5 minutes. The flow properties of this granulation mixture was suitable for use in a gravity feed press. Content uniformity is within specifications.

Conclusion for VS-56F-E:

Formulation meets content uniformity and disintegration specifications. Tablet formulation will be evaluated for release of API.

Formulation Guide for VS-56F-F

| Excipient Name | % Ratio | Weight (mg) | Excipients for 50 Tablets (gr.) |
|---|---|---|---|
| VS1001 | 1.43 | 1.000 | 0.050 |
| Citric Acid (Anhydrous) | 3.00 | 2.100 | 0.105 |
| Menthol | 0.50 | 0.350 | 0.018 |
| PEG 3350 | 0.14 | 0.100 | 0.005 |
| HPC Klucel EF Pharm | 5.00 | 3.500 | 0.175 |
| Avicel Ph102 | 33.93 | 23.750 | 1.188 |
| Crosscarmellose Sodium | 7.00 | 4.900 | 0.245 |

-continued

| Excipient Name | % Ratio | Weight (mg) | Excipients for 50 Tablets (gr.) |
|---|---|---|---|
| Mannitol | 47.00 | 32.900 | 1.645 |
| Fumed Silica | 1.00 | 0.700 | 0.035 |
| Stearic Acid | 1.00 | 0.700 | 0.035 |
| Total | 100.00 | 70.000 | 3.500 |

Procedure for Blending Formulation VS-56F-F:

A 50 ml round flask with cap was charged with 0.050 grams of Bromocriptine 0.105 grams of Citric Acid, 0.018 grams of menthol, 0.005 grams of PEG 3350, and 0.175 grams of Klucel EF Pharm. The mixture was then briskly shaken for a few seconds then it was placed in the roller where the blend was permitted to roll (at highest speed) for 5 minutes.

After rolling for 5 minutes blending was stopped and to the blend 1.188 grams of Avicel PH 102, 0.245 grams of crosscarmellos, and 0.035 grams of fumed silica was added, The mixture was then briskly shaken for a few seconds then it was placed in the roller where the blend was permitted to roll (at highest speed) for 5 minutes.

After rolling for 5 minutes blending was stopped and to the blend, and 1.645 grams of Mannitol was added. The mixture was then briskly shaken for a few seconds then it was placed in the roller where the blend was permitted to roll (at highest speed) for 5 minutes.

After rolling for 5 minutes blending was stopped and to the blend 0.035 grams of stearic acid was added. After the addition of the stearic acid the mixture was then briskly shaken for a few seconds, then it was rolled at the highest speed for 5 minutes.

After rolling for five minutes the mixture was loaded into the feeder of the tablet press. The mixture was then pressed into tablets at a pressure lower than the maximum for the TDP 1.5 (about 1.5 Tons of pressure). The tablet shade was a 6 mm flat round with an average weight of about 0.070+/−5% grams.

After completing the run hardness tests, disintegration tests, and observations were made.

Results and Observations for VS-56F-F:

The hardness of the formulation was about 3.8 KP. The appearance of the tablets were white in color. The disintegration time for this formulation was about 1.5 minutes. The flow properties of this granulation mixture was suitable for use in a gravity feed press. Content uniformity is within specifications.

Conclusion for VS-56F-F:

Formulation meets content uniformity and disintegration specifications. Tablet formulation will be evaluated for release of API Example 11

Two dissolution studies were performed on the tablet formulations produced in this project as shown below (set 1 and 2):

$1^{st}$ Set (4 Tablets)
VS-ER-NL-55F-A (1.5% BC)
VS-ER-NL-55F-B (1.43% BC)
VS-ER-NL-55F-C (1.43% BC)
VS-ER-NL-55F-D.1. (1.5% BC)

$2^{nd}$ Set (6 Tablets)
VS-ER-NL-56F-A (1.43% BC)
VS-ER-NL-56F-B (2.14% BC)

VS-ER-NL-56F-C (1.43% BC)
VS-ER-NL-56F-D (1.43% BC)
VS-ER-NL-56F-E (2.14% BC)
VS-ER-NL-56F-E (1.43% BC)
HPLC Method Description:

The following describes the HPLC conditions (instrument, settings, etc.) for the analysis of the samples.

Column: Waters Symmetry Shield RP18, 3.5 micron 4.6×150 min P/N 186000180 Mobile Phase A: 0.1% TEA Water Mobile Phase B: 0.1% TFA Acetonitrile Gradient:

| Time | % B |
|------|-----|
| 0 | 20 |
| 5 | 35 |
| 20 | 40 |
| 21 | 20 |
| 25 | 20 |

Flow: 1 ml/min Detection

UV: 300 nm Diluent: 0.5%

Citric Acid

Column Oven Temperature: 30° C.

Injection Volume: 100 microliters

Sample tray at 5° C.

HPLC Standards Preparation

A primary stock solution was prepared by accurately weighing and dissolving 30 mg of BC in a 25 ml volumetric flask. (Diluent—0.5% citric acid) (About 1.2 mg/ml)

A secondary stock solution was prepared by taking 1 ml of the primary stock and diluting to 10 mls in a volumetric flask. (About 0.12 mg/m:)

Different volumes of the secondary stock solution were taken into separate 10 ml volumetric flasks to prepare the standards that were directly injected for the calibration curve. The volumes and approximate concentrations are shown below;

0.125 ml=about 0.0015 mg/ml 0.250 ml=about 0.003 mg/nil 0.500 ml=about 0.006 mg/nil 1.000 ml=about 0.012 mg/ml 1.500 ml=about 0.018 mg/ml A spreadsheet was developed to plot the area vs. concentrations of the standards. The slope and intercept of this line equation was used to calculate the concentrations of each of the pull points in the dissolution runs.

Dissolution Method

From each of the lots described above, 11 tablets were weighed and added to 1000 ml of 0.5% citric acid solution at 37° C. The dissolution apparatus was setup with paddles at 100 RPM. (Apparatus 2)

For the 1$^{st}$ series of experiments described above, samples were pulled at 5, 10, 15, 20, 30, 45 and 60 minutes. The pull points for the second series of experiments were more frequent and were done at earlier time points in an attempt to capture the faster drug release. These time points were as follows: 5, 7.5, 10, 15, 30 and 60.

For each pull point, about 1 ml of the solution was sampled. The samples were centrifuged to remove any particles and the supernatant was directly injected.

The solubility curves were plotted in the spreadsheet. The concentration was determined using the calibration curve and the percent release determined using the total weight of the 11 tablets and the percent BC.

Dissolution Test Results for 55F and 56F

Series 55F Series Results:

1$^{st}$ Set (4 Tablets)

VS-ER-NL-55F-A (1.5% BC)

VS-ER-NL-55F-B (1,43% BC)

VS-ER-NL-55F-C (1.43% BC)

VS-ER-NL-55F-D.1 (1.5% BC)

Figure 4:
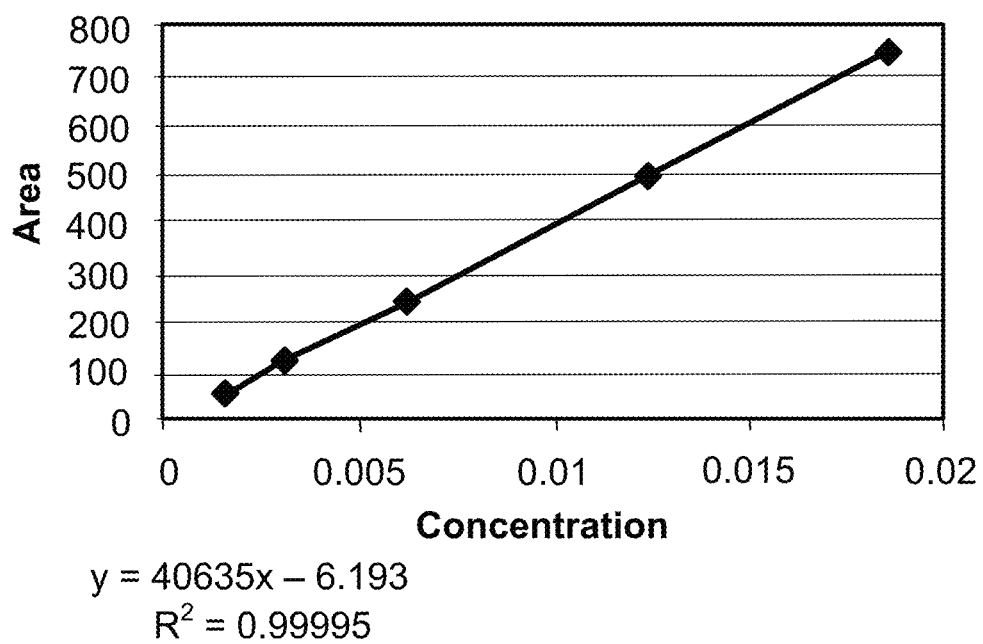
FIG. 4 is a graph of Calibration curve for 55F Series Dissolution Tests.

See FIG. 4 for a Calibration curve for the 55F Series Dissolution Tests.

TABLE 1

Dissolution Test Results for VS-ER-NL-55F-A (1.5% BC)

| Time Minutes | Area | Vial Concentration | Concentration (mg) | % Theory Release |
|---|---|---|---|---|
| 5 | 616.8 | 0.015331526 | 15.33 | 92.38 |
| 10 | 661.1 | 0.016421725 | 16.42 | 98.95 |
| 15 | 667.8 | 0.016586608 | 16.59 | 99.94 |
| 20 | 665.9 | 0.016539851 | 16.54 | 99.66 |
| 30 | 666.4 | 0.016552155 | 16.55 | 99.74 |
| 45 | 669.0 | 0.01661614 | 16.62 | 100.12 |

Figure 5:
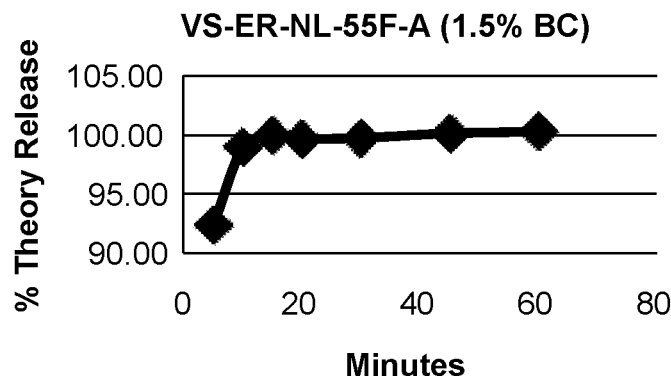
FIG. 5 is a graph of Dissolution Test Results for VS-ER-NL-55F-A (1.5% BC).

See FIG. 5 for a Graph of Dissolution Test Results for VS-ER-NL-55F-A (1.5% BC).

Conclusion for VS-ER-NL-55F-A (1.5% PC):

Tablet will be submitted for use in animal studies.

TABLE 2

Dissolution Test Results for VS-ER-NL-55F-B (1.43% BC)

| Time Minutes | Area | Vial Concentration | Concentration (mg) | % Theory Release |
|---|---|---|---|---|
| 5 | 425.9 | 0.010633579 | 10.63 | 95.80 |
| 10 | 434.7 | 0.010850142 | 10.85 | 97.75 |
| 15 | 437.3 | 0.010914127 | 10.91 | 98.33 |
| 20 | 436.5 | 0.010894439 | 10.89 | 98.15 |
| 30 | 435.8 | 0.010877212 | 10.88 | 98.00 |
| 45 | 435.4 | 0.010867369 | 10.87 | 97.91 |
| 60 | 436.1 | 0.010884595 | 10.88 | 98.06 |

Figure 6:
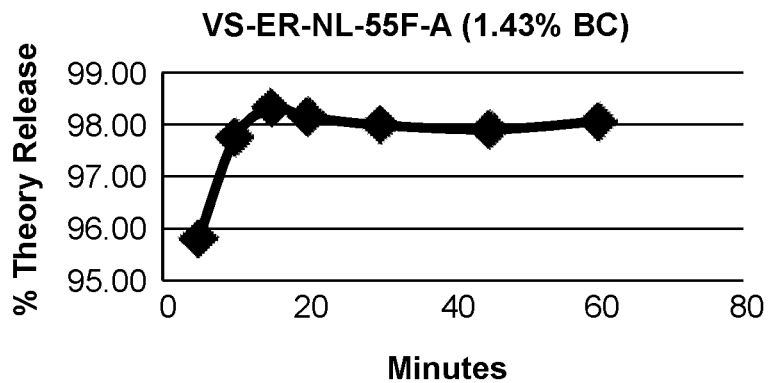
FIG. 6 is a graph of Dissolution Test Results for VS-ER-NL-55F-B (1.43% BC).

See FIG. 6 for a Graph of Dissolution Test Results for VS-ER-NL-55F-B (1.43% BC)

Conclusion for VS-ER-NL-55F-B (1.43% BC):

Tablet will be submitted for use in animal studies.

TABLE 3

Dissolution Test Results for VS-ER-NL-55F-C (1.43%) BC)

| Time Minutes | Area | Vial Concentration | Concentration (mg) | % Theory Release |
|---|---|---|---|---|
| 5 | 437.3 | 0.010914127 | 10.91 | 99.02 |
| 10 | 442.7 | 0.011047018 | 11.05 | 100.22 |
| 15 | 439.3 | 0.010963346 | 10.96 | 99.46 |
| 20 | 441.5 | 0.011017486 | 11.02 | 99.96 |
| 30 | 442.7 | 0.011047018 | 11.05 | 100.22 |
| 45 | 441.9 | 0.01102733 | 11.03 | 100.04 |

Figure 7:
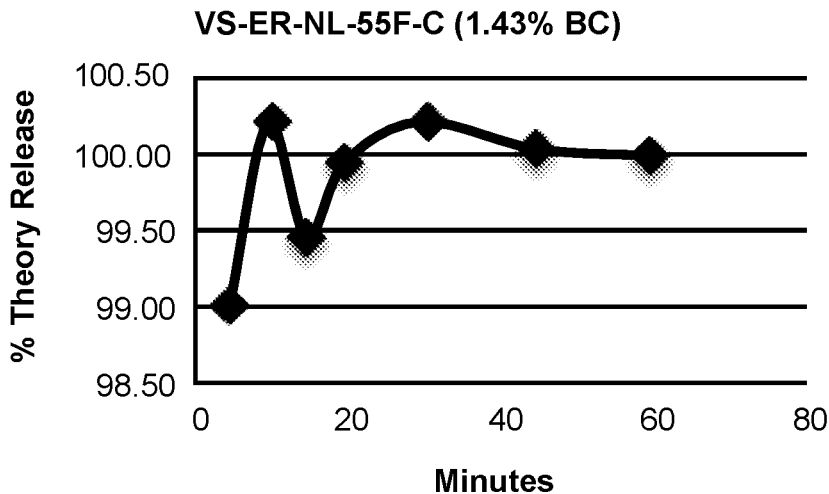
FIG. 7 is a graph of Dissolution Test Results for VS-ER-NL-55F-C (1.43% BC).

See FIG. 7 for a Graph of Dissolution Test Results for VS-ER-NL-55F-C (1.43% BC).

TABLE 4

Dissolution Test Results for VS-ER-NL-55F-D (1.43% BC)

| Time Minutes | Area | Vial Concentration | Concentration (mg) | % Theory Release |
|---|---|---|---|---|
| 5 | 389 | 0.009725489 | 9.73 | 59.02 |
| 10 | 579.9 | 0.014423436 | 14.42 | 87.53 |
| 15 | 596.5 | 0.014831954 | 14.83 | 90.01 |
| 20 | 603 | 0.014991915 | 14.99 | 90.98 |
| 30 | 608.4 | 0.015124806 | 15.12 | 91.79 |
| 45 | 616.2 | 0.01531676 | 15.32 | 92.96 |

Figure 8:
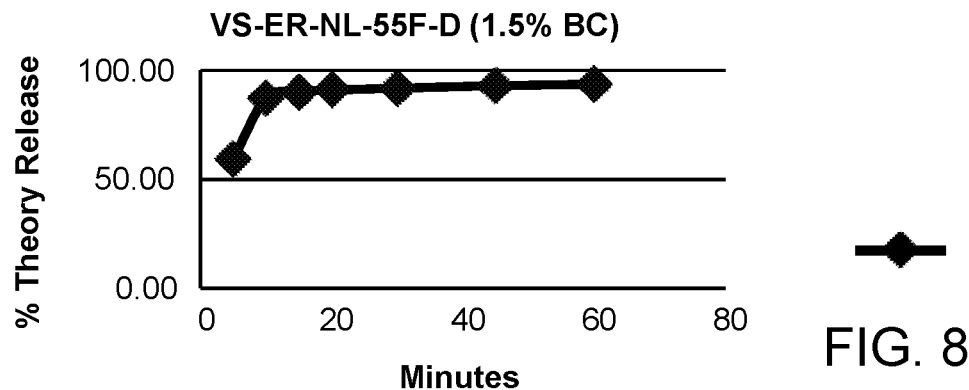
FIG. 8 is a graph of Dissolution Test Results for VS-ER-NL-55F-D (1.5% BC).

See FIG. 8 for a Graph of Dissolution Test Results for VS-ER-NL-55F-D (1.5% BC).

Conclusion for VS-ER-NL-55F-D (1.5% BC):

Tablet performs in the same manner as in previous experiment.

56F Series Results:

$2^{nd}$ Set (6 Tablets)

VS-ER-NL-56F-A (1.43% BC)

VS-ER-NL-56F-B (2.14% BC)

VS-ER-NL-56F-C (1.43% BC)

VS-ER-NL-56F-D (1.43% BC)

VS-ER-NL-56F-E (2.14% BC)

VS-ER-NL-56F-F (1.43% BC)

Figure 9:
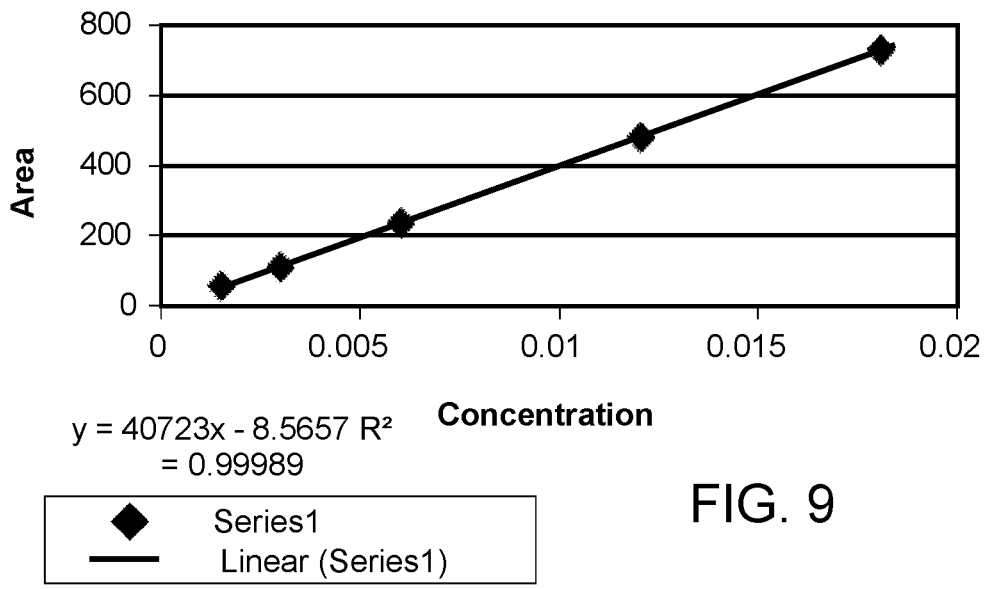
FIG. 9 is a Calibration Curve for 56F Series Dissolution Tests.

See FIG. 9 for a Calibration Curve for 56F Series Dissolution Tests.

TABLE 5

Dissolution Test Results for VS-ER-NL-56F-A (1.43% BC)

| Time Minutes | Area | Vial Concentration | Concentration (mg) | % Theory Release |
|---|---|---|---|---|
| 2 | 395.7 | 0.009927212 | 9.93 | 87.29 |
| 5 | 429.7 | 0.010762121 | 10.76 | 94.63 |
| 7.5 | 425.4 | 0.010656529 | 10.66 | 93.70 |
| 10 | 420 | 0.010523926 | 10.52 | 92.54 |
| 15 | 422.4 | 0.010582861 | 10.58 | 93.05 |
| 30 | 428.5 | 0.010732653 | 10.73 | 94.37 |
| 60 | 434.4 | 0.010877535 | 10.88 | 95.65 |

Figure 10:
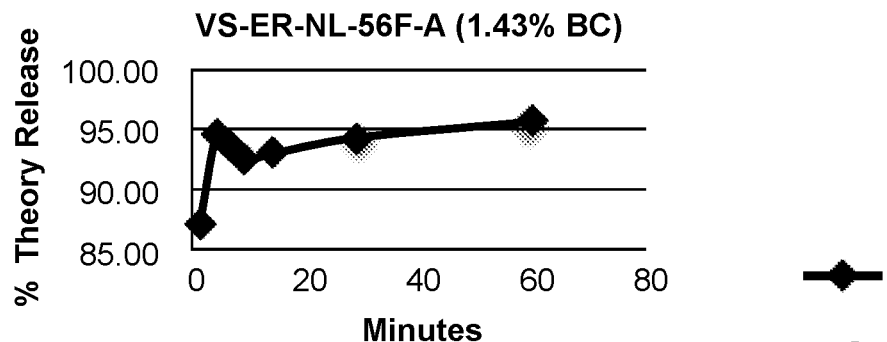
FIG. 10 is a graph of Dissolution Test Results for VS-ER-NL-56F-A (1.43% BC).

See FIG. 10 for a Graph of Dissolution Test Results for VS-ER-NL-56F-A (1.43% BC).

Conclusion for VS-ER-NL-56F-B (2.14% BC):

Tablet will be submitted for animal testing

Graph 6: Dissolution Test Results for VS-ER-NL-56F-B (2.14% BC)

| Time Minutes | Area | Vial Concentration | Concentration (mg) | % Theory Release |
|---|---|---|---|---|
| 2 | 618.1 | 0.0153885 | 15.39 | 92.16 |
| 5 | 638.4 | 0.01588699 | 15.89 | 95.14 |
| 7.5 | 643.4 | 0.016009771 | 16.01 | 95.88 |
| 10 | 650.1 | 0.016174297 | 16.17 | 96.86 |
| 15 | 655.3 | 0.016301989 | 16.30 | 97.63 |
| 30 | 665.6 | 0.016554917 | 16.55 | 99.14 |
| 60 | 671.4 | 0.016697343 | 16.70 | 99.99 |

Figure 11:
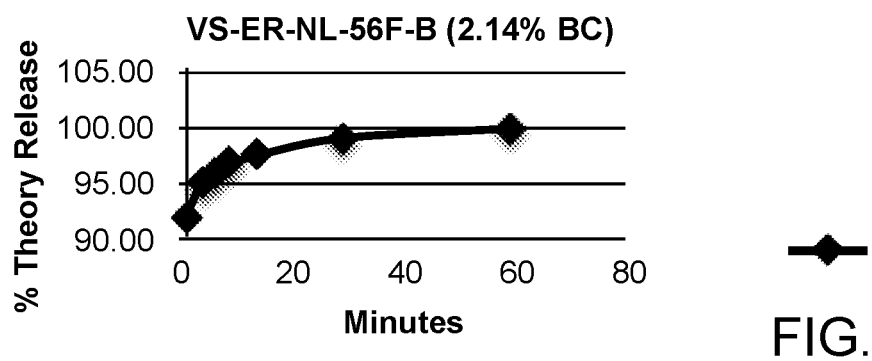
FIG. 11 is a graph of Dissolution Test Results for VS-ER-NL-56F-B (2.14% BC).

See FIG. 11 for a Graph of Dissolution Test Results for VS-ER-NL-56F-B (2.14% BC).

Tablet will be submitted for animal testing.

TABLE 7

Dissolution Test Results for VS-ER-NL-56F-C (1.43% BC)

| Time Minutes | Area | Vial Concentration | Concentration (mg) | % Theory Release |
|---|---|---|---|---|
| 2 | 491.3 | 0.01227478 | 12.27 | 119.58 |
| 5 | 429 | 0.010744931 | 10.74 | 104.68 |
| 7.5 | 431.2 | 0.010798955 | 10.80 | 105.21 |
| 10 | 434.2 | 0.010872623 | 10.87 | 105.92 |
| 15 | 461.2 | 0.01153564 | 11.54 | 112.38 |
| 30 | 443.8 | 0.011108363 | 11.11 | 108.22 |
| 60 | 444.4 | 0.011123096 | 11.12 | 108.36 |

Figure 12:
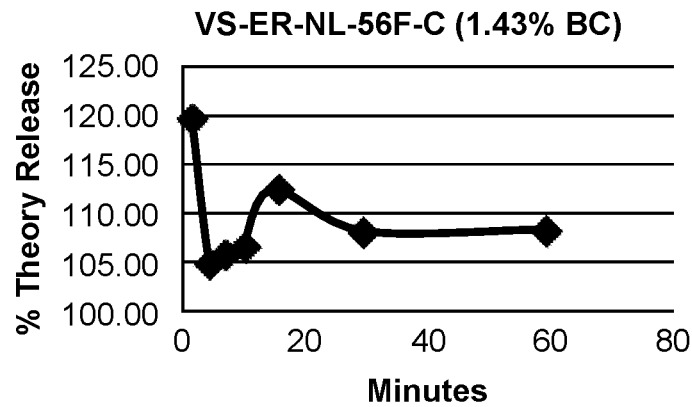
FIG. 12 is a graph of Dissolution Test Results for VS-ER-NL-56F-C (1.43% BC).

See FIG. 12 for a Graph of Dissolution Test Results for VS-ER-NL-56F-C (1.43% BC).

Conclusion for VS-ER-NL-56F-C (1.43% BC):

Tablet will be submitted for animal testing.

HPLC and Dissolution Method and Test Results

TABLE 8

Dissolution Test Results for VS-ER-NL-56F-D (1.43% BC)

| Time Minutes | Area | Vial Concentration | Concentration (mg) | % Theory Release |
|---|---|---|---|---|
| 2 | 372.5 | 0.009357509 | 9.36 | 83.43 |
| 5 | 444.2 | 0.011118185 | 11.12 | 99.13 |
| 7.5 | 454.4 | 0.011368658 | 11.37 | 101.37 |
| 10 | 457.3 | 0.011439871 | 11.44 | 102.00 |
| 15 | 457.9 | 0.011454604 | 11.45 | 102.13 |
| 30 | 459.5 | 0.011493894 | 11.49 | 102.48 |
| 60 | 459 | 0.011481616 | 11.48 | 102.37 |

Figure 13:
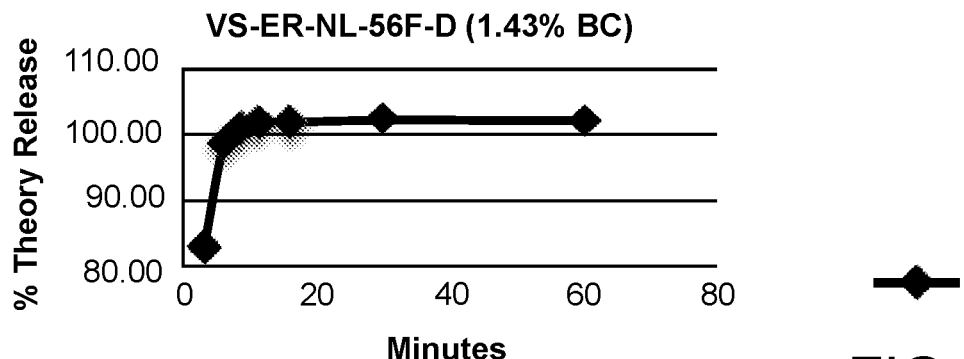
FIG. 13 is a graph of Dissolution Test Results for VS-ER-NL-56F-D (1.43% BC).

See FIG. 13 for a Graph of Dissolution Test Results for VS-ER-NL-56F-D (1.43% BC).

Conclusion for VS-ER-NL-56F-D (L 43% BC):

Tablet will be submitted for animal testing.

TABLE 9

Dissolution Test Results for VS-ER-NL-56F-E (2.14% BC)

| Time Minutes | Area | Vial Concentration | Concentration (mg) | % Theory-Release |
|---|---|---|---|---|
| 2 | 636 | 0.015828055 | 15.83 | 92.86 |
| 5 | 671.8 | 0.016707166 | 16.71 | 98.02 |
| 7.5 | 679.7 | 0.016901159 | 16.90 | 99.16 |
| 10 | 683.1 | 0.01698465 | 16.98 | 99.65 |
| 15 | 688.7 | 0.017122164 | 17.12 | 100.45 |
| 30 | 694.8 | 0.017271957 | 17.27 | 101.33 |
| 60 | 698.9 | 0.017372637 | 17.37 | 101.92 |

Figure 14:
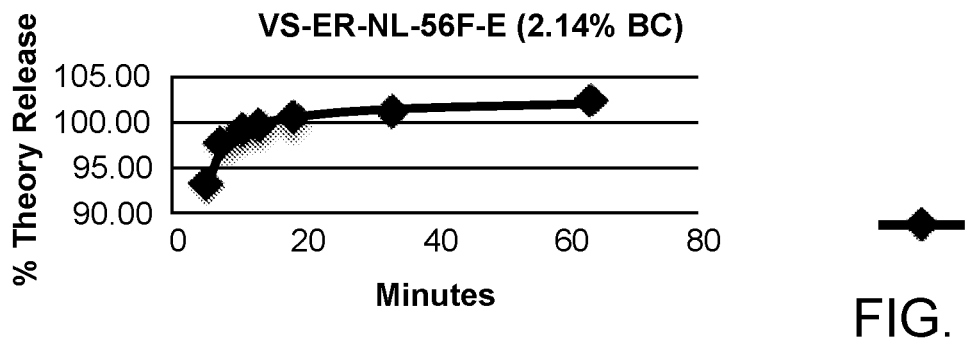
FIG. 14 is a graph of Dissolution. Test Results for VS-ER-NL-56F-E (2.14% BC).

See FIG. 14 for a Graph of Dissolution Test Results for VS-ER-NL-56F-E (2.14% BCI Conclusion for VS-ER-NL-56F-F (2.14% BC):
Tablet will be submitted for animal testing.

TABLE 10

Dissolution Test Results for VS-ER-NL-56F-F (1.43% BC)

| Time Minutes | Area | Vial Concentration | Concentration (mg) | % Theory Release |
|---|---|---|---|---|
| 2 | 402.7 | 0.010099105 | 10.10 | 89.27 |
| 5 | 430.4 | 0.01077931 | 10.78 | 95.28 |
| 7.5 | 438.8 | 0.010985582 | 10.99 | 97.11 |
| 10 | 446.2 | 0.011167297 | 11.17 | 98.71 |
| 15 | 454.8 | 0.01137848 | 11.38 | 100.58 |
| 30 | 470.6 | 0.011766467 | 11.77 | 104.01 |
| 60 | 483 | 0.012070964 | 12.07 | 106.70 |

Figure 15:
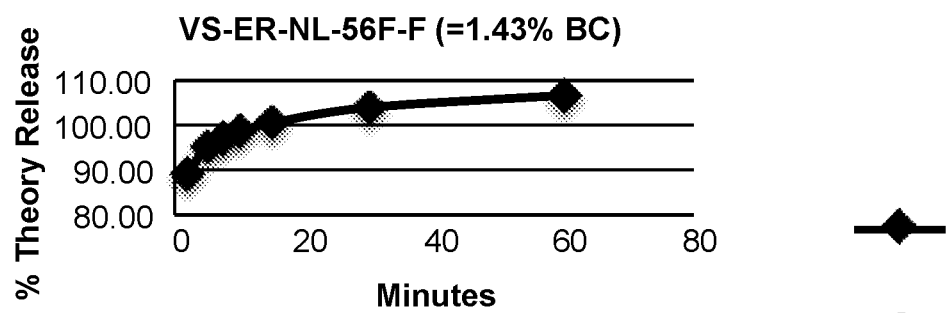
FIG. 15 is a graph of Dissolution Test Results for VS-ER-NL-56F-F (=1.43% BC).

See FIG. 15 for a Graph of Dissolution Tel Results for VS-ER-NL-56F-F (=1.43% BC).

Conclusion for VS-ER-NL-56F-F (1.43% BC):
Tablet will be submitted for animal testing.

Each reference cited in the text of the present disclosure is hereby incorporated by reference in its entirety. A number of embodiments of the invention have been described. Nevertheless, it will be understood that various modifications may be made without departing from the spirit and scope of the invention. Accordingly, other embodiments are within the scope of the following claims.

What is claimed is:

1. A pharmaceutical formulation comprising bromocriptine citrate in an amount that provides a dose of between 0.1 and 9.6 mg. bromocriptine, and excipients; wherein the excipients comprises 0.1-10% of a triglyceride, 30-90% mannitol, and 0.1-10% citric acid, and wherein the pharmaceutical formulation is substantially free of magnesium or lactose.

2. The pharmaceutical formulation of claim 1, wherein the pharmaceutical formulation is free of magnesium or lactose.

3. The pharmaceutical formulation of claim 1, wherein the pharmaceutical formulation comprises a tablet or oral dosage form.

4. The pharmaceutical formulation of claim 1, wherein the triglyceride comprises solid castor oil.

5. The pharmaceutical formulation of claim 1 wherein the bromocriptine citrate is more stable in an aqueous environment than bromocriptine mesylate.

6. The pharmaceutical formulation of claim 1 wherein the bromocriptine citrate is soluble in water to at least 500 mg/L at 20° C.

7. The pharmaceutical formulation of claim 3 comprising a parenteral dosage form.

8. The pharmaceutical dosage form of claim 3 comprising a sublingual dosage form.

9. The pharmaceutical dosage form of claim 7 having a pharmacokinetic profile with a plasma $T_{max}$ from about 1 to about 90 minutes after administration, and a plasma drug concentration of at least 50% $c_{max}$ for a duration of about 90 to about 360 minutes.

10. The pharmaceutical formulation of claim 7 wherein the bromocriptine is micronized.

11. A pharmaceutical formulation comprising 0.1-9.6 mg. bromocriptine citrate and excipients; wherein the excipients comprise 0.1-10% hydrogenated castor oil, 30-90% mannitol, and 0.1-10% citric acid, the pharmaceutical formulation is free of magnesium or lactose, and the bromocriptine is micronized and has a Dv90 of about 10 μm or lower.

12. The pharmaceutical formulation of claim 1 wherein the bromocriptine is micronized.

* * * * *